United States Patent
Matasi et al.

(10) Patent No.: US 7,041,666 B2
(45) Date of Patent: *May 9, 2006

(54) ADENOSINE A2$_A$ RECEPTOR ANTAGONISTS

(75) Inventors: Julius J. Matasi, Monmouth Junction, NJ (US); John P. Caldwell, Ringwood, NJ (US); Deen Tulshian, Lebanon, NJ (US); Lisa S. Silverman, Edison, NJ (US); Bernard R. Neustadt, West Orange, NJ (US)

(73) Assignee: Schering Corporation, Kenilworth, NJ (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/304,504

(22) Filed: Nov. 26, 2002

(65) Prior Publication Data
US 2003/0212080 A1 Nov. 13, 2003

Related U.S. Application Data
(60) Provisional application No. 60/334,293, filed on Nov. 30, 2001.

(51) Int. Cl.
| C07D 487/04 | (2006.01) |
| A61K 31/519 | (2006.01) |
| A61P 25/18 | (2006.01) |
| A61P 25/16 | (2006.01) |
| A61P 25/28 | (2006.01) |

(52) U.S. Cl. .............. 514/234.2; 544/263; 544/118; 544/244; 514/262.1; 514/81

(58) Field of Classification Search ............. None
See application file for complete search history.

(56) References Cited

U.S. PATENT DOCUMENTS

| 5,565,460 | A | | 10/1996 | Suzuki et al. |
| 6,222,035 | B1 | * | 4/2001 | Tsumuki et al. ............ 544/263 |
| 6,630,475 | B1 | | 10/2003 | Neustadt et al. |

FOREIGN PATENT DOCUMENTS

| EP | 0 404 190 B1 | 8/1985 |
| EP | 0 976 753 A1 | 2/2000 |
| EP | 1 116 722 A1 | 7/2001 |
| WO | WO 95/01356 | 1/1995 |
| WO | WO 97/05138 | 2/1997 |
| WO | WO98/42711 | 10/1998 |
| WO | WO 98/52568 | 11/1998 |
| WO | WO 200279204 A1 * | 10/2002 |
| WO | WO 03/048163 | 6/2003 |

OTHER PUBLICATIONS

Brown, Aust. J. CHem 33, 1147 (1980).*
"Parkinson's Treatments: L–dopa" <http://www.macalester.edu/~psych/whathap/UBNRP/parkinsons/ldopa.html> downloaded from the Internet Jul. 15, 2004.*

(Continued)

Primary Examiner—Mark L. Berch
(74) Attorney, Agent, or Firm—Anita W. Magatti

(57) ABSTRACT

Disclosed are compounds having the structural formula

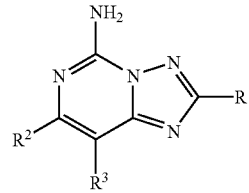

I or pharmaceutically acceptable salts or solvates thereof, wherein
R is optionally substituted heteroaryl, optionally substituted phenyl, cycloalkenyl, —C(=CH$_2$)CH$_3$, —C≡C—CH$_3$,

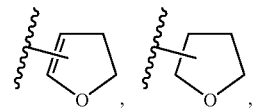

—CH=C(CH$_3$)$_2$,

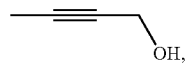

or —CH=CH—CH$_3$;
$R^2$ is —W—X, —NR$^{19}$(CH$_2$)$_m$—W—X, and —NR$^{19}$CH(CH$_3$)—W—X, or
$R^2$ is alkyl, alkenyl and —NR$^{18}$R$^{19}$, each optionally substituted —W—X;
$R^3$ is H, halo, alkyl, trifluoromethyl, alkoxy, alkoxyalkyl, hydroxyalkyl, alkylamino, alkylaminoalkyl, dialkylamino, dialkylaminoalkyl, aminoalkyl, aryl, heteroaryl, or CN;
$R^{18}$ is a bond, —CH(OH)—, —CH(CH$_3$)—, —C(CH$_3$)$_n$—, —(CH$_2$)$_n$—or —O(CH$_2$)$_n$—;
W is aryl or heteroaryl, each optionally substituted;
X is H, NH$_2$, or substituted amino, or X is —R$^{18}$—Y-Z;
and n, $R^{19}$, Y and Z are as defined in the specification; pharmaceutical compositions thereof, and methods of treating stroke or central nervous system diseases by administering the compound of the present invention to a patient in need of such treatment.

8 Claims, No Drawings

OTHER PUBLICATIONS

"Understanding Parkinson's Disease" http://www.stalevo.com/info/simplystated/parkinsons_disease_treatment.jsp?checked=y downloaded from the Internet Jul. 15, 2004.*

Hawkins et al, *Aminoboronic Anhydrides*, 82 (1960) p. 3863–3866.

Ashimori et al., *Chem. Pharm. Bull*, *38*, 9 (1990) p. 2446–2458.

Winter et al., *Chem Eur. J.*, *3*, 3 (1997) p. 410–416.

Urban Ungerstedt, *Eur. J. Of Pharm.*, *5* (1968) p. 107–110.

Ungerstedt et al., *Brain Research*, *24* (1970) p. 485–493.

* cited by examiner

ADENOSINE A2$_A$ RECEPTOR ANTAGONISTS

CROSS REFERENCE TO RELATED APPLICATION

This application claims priority to U.S. Provisional Application No. 60/334,293, filed Nov. 30, 2001.

BACKGROUND

This invention relates to substituted 1,2,4-triazolo[1,5-c] pyrimidine adenosine $A_{2a}$ receptor antagonists, the use of said compounds in the treatment of central nervous system diseases, in particular Parkinson's disease, and to pharmaceutical compositions containing said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists with different substitution at the 7-position have been disclosed previously, for example in WO 95/01356; U.S. Pat. No. 5,565,460; WO 97/05138; and WO 98/52568. Pyrazolo-substituted triazolo-pyrimidine adenosine $A_{2a}$ receptor antagonists are disclosed in U.S. Ser. No. 09/207,143, filed May 24, 2001.

SUMMARY OF THE INVENTION

This invention relates to compounds having the structural formula I

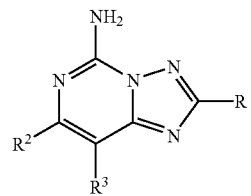

or a pharmaceutically acceptable salt or solvate thereof; wherein:

R is selected from the group consisting of $R^4$-heteroaryl, $R^5$-phenyl, $(C_4$–$C_6)$cycloalkenyl, —C(=CH$_2$)CH$_3$, —C≡C—CH$_3$,

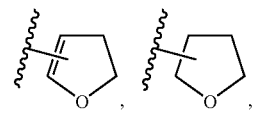

—CH=C(CH$_3$)$_2$,

and —CH=CH—CH$_3$;

$R^2$ is selected from the group consisting of —W—X, —NR$^{19}$(CH$_2$)$_m$—W—X, and —NR$^{19}$CH(CH$_3$)—W—X, or $R^2$ is selected from the group consisting of alkyl, alkenyl and —NR$^{18}$R$^{19}$, wherein said alkyl, alkenyl or —NR$^{18}$R$^{19}$ is optionally substituted by —W—X;

$R^3$ is selected from the group consisting of H, halo, alkyl, trifluoromethyl, alkoxy, alkoxyalkyl, hydroxyalkyl, alkylamino, alkylaminoalkyl, dialkylamino, dialkylaminoalkyl, aminoalkyl, aryl, heteroaryl, and CN;

$R^4$ is 1 to 3 substituents, which can be the same or different, and are independently selected from the group consisting of hydrogen, $(C_1$–$C_6)$-alkyl, —CF$_3$, halogen, —NO$_2$, —NR$^{15}$R$^{16}$, $(C_1$–$C_6)$alkoxy, $(C_1$–$C_6)$alkylthio, $(C_1$–$C_6)$alkylsulfinyl, $(C_1$–$C_6)$alkylsulfonyl, —COOR$^{17}$ and —C(O)NR$^6$R$^7$;

$R^5$ is 1 to 5 substituents, which can be the same or different, and are independently selected from the group consisting of hydrogen, halogen, $(C_1$–$C_6)$alkyl, hydroxy, $(C_1$–$C_6)$alkoxy, —CN, —NH$_2$, $(C_1$–$C_6)$alkylamino, di-$((C_1$–$C_6)$alkyl)amino, —CF$_3$, —OCF$_3$, —S(O)$_{0\text{-}2}$$(C_1$–$C_6)$ alkyl and —CH$_2$—SO$_2$-phenyl;

$R^6$ and $R^7$, which can be the same or different, are each independently selected from the group consisting of hydrogen and $(C_1$–$C_6)$alkyl;

$R^8$ is 1 to 5 substituents, which can be the same or different, and are independently selected from the group consisting of hydrogen, halogen, $(C_1$–$C_6)$alkyl, hydroxy, $C_1$–$C_6$ alkoxy, —CN, amino, di-$((C_1$–$C_6)$alkyl)amino, —CF$_3$, —OCF$_3$, acetyl, —NO$_2$, hydroxy$(C_1$–$C_6)$alkoxy, $(C_1$–$C_6)$-alkoxy$(C_1$–$C_6)$alkoxy, di-$((C_1$–$C_6)$-alkoxy) $(C_1$–$C_6)$alkoxy, $(C_1$–$C_6)$-alkoxy$(C_1$–$C_6)$alkoxy-$(C_1$–$C_6)$-alkoxy, carboxy$(C_1$–$C_6)$-alkoxy, $(C_1$–$C_6)$-alkoxycarbonyl $(C_1$–$C_6)$alkoxy, $(C_3$–$C_6)$cycloalkyl$(C_1$–$C_6)$alkoxy, di-$((C_1$–$C_6)$alkyl)amino$(C_1$–$C_6)$alkoxy, morpholinyl, $(C_1$–$C_6)$ alkyl-SO$_2$—, $(C_1$–$C_6)$alkyl-SO$_2$—$(C_1$–$C_6)$alkoxy, tetrahydropyranyloxy, $(C_1$–$C_6)$alkylcarbonyl$(C_1$–$C_6)$-alkoxy, $(C_1$–$C_6)$-alkoxycarbonyl, $(C_1$–$C_6)$alkylcarbonyloxy $(C_1$–$C_6)$-alkoxy, —SO$_2$NH$_2$, phenoxy,

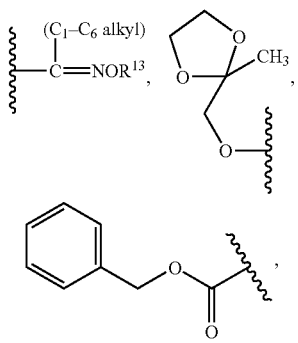

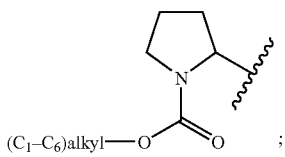

—O—CH$_2$—P(O)(OR$^6$)$_2$,— and —P(O)(OR$^6$)$_2$; or adjacent R$^8$ substituents together are —O—CH$_2$—O—, —O—CH$_2$CH$_2$—O—, —O—CF$_2$—O— or —O—CF$_2$CF$_2$—O— and form a ring with the carbon atoms to which they are attached;

R$^9$ is selected from the group consisting of (C$_1$–C$_6$)alkyl, R$^8$-aryl-, R$^8$-aryl(C$_1$–C$_6$)alkyl-, thienyl, pyridyl, (C$_3$–C$_6$)-cycloalkyl, (C$_1$–C$_6$)alkyl-OC(O)—NH—(C$_1$–C$_6$)alkyl-, di-((C$_1$–C$_6$)alkyl)aminomethyl, cycloheteroalkyl(C$_1$–C$_6$)alkyl, aryloxy(C$_1$–C$_6$)alkyl, alkoxy(C$_1$–C$_6$)alkyl and

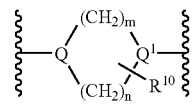

R$^{10}$ is 1–2 substituents, which can be the same or different, and are independently selected from the group consisting of hydrogen, (C$_1$–C$_6$)alkyl, R$^5$-aryl and R$^4$-heteroaryl, or two R$^{10}$ substituents on the same carbon can form =O;

R$^{11}$ is hydrogen or (C$_1$–C$_6$)alkyl; —C(O)alkyl, or R$^{17}$ and R$^{11}$ taken together are —(CH$_2$)$_p$-A-(CH$_2$)$_q$, wherein p and q are each independently 2 or 3 and A is selected from the group consisting of a bond, —CH$_2$—, —S— and —O—, and form a ring with the nitrogen to which they are attached;

R$^{12}$ is 1–2 substituents, which can be the same or different, and are independently selected from the group consisting of hydrogen, (C$_1$–C$_6$)alkyl, hydroxy, (C$_1$–C$_6$) alkoxy, halogen, and —CF$_3$;

R$^{13}$ is selected from the group consisting of H, (C$_1$–C$_6$) alkyl, phenyl, benzyl, (C$_2$–C$_6$)alkenyl, (C$_1$–C$_6$)alkoxy (C$_1$–C$_6$)alkyl, di-((C$_1$–C$_6$)alkyl)amino(C$_1$–C$_6$)alkyl, pyrrolidinyl(C$_1$–C$_6$)alkyl and piperidino(C$_1$–C$_6$)alkyl;

R$^{14}$ is selected from the group consisting of H, halogen, (C$_1$–C$_6$)alkyl or (C$_1$–C$_6$)alkoxy;

R$^{15}$ is selected from the group consisting of H and (C$_1$–C$_6$)alkyl;

R$^{16}$ is selected from the group consisting of H, (C$_1$–C$_6$) alkyl-C(O)— and (C$_1$–C$_6$)alkyl-SO$_2$—;

R$^{17}$ is selected from the group consisting of (C$_1$–C$_6$)alkyl, (C$_1$–C$_6$)hydroxyalkyl, (C$_3$–C$_6$)cycloalkyl, (C$_1$–C$_6$)alkoxy (C$_1$–C$_6$)alkyl, (C$_1$–C$_6$)alkoxy, (C$_1$–C$_6$)alkoxy(C$_1$–C$_6$) alkyl, allyl, propargyl, R$^8$-heteroaryl-, R$^8$-aryl- and R$^8$-aryl (C$_1$–C$_6$)alkyl-;

R$^{18}$ is selected from the group consisting of a bond, —CH$_2$—, —CH(OH)—, —CH(CH$_3$)—, —C(CH$_3$)$_n$—, —(CH$_2$)$_n$—, and —O(CH$_2$)$_n$—, R$^{19}$ is selected from the group consisting of H, (C$_1$–C$_6$) alkyl, (C$_1$–C$_6$)alkyl(C$_1$–C$_6$)cycloalkyl, (C$_1$–C$_6$)cycloalkyl (C$_1$–C$_6$)alkyl and (C$_1$–C$_6$)alkoxy(C$_1$–C$_6$)alkyl;

Q and Q$^1$ can be the same or different and are each independently selected from the group consisting of

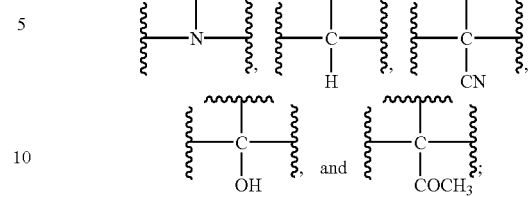

m and n are each independently 1–3;

p and q are each independently 0–2;

s is 0–4;

W is aryl or heteroaryl having 1–3 heteroatoms, which can be the same or different, and are independently selected from the group consisting of N, O and S, and wherein said aryl or heteroaryl is optionally substituted with 1–3 substituents, which can be the same or different, and are independently selected from the group consisting of alkyl, aryl, alkylcycloalkyl, halo, hydroxy, hydroxyalkyl, alkoxy, alkylalkoxy, alkoxyalkoxy, —NR$^6$R$^7$, (C$_2$–C$_6$)alkene, and —CN, or X is selected from the group consisting of H, NH$_2$, —N(R$^6$)(CH$_2$)s-aryl, —N(R$^6$)(CH$_2$)$_s$-heteroaryl, —N(R$^6$) (CH$_2$)$_{m+1}$—OH, and —N(CH$_3$)$_2$, or X is —R$^{18}$—Y-Z;

Y is selected from the group consisting of —N(R$^6$) CH$_2$CH$_2$N(R$^7$)—, —N(R$^6$)(CH$_2$)$_n$aryl, —OCH$_2$CH$_2$N (R$^6$)—, —O—, —S—, —CH$_2$S—, —(CH$_2$)$_{2-3}$—N(R$^6$)—, R$^8$-divalent heteroaryl,

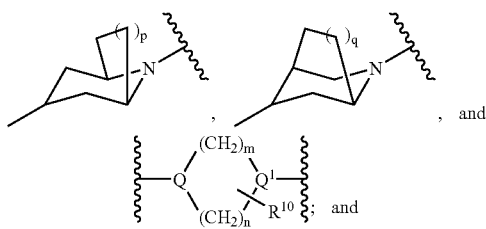

Z is selected from the group consisting of H, alkyl, alkoxyalkyl, R$^8$-aryl-, R$^8$-aryl(C$_1$–C$_6$)alkyl-, R$^8$-heteroaryl-, R$^8$-bicyclicalkyl-, aminoalkyl, alkylamino, NH$_2$, —N—(R$^6$) (CH$_2$)$_s$-aryl, —N(R$^6$)(CH$_2$)$_s$-heteroaryl, —N(R$_6$)C(O) OR$^{17}$, alkylcycloheteroalkyl, cycloheteroalkyl, cycloheteroalkylalkyl, alkoxycycloheteroalkyl, heteroaryl; R$^8$-benzofused heteroaryl-, diphenylmethyl and R$^9$—C (O)—; or when Y is

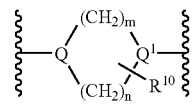

Z can also be —OH, R$^9$—SO$_2$—, R$^{17}$—N(R$^{11}$)(CH$_2$)$_s$—C (O)—, R$^{17}$—OC(O)—, R$^{17}$—O(CH$_2$)$_n$C(O)—, benzofused heteroaryl(CH$_2$)$_n$C(O)—, benzofused heteroaryl(CH$_2$)$_n$— or R$^{17}$—N(R$^{11}$)—C(S)—; or when Q is

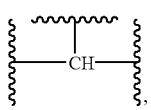

Z can also be $R^{17}R^{11}N-$, phenylamino or pyridylamino; or

Z and Y taken together are selected from the group consisting of

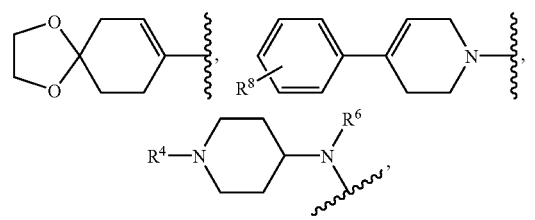

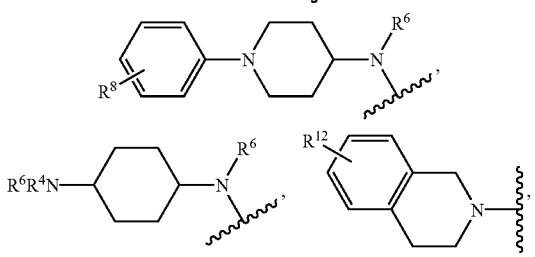

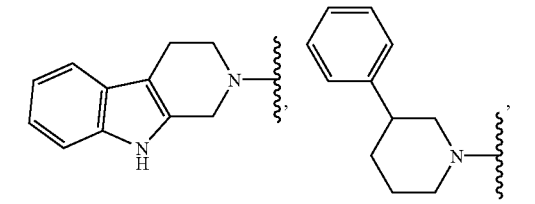

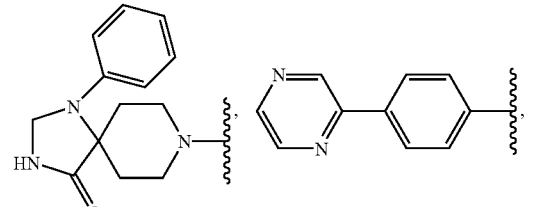

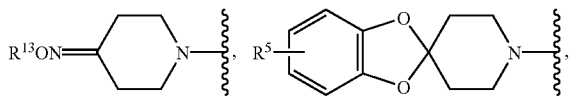

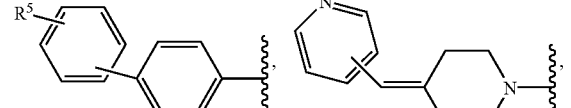

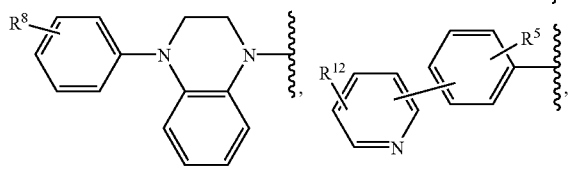

or an N-oxide thereof,

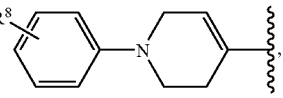

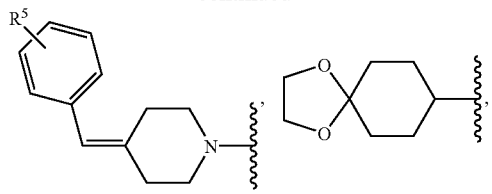

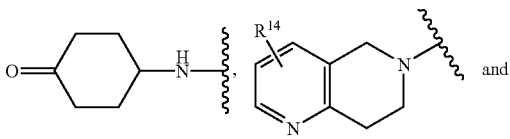

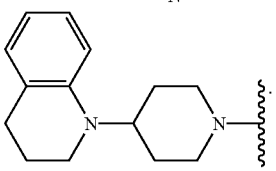

Another aspect of the invention relates to a pharmaceutical composition comprising a one or more compounds of formula I and one or more pharmaceutically acceptable carriers.

Another aspect of the invention relates to a pharmaceutical composition comprising one or more compounds of formula I and one or more agents known to be useful in the treatment of Parkinson's in one or more pharmaceutically acceptable carriers.

Another aspect of the invention relates to a method of treating stroke or central nervous system diseases comprising administering one or more compounds of formula I to a patient in need of such treatment. In this aspect of the invention, the central nervous system diseases include cognitive diseases or neurodegenerative diseases such as such as Parkinson's disease, senile dementia or psychoses of organic origin. Preferably, the amount of compound administered to the patient is a therapeutically effective amount.

Another aspect of the invention relates to a method of treating Parkinson's disease with a combination one or more compounds of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. In this aspect of the invention, one or more compounds of formula I and one or more other anti-Parkinson's agents can be administered simultaneously or sequentially in separate dosage forms.

Yet, another aspect of the invention relates to a kit comprising in separate containers in a single package pharmaceutical compositions for use in combination to treat Parkinson's disease wherein one container comprises a pharmaceutical composition comprising an one or more compounds of formula I in one or more pharmaceutically acceptable carriers, and wherein, in separate containers, one or more pharmaceutical compositions each comprise one or more agents useful in the treatment of Parkinson's disease in one or more pharmaceutically acceptable carriers.

DETAILED DESCRIPTION OF THE INVENTION

This invention relates to compounds having the structural formula I

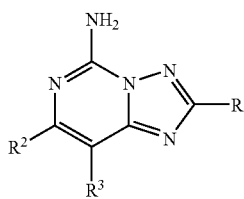

I or a pharmaceutically acceptable salt or solvate of said compound, wherein R, $R^2$, and $R^3$ are as defined above.

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

When any variable (e.g., $R^2$) occurs more than one time in any constituent, its definition in each occurrence is independent of its definition at every other occurrence. Also, combinations of substituents and/or variables are permissible only if such combinations result in stable compounds.

Alkyl (including the alkyl portions of alkoxy, alkylamino, and dialkylamino) means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having about 1 to about 6 carbon atoms in the chain which may be straight or branched. Preferred alkyl groups in the present invention are lower alkyl groups. Non-limiting examples of suitable alkyl groups include methyl, ethyl, n-propyl, isopropyl, n-butyl, t-butyl, n-pentyl, heptyl, nonyl, decyl, trifluoromethyl and cyclopropylmethyl. Alkyl groups can be substituted with one or more substituents, which may be the same or different, and are selected from the group consisting of alkyl, aryl, heteroaryl, hydroxy, alkoxy, halo, nitro, cyano, and cycloalkyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

Alkoxyalkyl is a moiety containing an alkoxy linked to the main group via an alkyl.

"Alkoxycarbonyl" means an alkyl-O—C(O)— group. Non-limiting examples of suitable alkoxycarbonyl groups include methoxycarbonyl and ethoxycarbonyl. The alkoxy is linked to an adjacent moiety through the carbonyl.

"Alkylsulfonyl" means an alkyl-S(O)$_2$— group. Preferred groups are those in which the alkyl group is lower alkyl. The alkyl is linked to an adjacent moiety through the sulfonyl.

"Alkylsulfinyl" means an alkyl-S(O)— group. Preferred groups are those in which the alkyl group is lower alkyl. The alkyl is linked to an adjacent moiety through the sulfinyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 2 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain which may be straight or branched. Non-limiting examples of suitable alkenyl groups include ethenyl, propenyl, n-butenyl, 3-methylbut-2-enyl, and n-pentenyl.

Alkanoyl is an alkyl attached to a carbonyl wherein alkyl has the same meaning as defined above.

Alkylene, referring to a divalent alkyl group, similarly refers to straight or branched chains.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylamino, arylamino, alkylaryl, aralkenyl, heteroaralkyl, alkylheteroaryl, heteroaralkenyl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

The term "optionally substituted" means optional substitution with the specified groups, radicals or moieties.

"Cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like. The cycloalkyl can be optionally substituted with one or more "ring system substituents" which may be the same or different, and are as defined above.

"Cycloheteroalkyl" means a non-aromatic mono- or multicyclic fused ring system comprising 3 to 10 ring carbon atoms, preferably 3 to 7 ring carbon atoms, more preferably 3 to 6 ring carbon atoms, wherein the cycloheteroalkyl has 1 or 2 heteroatoms independently selected from O, S or N, said heteroatom(s) interrupting a carbocyclic ring structure provided that the rings do not contain adjacent oxygen and/or sulfur atoms. The cycloheteroalkyl can be optionally substituted with one or more "ring system substituents" which may be the same or different, and are as defined above.

"Aryl" means an aromatic monocyclic or multicyclic ring system comprising 6 to 14 ring carbon atoms, preferably 6 to 10 ring carbon atoms. The aryl group can be optionally substituted with one or more "ring system substituents" which may be the same or different, and are as defined herein. Non-limiting examples of suitable aryl groups include phenyl and naphthyl.

"Heteroaryl" represents cyclic aromatic groups of 5 or 6 ring atoms or bicyclic groups of 11 to 12 ring atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Preferred heteroaryls contain 5 to 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl and the like and the N-oxides thereof. Useful 5-membered heteroaryl rings include furyl, thienyl, pyrrolyl, thiazolyl, isothiazolyl, imidazolyl, pyrazolyl, isoxazolyl and the like. Useful bicyclic groups include benzo-fused ring systems derived from the heteroaryl groups named above, e.g. quinolyl, phthalazinyl, quinazolinyl, benzofuranyl, benzothienyl, indolyl and the like.

Divalent heteroaryl means a heteroaryl ring bonded to two different groups. In the context of this invention, when Y is divalent $R^8$-heteroaryl, one ring member is attached to the variable X, and another ring member is attached to variable Z; the $R^8$ substituents are attached to the remaining ring members. Divalent heteroaryl groups are named by adding "diyl" to the name of the ring, for example, a pyridinediyl ring is shown:

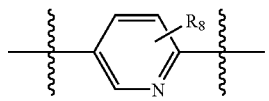

Arylcarbonyl is an aryl linked to the main group via a carbonyl wherein aryl has the same definition as described above.

Alkylaryl is a moiety containing an alkyl linked to the main group or ring via an aryl group.

Cycloalkylene refers to a divalent cycloalkyl group.

The term "solvate" as used herein means an aggregate that consists of a solute ion or molecule with one or more solvent molecules, for example, a hydrate containing such ions.

The term "prodrug" means a compound that is a drug precursor which, following administration to a patient, releases the drug in vivo via some chemical or physiological process (e.g., a prodrug on being brought to the physiological pH or through enzyme action is converted to the desired drug form).

The term "therapeutically effective amount" as used herein means an amount sufficient to treat central nervous system diseases such as depression, cognitive diseases and neurodegenerative diseases such as Parkinson's disease, senile dementia and psychoses of organic origin. Preferably, the therapeutically effective amount of active compound in a unit dose of preparation can range from about 0.1 mg to about 1000 mg, more preferably from about 1 mg to about 300 mg.

Certain compounds of the invention may exist in different stereoisomeric forms (e.g., enantiomers, diastereoisomers and atropisomers). The invention contemplates all such stereoisomers both in pure form and in mixture, including racemic mixtures.

The compounds of formula I can form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides such as compound 174 disclosed herein, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; and Anderson et al, *The Practice of Medicinal Chemistry* (1996), Academic Press, New York). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

These compounds possess antagonistic activity at $A_{2a}$ receptors and are useful in the treatment of Parkinson's disease and depression. They may be used alone or in combination with dopaminergic agents such as L-DOPA or ropinrole. They may also be used in conjunction with known anti-depressant therapeutic agents.

The compounds of formula I are prepared by the methods shown in the following three reaction schemes:

Scheme 1:

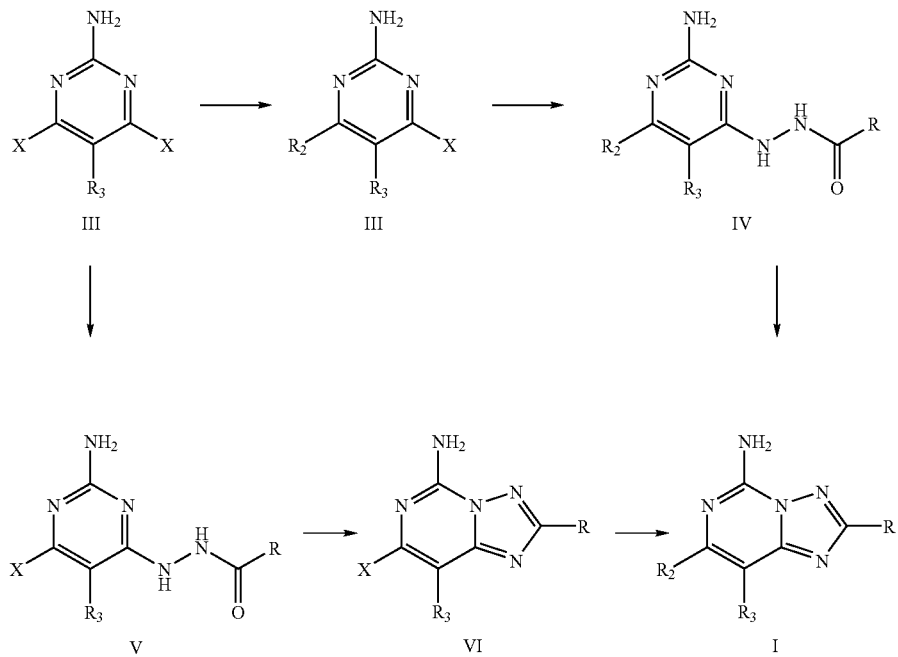

where X = Cl, Br, I

In Scheme 1, palladium catalyzed coupling reactions between 2-amino-4,6-dichcloro-pyrimidine (where X=Cl) II and an aryl boronic acid in a toluene, ethanol, $Na_2CO_3$ (aq) solution at elevated temperature yields compounds of formula III. The treatment of III with the appropriate hydrazide in butanol at elevated temperature provides a hydrazide IV. Treatment of compounds of formula IV with N, O-bis(trimethylsilyl)acetamide at elevated temperature provides compounds of formula I.

Alternatively, when starting material II, 2-amino-4,6-dichcloro-pyrimidine (where X=Cl), is treated with an appropriate hydrazide in butanol at elevated temperature, the corresponding hydrazide V is produced. Treating compounds of structure V in N, O-bis(trimethylsilyl)acetamide provides compounds of formula VI. The palladium catalyzed coupling reactions between compounds VI (where X=Cl) and an aryl boronic acid in a toluene, ethanol, $Na_2CO_3$ (aq) solution at elevated temperature yield compounds of formula I.

Scheme 2

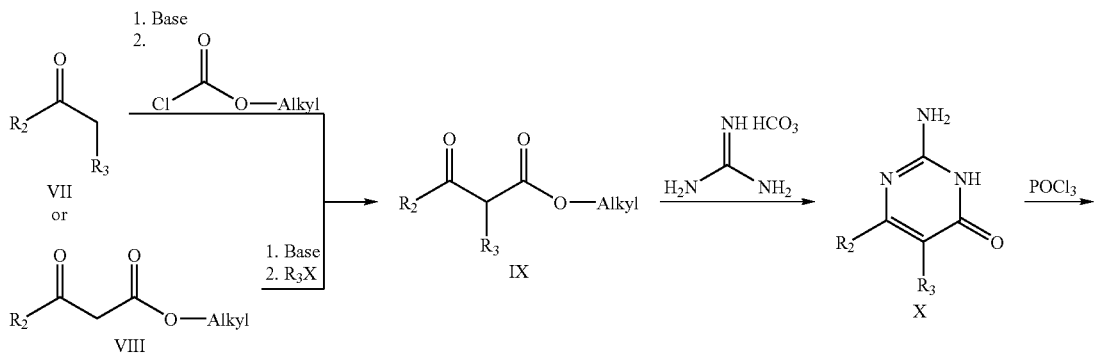

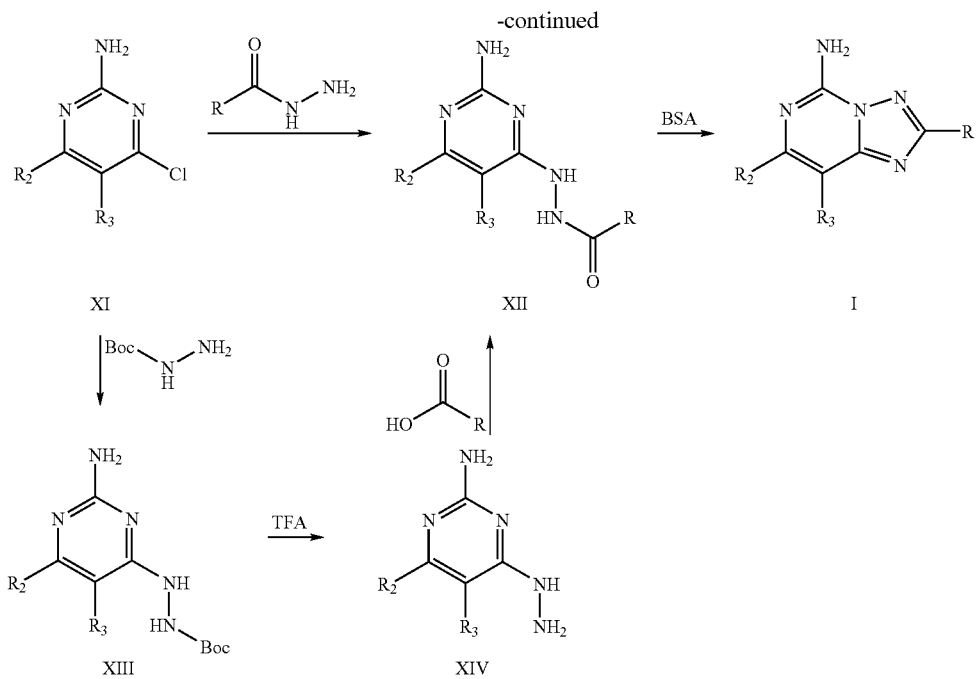

XI → XII → I

XIII → XIV

Compounds of formula I can also be prepared as shown above in Scheme 2. The desired precursor IX may be prepared either from treatment of the appropriate ketone VII with alkylchloroformate in the presence of base or from the treatment of an appropriate β-keto ester VII with $R^3X$ under basic conditions. The β-keto ester IX can undergo condensation reaction with guanadine carbonate at elevated temperature in an inert solvent, such as DMF, to produce the amino pyrimidine X. Treatment of X with $POCl_3$ at elevated temperature affords the chloro analog XI. The treatment of XI with the appropriate hydrazide in butanol at elevated temperature provides a hydrazide XII. Treatment of compounds of formula XII with N, O-bis(trimethylsilyl)acetamide provides compounds of formula I.

Alternatively, treatment of XI with the Boc-protected hydrazine in an inert solvent, such as DMF, at elevated temperature affords compounds of formula XIII which in turn can be deprotected with an acid, such as TFA, at room temperature to afford the free hydrazine XIV. Treatment of XIV with the appropriate carboxylic acid in the presence of a coupling agent, such as EDCl, in an inert solvent, such as DMF, at room temperature produces hydrazide XII.

Scheme 3

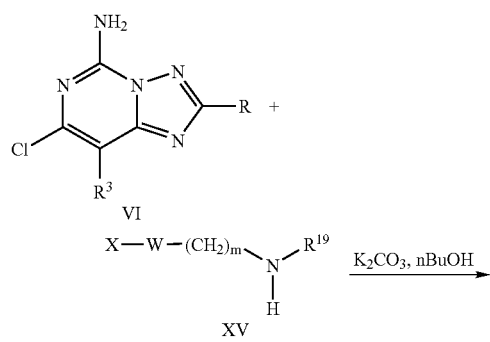

-continued

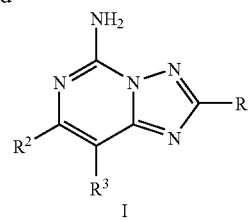

where $R^2 = X-W-(CH_2)_m-\underset{R^{19}}{N}\xi$ and $R^{19}$ is as defined above Alternatively, compounds of formula I can be prepared as shown in Scheme 3. Compound VI can undergo nucleophilic displacement reactions with amines of formula XV by treatment with $K_2CO_3$ in nBuOH at elevated temperatures to produce compounds of formula I.

Another aspect of the invention relates to a pharmaceutical composition comprising a one or more compounds of formula I and one or more pharmaceutically acceptable carriers.

Another aspect of the invention relates to a pharmaceutical composition comprising one or more compounds of formula I and one or more agents known to be useful in the treatment of Parkinson's in one or more pharmaceutically acceptable carriers.

Another aspect of the invention relates to a method of treating stroke or central nervous system diseases comprising administering one or more compounds of formula I to a patient in need of such treatment. In this aspect of the invention, the central nervous system diseases include cognitive diseases or neurodegenerative diseases such as such as Parkinson's disease, senile dementia or psychoses of organic origin. In particular, the invention is drawn to the method of treating Parkinson's disease comprising administering one or more compounds of formula I to a patient in need of such treatment. Preferably, the amount of compound administered is a therapeutically effective amount.

Another aspect of the invention relates to a method of treating Parkinson's disease with a combination of one or more compounds of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. In this aspect of the invention, one or more compounds of formula I and one or more other anti-Parkinson's agents can be administered simultaneously or sequentially in separate dosage forms.

Yet, another aspect of the invention relates to a kit comprising in separate containers in a single package pharmaceutical compositions for use in combination to treat Parkinson's disease wherein one container comprises a pharmaceutical composition comprising one or more compounds of formula I in one or more pharmaceutically acceptable carriers, and wherein, in separate containers, one or more pharmaceutical compositions each comprise one or more agents useful in the treatment of Parkinson's disease in one or more pharmaceutically acceptable carriers.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent by weight of active ingredient, which include compounds of formula I and optionally other compounds useful for treating Parkinson's disease. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and solidify.

Liquid form preparations include solutions, suspensions and emulsions. An example of this is water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to about 1000 mg, more preferably from about 1 mg to about 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from about 10 mg to about 2000 mg/day preferably from about 10 mg to about 1000 mg/day, in two to four divided doses to provide relief from central nervous system diseases such as Parkinson's disease. The compounds are non-toxic when administered within this dosage range.

EXAMPLES

The following examples serve to provide further appreciation of the invention, but are not meant in any way to restrict the effective scope of the invention.

Example 1

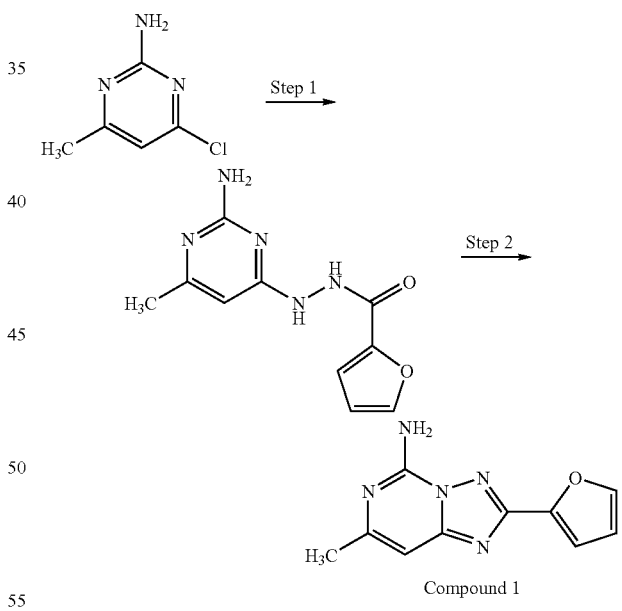

Compound 1

STEP 1: Heat a mixture of 2-amino-4-chloro-6-methylpyrimidine (1.44 g, 10.00 mmol) and 2-furoic hydrazide (1.89 g, 15.0 mmol) in butanol (50 mL) at 90° C. for 16 h. After cooling the reaction mixture to room temperature, the residue was washed with methanol and the resulting preciptate filtered to afford a solid.

STEP 2: Heat the solid produced in Step 1 (0.77 g, 3.30 mmol) in N,O-bis(trimethylsilyl)acetamide (5 mL) at 120° C. overnight. Cool the reaction mixture and pour it on ice water and stir for 4 h. Extract the mixture with ethyl acetate dry over sodium sulfate, filter, and concentrate in vacuo.

Purify the residue on silica gel chromatography to produce a solid. $^1$H NMR (DMSO-d$_6$) δ 7.83 (br. M, 3H), 7.10 (dd, 1H), 6.75 (s, 1H), 6.64 (dd, 1H), 2.30 (s, 3H). Mass spectrum (ESI): 216.0.

Example 2

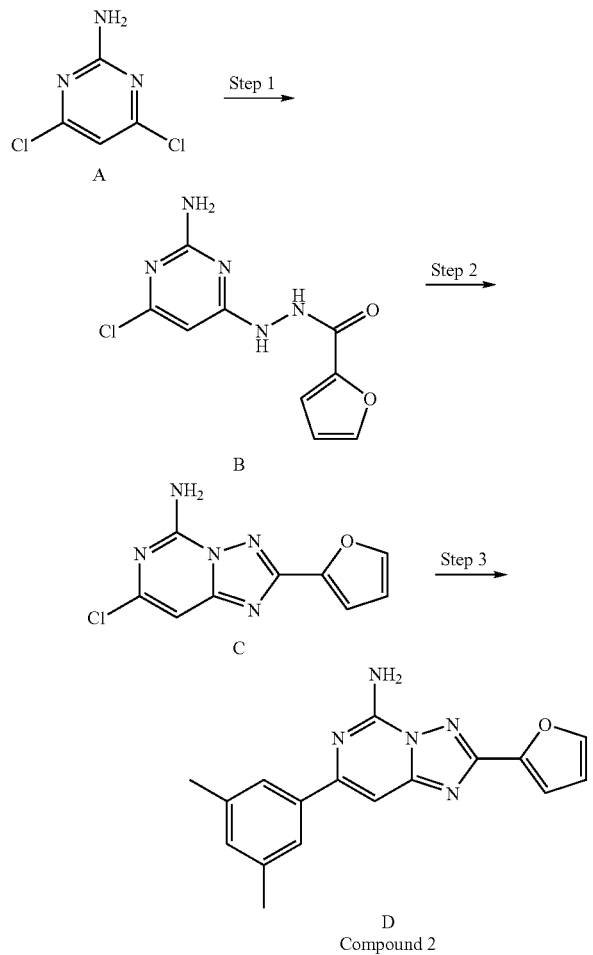

STEP 1: A mixture of 2-amino-4,6-dichcloro-pyrimidine (10.00 g, 60.98 mmol) and 2-furoic hydrazide (7.68 g, 60.98 mmol) was heated in butanol (200 mL) at 90° C. for 20 h. The reaction mixture was cooled to room temperature, the mixture was extracted with ethyl acetate and water, the ethyl acetate layer collected and dried over sodium sulfate, filtered, and concentrated in vacuo. The residue was purified on silica gel chromatography to produce a solid B. Mass spectrum (ESI): 254.0, $^1$H NMR (DMSO-d$_6$) δ 5.76(br s, 1H), 6.61(br s, 2H), 6.64(m, 1H), 7.20(d, 1H), 7.88(s, 1H), 9.01(brs, 1H), 10.32(brs, 1H).

STEP 2: The product of Step 1 B (9.20 g, 36.27 mmol) was heated in N,O-bis(trimethylsilyl)acetamide (49.4 g, 242.14 mmol) at 120° C. overnight. The reaction mixture was cooled and poured onto ice water and stirred for 4 h. The mixture was extracted with ethyl acetate dried over sodium sulfate, filtered, and concentrated in vacuo. The residue was purifed on silica gel chromatography to produce a solid C. Mass spectrum (ESI): 236.0, $^1$H NMR (CDCl$_3$) δ 6.18(br s, 2H), 6.61(m, 1H), 7.04(s, 1H), 7.24(d, 1H), 7.64(s, 1H).

STEP 3: In a sealed tube, heat the product of Step 2 C (50 mg, 0.21 mmol) with 3,5-Dimethylbenzeneboronic acid (63 mg, 0.42 mmol), Pd (PPh$_3$)$_4$ (24 mg, 0.02 mmol), and sodium carbonate (74 mg, 2.10 mmol) in a solvent system of 3/1/1//toluene/ethanol/water at 103° C. for a period of 4 h. After cooling the reaction mixture to room temperature, the mixture was extracted with EtOAc and water. The organic portion was collected, dried over sodium sulfate, filtered, and concentrated in vacuo. The residue was purified by silica gel chromatography to produce a solid D. Mass spectrum (ESI): 306.1, $^1$H NMR (CDCl$_3$) δ 2.41(s, 6H), 5.95(br s, 2H), 7.10(s, 1H), 7.24 (s, 1H), 7.39(s, 1H), 7.60(s, 2H), 7.64(s, 1H).

The compounds below were prepared in a similar fashion:

| COMPOUND NUMBER | STRUCTURE | M + 1 (ESI) |
|---|---|---|
| 3 | (structure shown) | 306.1 |

-continued

| COMPOUND NUMBER | STRUCTURE | M + 1 (ESI) |
| --- | --- | --- |
| 4 | 7-(3,5-dichlorophenyl)-2-(furan-2-yl)-[1,2,4]triazolo[1,5-c]pyrimidin-5-amine | 346.1 |
| 5 | 7-(3,4-dichlorophenyl)-2-(furan-2-yl)-[1,2,4]triazolo[1,5-c]pyrimidin-5-amine | 346.1 |
| 6 | 7-(2,4-dichlorophenyl)-2-(furan-2-yl)-[1,2,4]triazolo[1,5-c]pyrimidin-5-amine | 346.1 |
| 7 | 2-(furan-2-yl)-7-(4-methoxyphenyl)-[1,2,4]triazolo[1,5-c]pyrimidin-5-amine | 308.1 |
| 8 | 2-(furan-2-yl)-7-(2,4-dimethoxyphenyl)-[1,2,4]triazolo[1,5-c]pyrimidin-5-amine | 338.1 |
| 9 | 2-(furan-2-yl)-7-(3,4-dimethoxyphenyl)-[1,2,4]triazolo[1,5-c]pyrimidin-5-amine | 338.1 |

-continued
| COMPOUND NUMBER | STRUCTURE | M + 1 (ESI) |
|---|---|---|
| 10 | 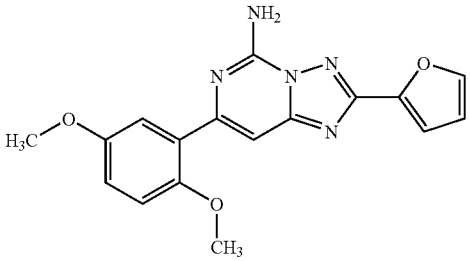 | 338.1 |
| 11 | 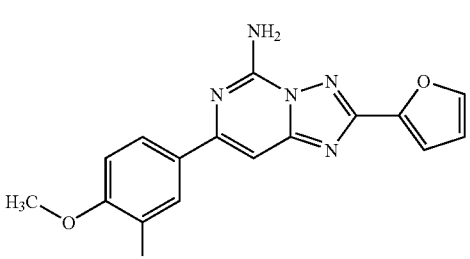 | 322.1 |
| 12 | 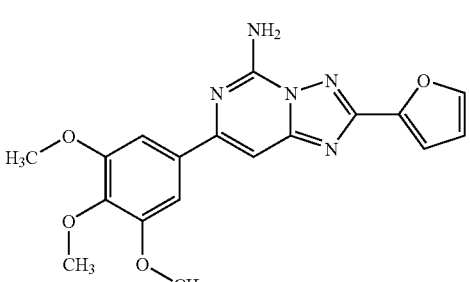 | 368.1 |
| 13 | 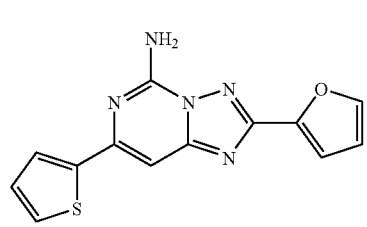 | 284.1 |
| 14 | 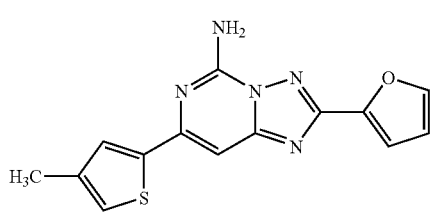 | 298.1 |

-continued

| COMPOUND NUMBER | STRUCTURE | M + 1 (ESI) |
|---|---|---|
| 15 | 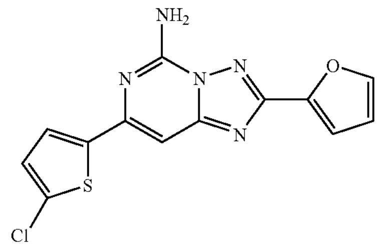 | 318.1 |
| 16 | 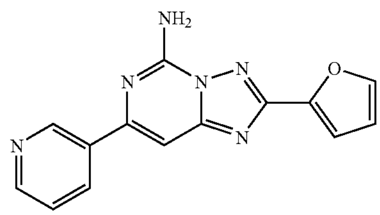 | 279.0 |
| 17 | 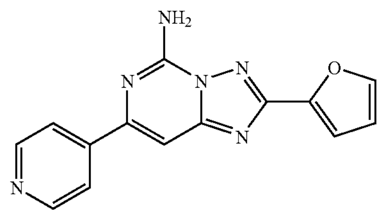 | 279.0 |
| 18 | 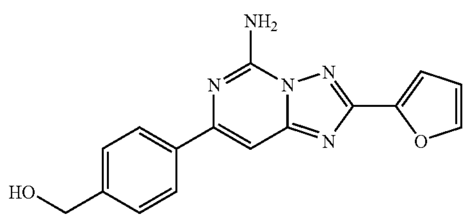 | 308.1 |

Example 3

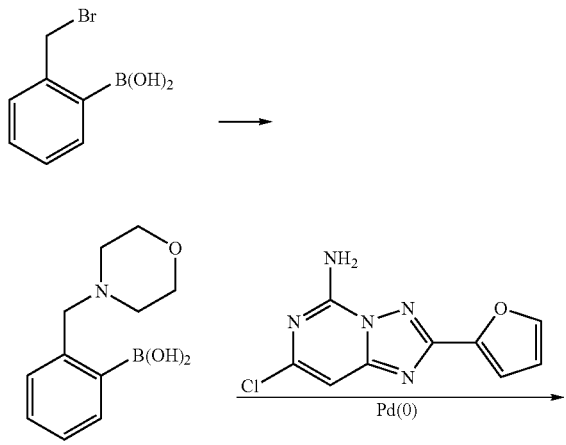

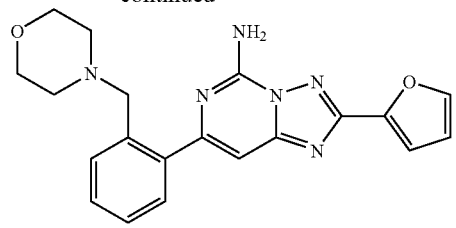

Compound 19

The ortho-(N-morpholinomethyl)-benzeneboronic acid was prepared by a known literature procedure (*J. Am. Chem. Soc.*, p. 3863, 1960) and subsequently used to produce the target compound as described in Example 2. Mass spectrum (ESI): 377.1, $^1$H NMR (CDCl$_3$) δ 2.36(t, 4H), 3.56(t, 4H), 6.04(br s, 2H), 6.61(m, 1H), 7.30(s, 1H), 7.39(m, 2H), 7.51(m, 2H), 7.65(d, 1H).

The compounds below were prepared in a similar fashion:

| COMPOUND NUMBER | STRUCTURE | M + 1 (ESE) |
|---|---|---|
| 20 | 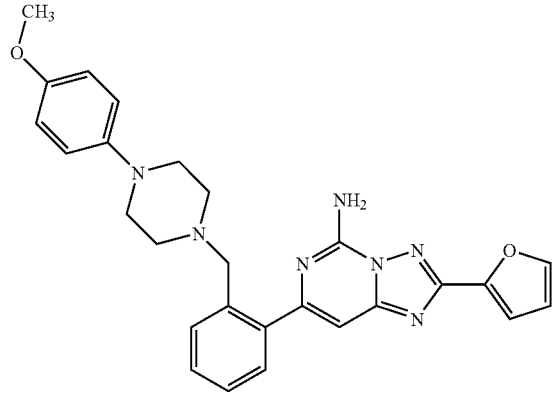 | 482.1 |
| 21 | 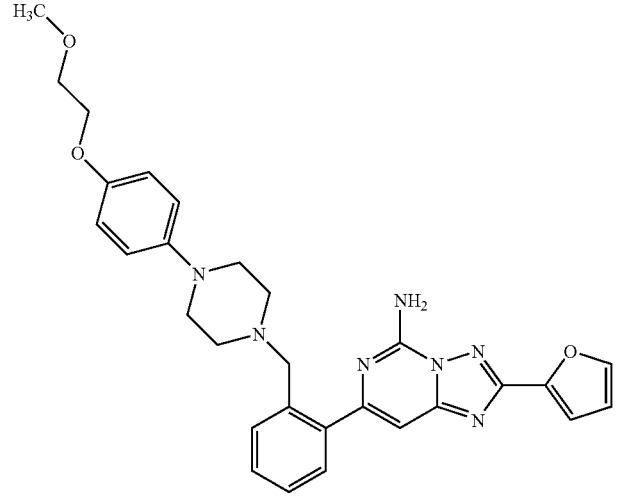 | 526.1 |
| 22 | 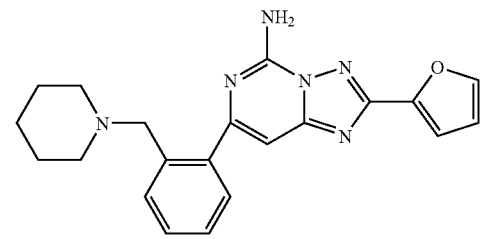 | 375.1 |
| 23 | 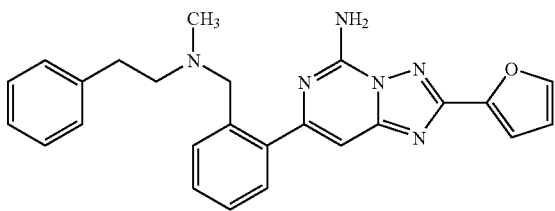 | 425.1 |
| 24 | 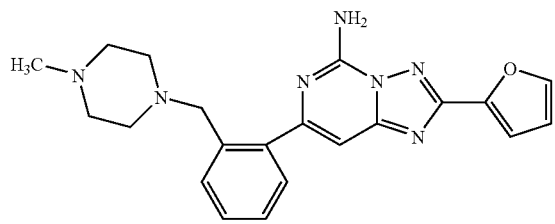 | 390.1' |

| COMPOUND NUMBER | STRUCTURE | M + 1 (ESE) |
|---|---|---|
| 25 | 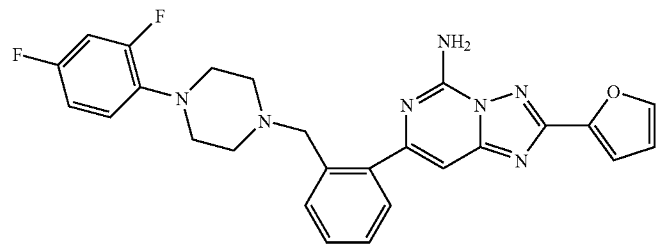 | 488.1 |

Example 4

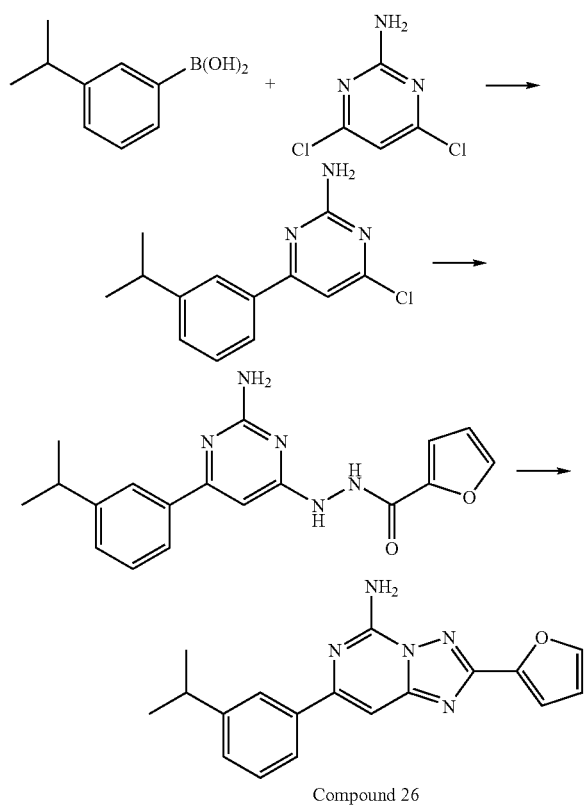

Compound 26

STEP 1: A mixture of 2-amino-4,6-dichloro-pyrimidine (0.50 g, 3.048 mmol), 3-isopropylbenzeneboronic acid (0.30 g, 1.572 mmol), Pd(PPh$_3$)$_4$ (0.09 g, 0.076 mmol), and 4–10 equivalents of sodium carbonate was heated in a solvent system of 1/1//acetonitrile/water (15 mL) at 90° C. for a period of 4 h. The reaction mixture was cooled to room temperature. The mixture was extracted with EtOAc and water. The organic portion was collected, dried over sodium sulfate, filtered, and concentrated in vacuo. The residue was purified by silica gel chromatography to produce a solid. Mass spectrum (ESI) 248.0, $^1$H NMR (CDCl$_3$) δ 1.30(d, 6H), 2.98(m, 1H), 5.93(br s, 2H), 7.03(s, 1H), 7.39(m, 2H), 7.73(d, 1H), 7.82(s, 1H).

STEP 2: The product of Step 1 (0.39 g, 1.57 mmol) and 2-furoic hydrazide (0.30 g, 2.36 mmol) in butanol (10 mL) were heated at 120° C. for 5 h. The reaction mixture was cooled to room temperature, and then extracted with ethyl acetate and water. The ethyl acetate layer was collected, dried over sodium sulfate, filtered, and concentrated in vacuo. The residue was purified on silica gel chromatography to produce a solid. Mass spectrum (ESI): 338.1, $^1$H NMR (CDCl$_3$) δ 1.22(d, 6H), 2.89(m, 1H), 5.42(br s, 1H), 6.34(s, 1H), 6.45(br s, 2H), 7.18(d, 1H), 7.23(m, 2H), 7.44(s, 1H), 7.53(d, 1H), 7.67(s, 1H).

STEP 3: The product of Step 2 (0.27 g, 0.80 mmol) was heated in N,O-bis(trimethylsilyl)acetamide (10 mL, 40.4 mmol) at 120° C. overnight. The reaction mixture was cooled, and then poured on ice water and stirred for 4 h. The mixture was extracted with ethyl acetate, dried over sodium sulfate, filtered, and concentrated in vacuo. The residue was purified on silica gel chromatography to produce a solid. Mass spectrum (ESI): 320.0, $^1$H NMR (CDCl$_3$) δ 1.21 (d, 6H), 2.89(m, 1H), 5.42 (br s, 2H), 6.60(m, 1H), 7.33(d, 1H), 7.41 (d, 1H), 7.43 (s, 1H), 7.64(s, 1H).

The compounds below were prepared in a similar fashion:

| COMPOUND NUMBER | STRUCTURE | M + 1 (ESI) |
|---|---|---|
| 27 | 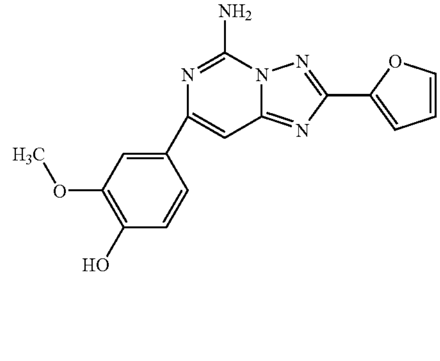 | 324.1 |

-continued

| COMPOUND NUMBER | STRUCTURE | M + 1 (ESI) |
| --- | --- | --- |
| 28 | 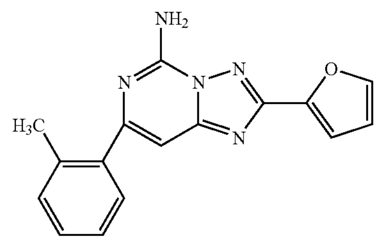 | 292.0 |
| 29 | 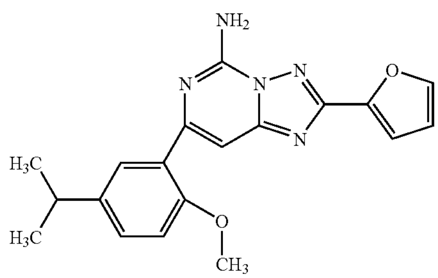 | 350.1 |
| 30 | 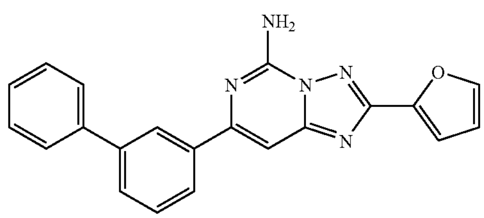 | 354.1 |
| 31 | 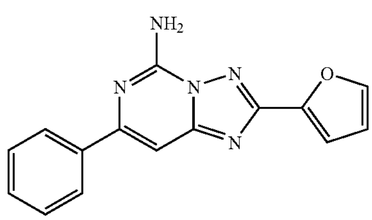 | 278.1' |
| 32 | 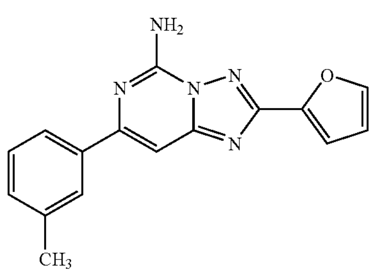 | 292.1 |
| 33 | 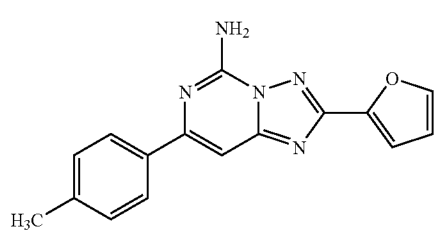 | 292.1 |

-continued

| COMPOUND NUMBER | STRUCTURE | M + 1 (ESI) |
|---|---|---|
| 34 | 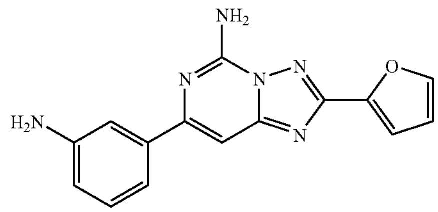 | 293.1 |
| 35 | 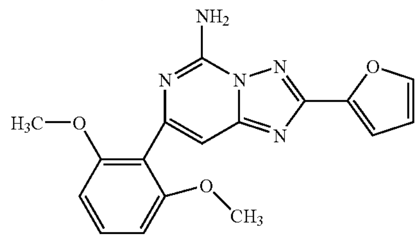 | 338.1 |
| 36 | 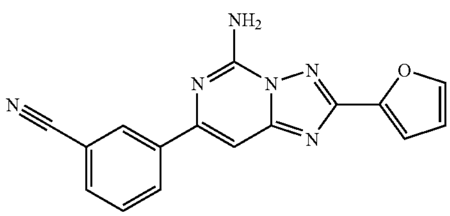 | 303.1 |
| 37 | 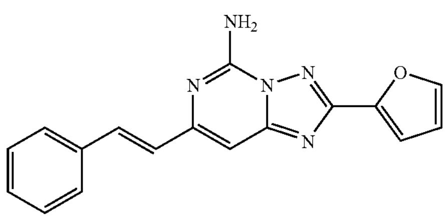 | 304.0 |
| 38 | 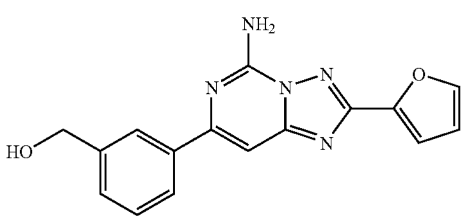 | 308.1 |

Example 5

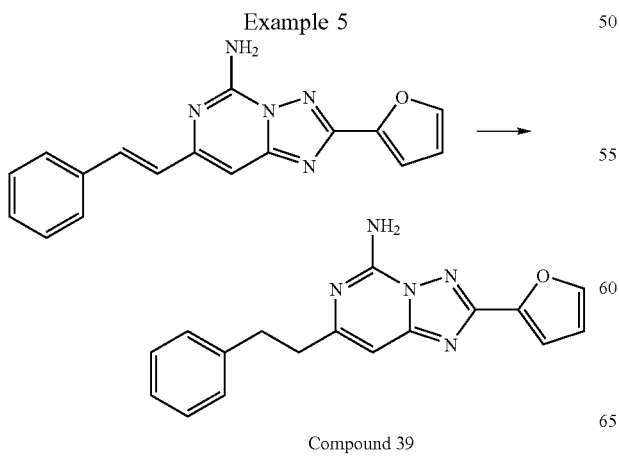

Compound 39

Compound 37 of Example 4 (15 mg, 0.0165 mmol) was stirred with 10% palladium on carbon (5 mg) in 10 mL of a solvent mixture (9:1:EtOAc/EtOH) under atmospheric hydrogen at room temperature for a period of 3 h. The mixture was passed through a pad of diatomaceous earth and the organic portion was concentrated in vacuo. The residue was purified by silica gel chromatography to afford a solid. Mass spectrum (ESI): 306.0, $^1$H NMR (CDCl$_3$) δ 2.97(t, 2H), 3.06(t, 2H), 5.97(br s, 2H), 6.58(m, 1H), 6.79(s, 1H), 7.20(m, 2H), 7.28(m, 4H), 7.68(m, 1H).

Example 6

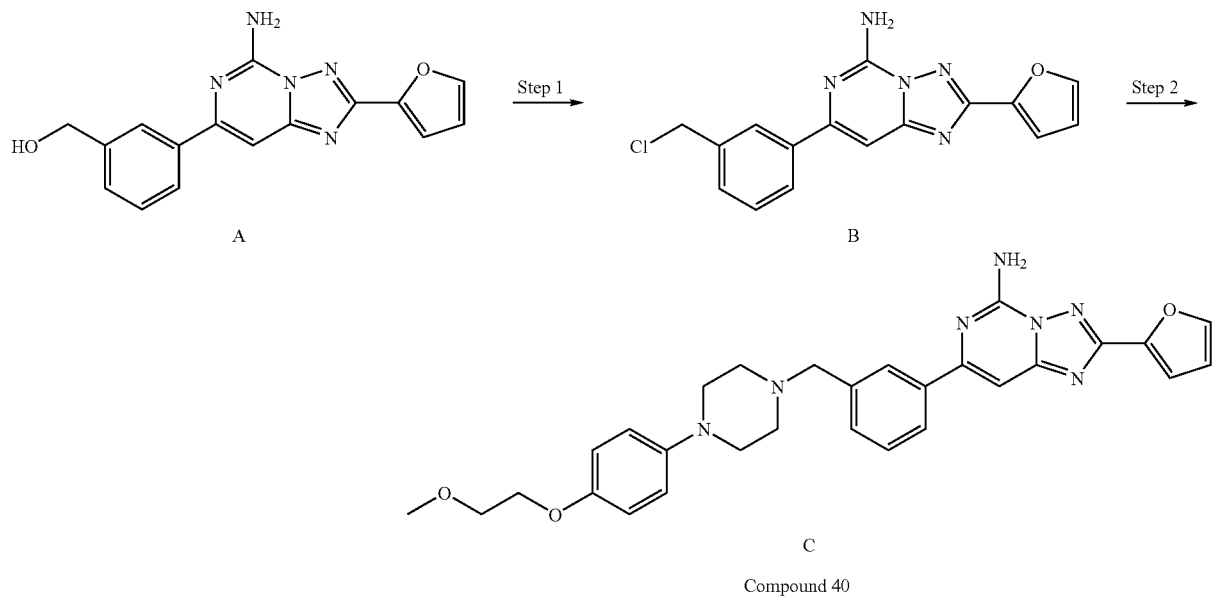

Compound 40

STEP 1: Compound 38 of Example 4 (0.60 g, 1.95 mmol) was combined with triethylamine (1.63 mL, 11.63 mmol) and thionyl chloride (0.71 g, 9.76 mmol) at 0° C. under a nitrogen atmosphere for 3 h. The reaction mixture was concentrated in vacuo and the residue B was then purified by silica gel chromatography. Mass spectrum (ESI): 326.1.

STEP 2: The product of step 1 (0.22 g, 0.66 mmol) was combined with 1-(4-methoxyethoxyphenyl)piperazine (0.31 g, 1.32 mmol) in dimethylformamide (2.0 mL) in a sealed tube and heated at 110° C. overnight. The reaction mixture was cooled and extracted with ethyl acetate and brine. The ethyl acetate layer was collected, dried over sodium sulfate, filtered, and concentrated in vacuo. The residue C was purified on silica gel chromatography. Mass spectrum (ESI): 526.1, $^1$H NMR (CDCl$_3$) δ 8.0 (S, 1H), 7.86 (m, 1H), 7.62 (dd, 1H), 7.41–7.45 (m, 3H), 7.24 (d, 1H), 6.82–6.85 (m, 4H), 6.58 (dd, 1H), 6.28 (br. s, 2H), 4.06 (t, 2H), 3.72 (t, 2H), 3.66 (s, 2H), 3.43 (S, 3H), 3.00–3.12 (m, 4H), 2.65–2.67(m, 4H).

The compounds below were prepared in a similar fashion:

| COMPOUND NUMBER | STRUCTURE | M + 1 (ESI) |
| --- | --- | --- |
| 41 | 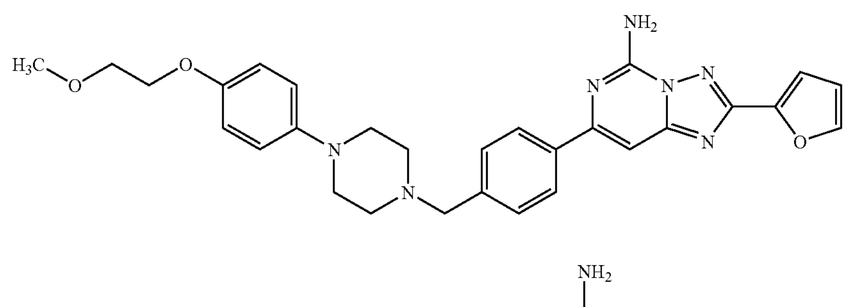 | 526.1 |
| 42 | 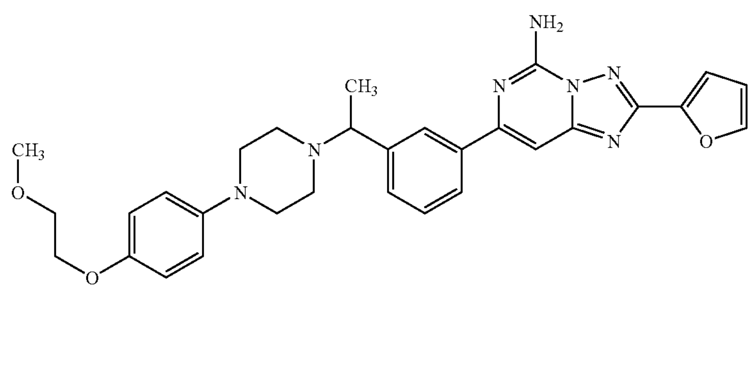 | 540.1 |

-continued

| COMPOUND NUMBER | STRUCTURE | M + 1 (ESI) |
|---|---|---|
| 43 | 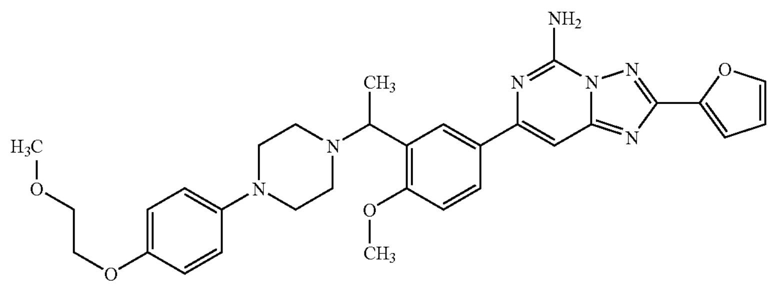 | 556.1 |
| 44 | 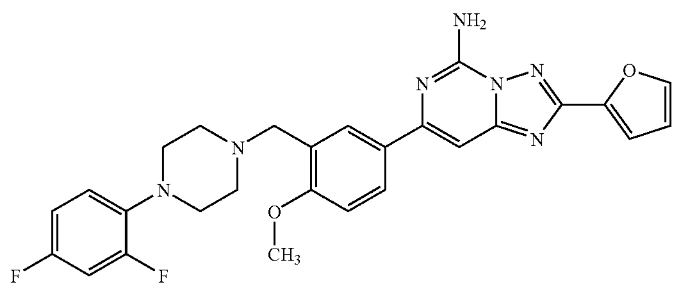 | 518.1 |
| 45 | 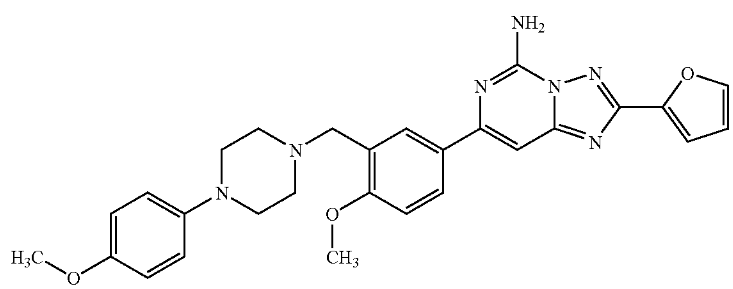 | 512.1 |
| 46 | 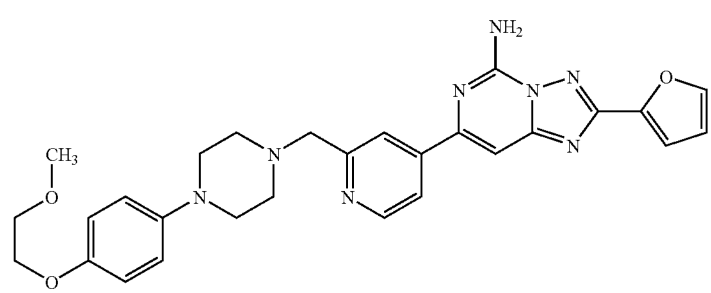 | 527.1 |
| 47 | 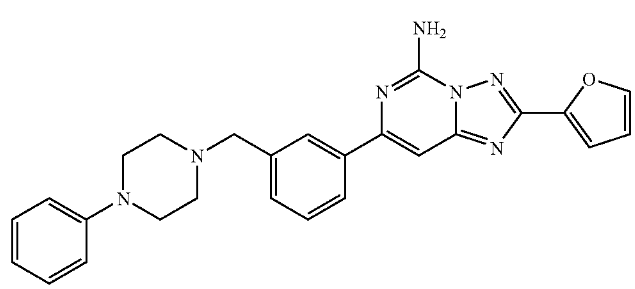 | 452.1 |

-continued
| COMPOUND NUMBER | STRUCTURE | M + 1 (ESI) |
|---|---|---|
| 48 | 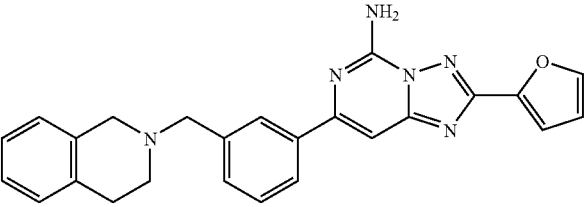 | 423.1 |
| 49 | 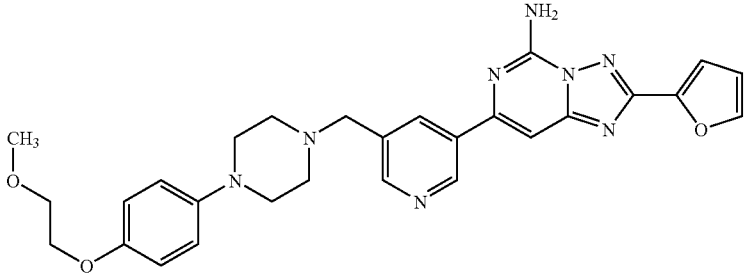 | 527.1 |
| 50 | 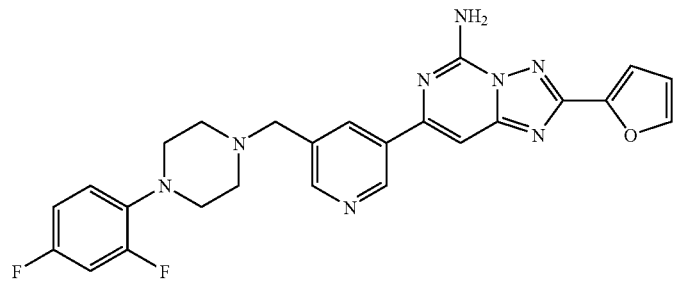 | 489.1 |
| 51 | 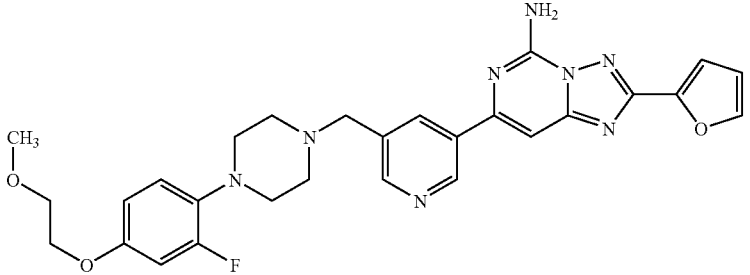 | 545.1 |
| 52 | 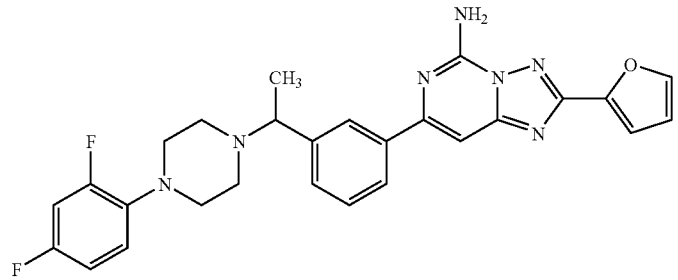 | 502.1 |

-continued
| COMPOUND NUMBER | STRUCTURE | M + 1 (ESI) |
|---|---|---|
| 53 | 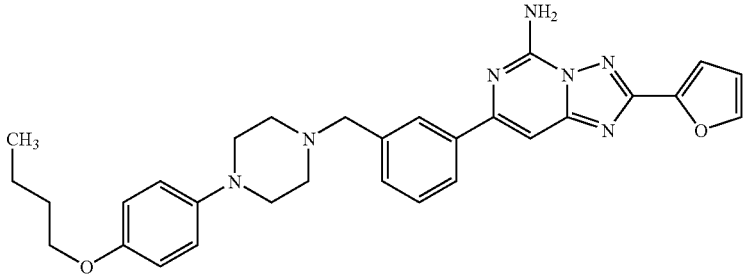 | 524.1 |
| 54 | 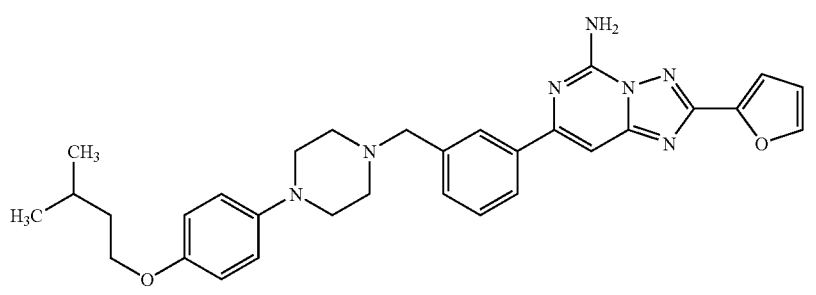 | 538.1 |
| 55 | 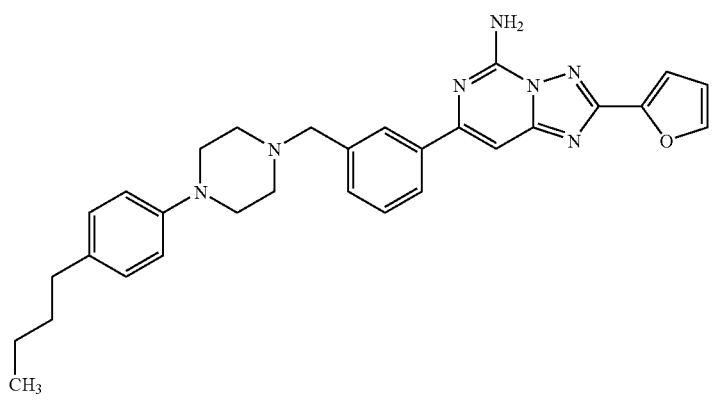 | 508.1 |
| 56 | 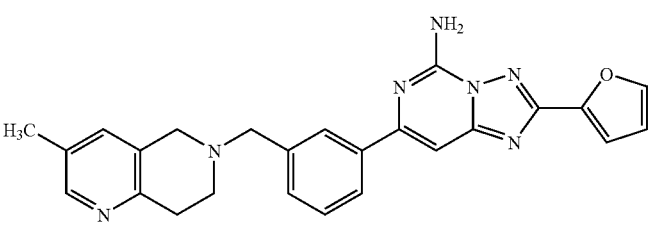 | 438.1 |
| 57 | 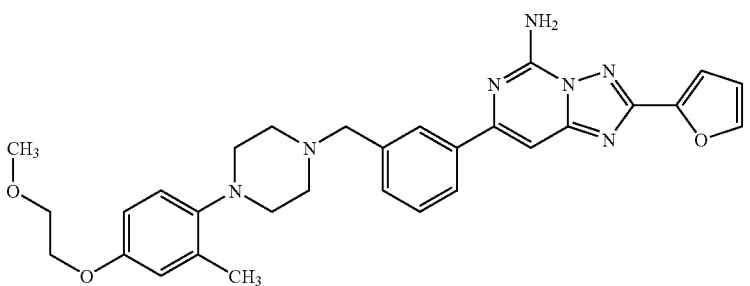 | 540.1 |

-continued
| COMPOUND NUMBER | STRUCTURE | M + 1 (ESI) |
|---|---|---|
| 58 | 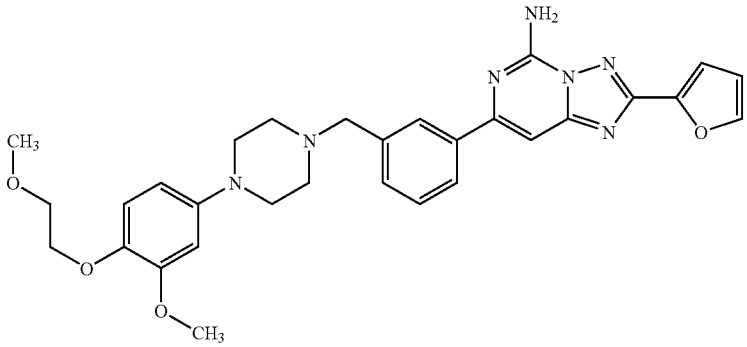 | 556.1 |
| 59 | 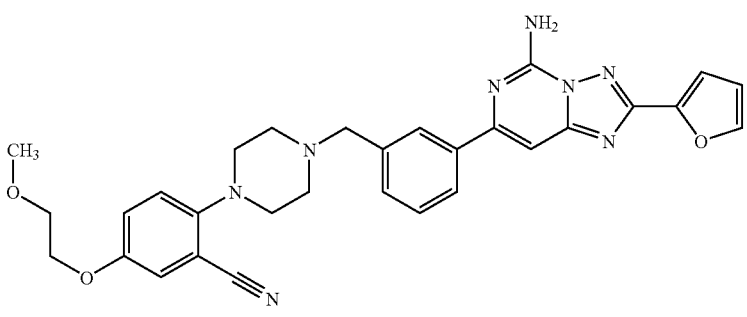 | 551.1 |
| 60 | 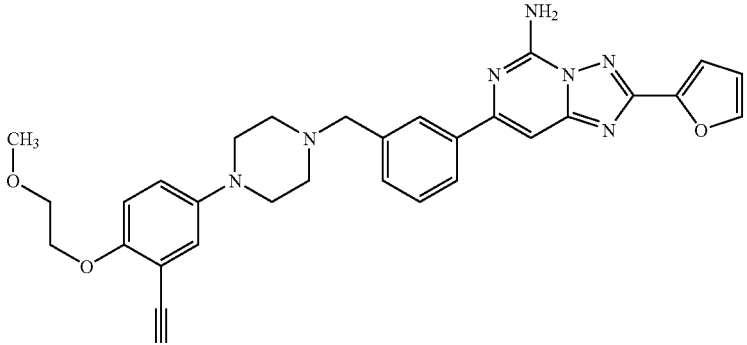 | 551.1 |
| 61 | 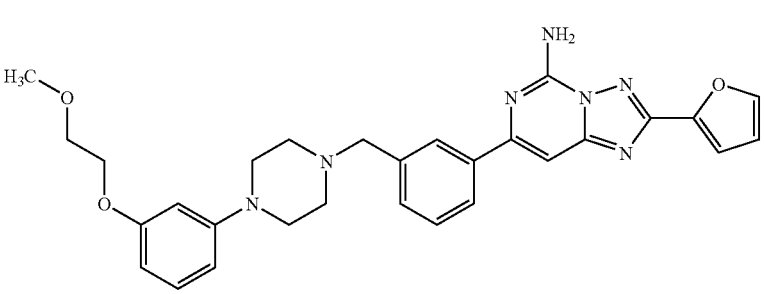 | 526.1 |

-continued

| COMPOUND NUMBER | STRUCTURE | M + 1 (ESI) |
| --- | --- | --- |
| 62 | 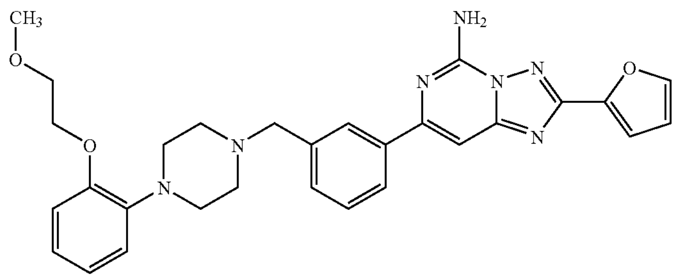 | 526.1 |
| 63 | 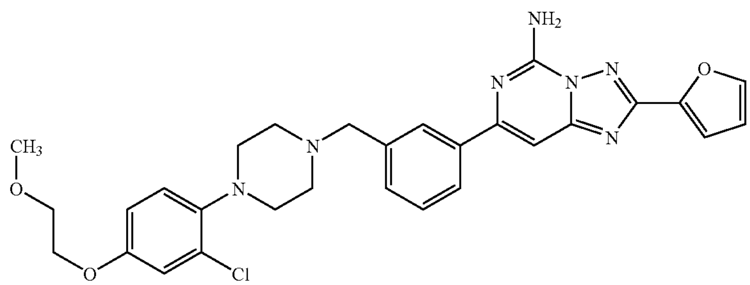 | 560.1 |
| 64 | 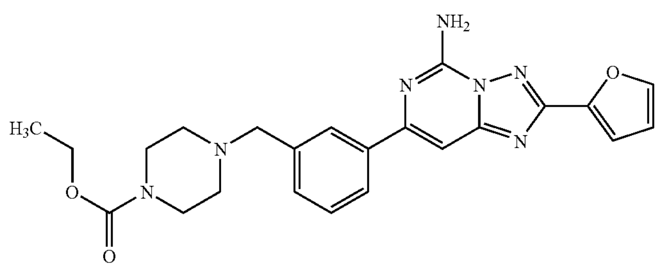 | 448.1 |
| 65 | 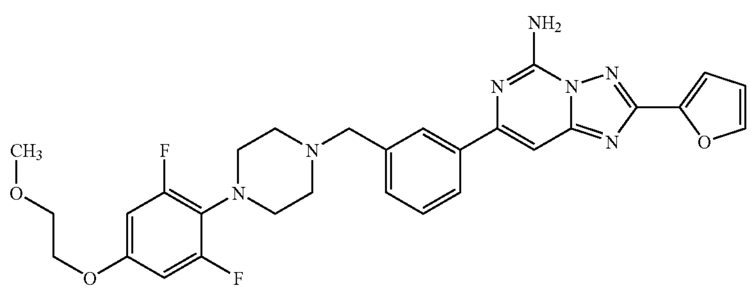 | 562.1 |
| 66 | 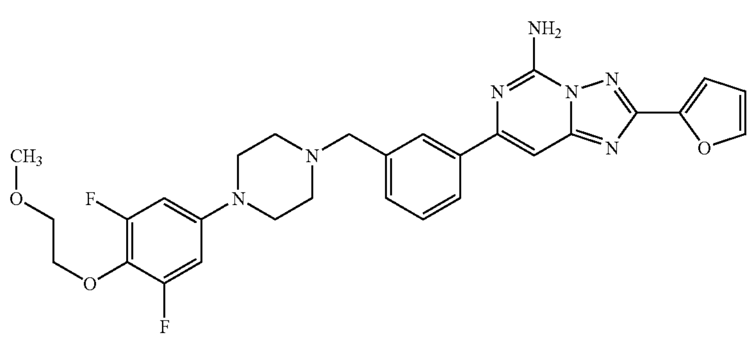 | 562.1 |

Example 7

Compound 77

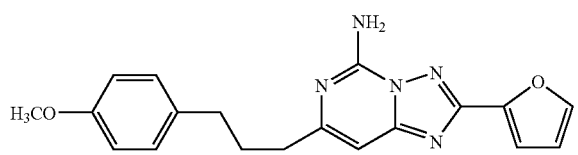

Step 1: To 4-(4-methoxyphenyl)butyric acid (2.00 g, 10.3 mmol) in CH$_2$Cl$_2$ (10 mL) add SOCl$_2$ (3.56 g, 30 mmol). Stir 3 h and concentrate. Add 2,2-dimethyl-1,3-dioxan-4,6-dione (1.78 g, 12.4 mmol), pyridine (2.37 g, 31 mmol) and CH$_2$Cl$_2$ (10 mL). Stir 18 h, add EtOH (10 mL), and heat at reflux 5 h. Add water, extract with EtOAc and chromatograph to obtain the ketone as an oil.

Step 2: Combine the product of Step 1 (0.366 g, 1.39 mmol) and guanidine carbonate (0.382 g, 2.12 mmol) in EtOH (3 mL). Heat at reflux 18 h. Add water (20 mL), cool in ice, and filter. Dry, wash with hexane and filter to obtain the pyrimidine as a solid.

Step 3: Add the product of Step 2 (0.15 g, 0.58 mmol) to POCl$_3$ (1.22 mL). Heat at reflux 1 h, concentrate, treat with ice, neutralize with NH$_3$, and extract with EtOAc. Purify on PLC to obtain the chloropyrimidine as a solid.

Step 4: Combine the product of Step 3, 2-furoic hydrazide and 1.0N HCl in EtOH. Heat in a sealed tube at 90° C. for 16 h. Basify with NH$_3$, extract with EtOAc, and purify on PLC to obtain the hydrazide as a solid.

Step 5: Add the product of Step 4 to BSA. Heat at 120° C. 18 h. Pour into CH$_3$OH, concentrate, and purify on PLC to obtain the title compound as a solid, Mass Spectrum (ESI): 350

Example 8

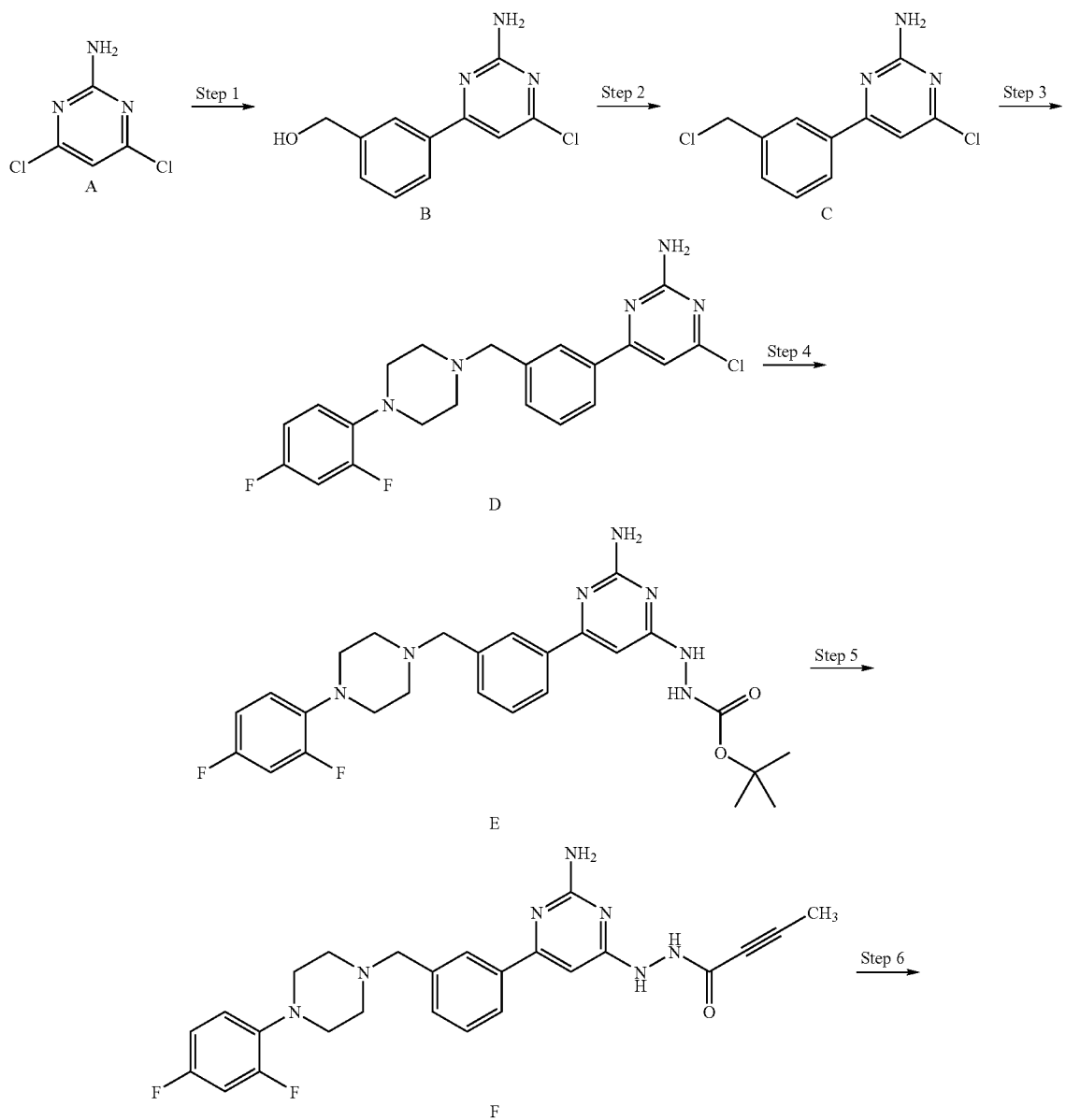

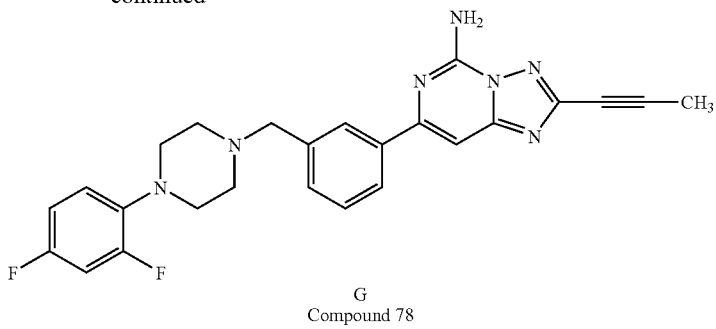

Compound 78

STEP 1: The product B was synthesized in a similar manner as described in Example 4, Step 1. Mass Spectrum (ESI): 236.1.

STEP 2: To a solution of the product from Step 1 B (2.25 g, 9.53 mmol) in dichloromethane (100 mL) stirred under an inert atmosphere at 0° C., triethylamine (8.00 mL, 57.18 mmol) was added followed by thionyl chloride (3.50 mL, 47.65 mmol) and the mixture was stirred an additional 1 h. The mixture was warmed to room temperature and then extracted with dichloromethane and brine. The organic portion was collected, dried over sodium sulfate, filtered, and concentrated in vacuo. The residue was purified by silica gel chromatography to afford the product C. Mass Spectrum (ESI): 255.1.

STEP 3: A solution of the product from Step 2 C (0.50 g, 1.97 mmol), 1-(2,4-difluorophenyl)-piperizine (0.39 g, 1.97 mmol), potassium iodide (0.33 g, 1.97 mmol), and potassium carbonate (0.82 g, 5.90 mmol) in acetonitrile (10 mL) was stirred under an inert atmosphere at 60° C. overnight. The mixture was cooled to room temperature and then extracted with ethyl acetate and brine. The organic portion was collected, dried over sodium sulfate, filtered, and concentrated in vacuo. The residue was purified by silica gel chromatography to afford the product D. Mass Spectrum (ESI): 416.1.

STEP 4: A solution of the product from Step 3 D (0.84 g, 1.97 mmol), and Boc-protected hydrazine (0.31 g, 2.37 mmol) in DMF was stirred under an inert atmosphere at 80° C. overnight. The mixture was cooled to room temperature and then extracted with ethyl acetate and brine. The organic portion was collected, dried over sodium sulfate, filtered, and concentrated in vacuo. The residue was purified by silica gel chromatography to afford the product E. Mass Spectrum (ESI): 512.1.

STEP 5: To a solution of the product from Step 4 E (0.15 g, 0.29 mmol) in dichloromethane (5 mL) stirred at room temperature, trifluroacetic acid (5 mL) was added and the reaction mixture was stirred an additional 1 h. The reaction mixture was concentrated in vacuo and taken up in DMF (2 mL). To this solution, butynoic acid was added (30 mg, 0.35 mmol), EDCl (68 mg, 0.35 mmol), HOBT (48 mg, 0.35 mmol), NMM (41 μL, 0.35 mmol) and stirred under an inert atmosphere at room temperature overnight. The mixture was extracted with ethyl acetate and brine. The organic portion was collected, dried over sodium sulfate, filtered, and concentrated in vacuo. The residue was purified by silca gel chromatography to afford the product F. Mass Spectrum (ESI): 478.1

STEP 6: The product of Step 5 F (45 mg, 0.09 mmol) was heated in N,O-bis(trimethylsilyl)acetamide (2 mL) at 120° C. overnight. The reaction mixture was cooled, poured onto ice water and stirred for 4 h. The mixture was extracted with ethyl acetate, dried over sodium sulfate, filtered, and concentrated in vacuo. The residue was purified on silica gel chromatography to produce a solid G. Mass spectrum (ESI): 460.1, $^1$H NMR (CDCl$_3$) δ 7.98 (s, 1H), 7.88 (m, 1H), 7.45 (m, 2H), 7.39 (s, 1H), 6.90 (m, 1H), 6.79 (m, 2H), 5.97 (br s, 2H), 3.66 (s, 2H), 3.06 (t, 4H), 2.67 (t, 4H), 2.15 (s, 3H).

Example 9

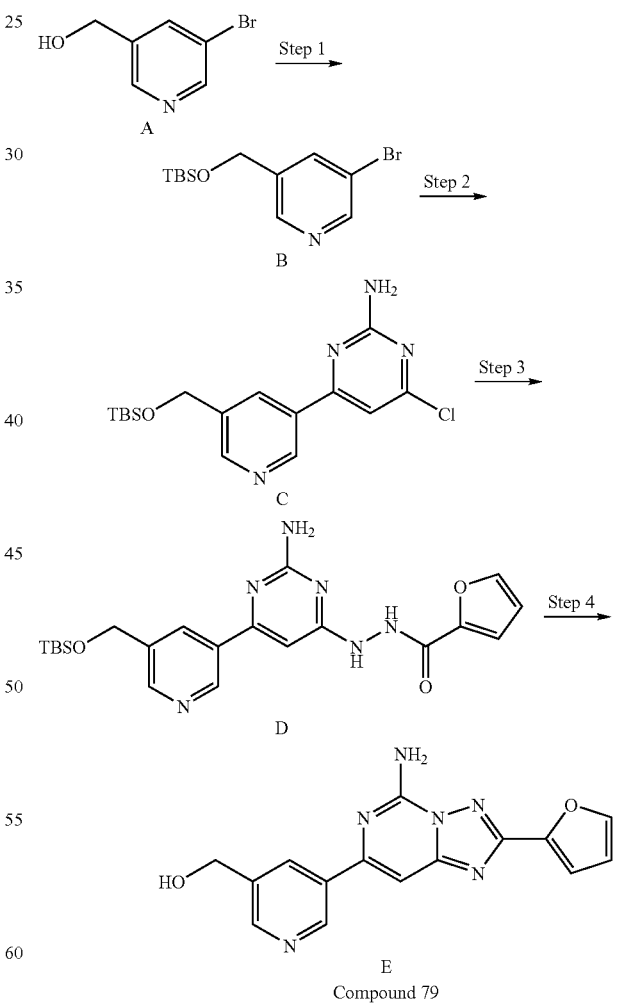

Compound 79

STEP 1: A solution of 5-bromo-3-(methanol)-pyridine (6.69 g, 35.58 mmol), t-butyldimethylsilyl chloride (4.71 g, 46.26 mmol), and imidazole (7.25 g, 106.74 mmol), in dichloromethane (250 mL) was stirred at room temperature for 3 h. The mixture was extracted with dichloromethane and brine. The organic portion was collected, dried over sodium sulfate, filtered, and concentrated in vacuo. The residue was purified by silca gel chromatography to afford the product B. Mass Spectrum (ESI): 304.1, 302.1

STEP 2: To a stirred solution of the product from Step 1 B (7.35 g, 24.32 mmol) in diethyl ether (125 mL) under an inert atmosphere at −78° C., a 2.5N solution of n-butyl lithium in hexanes (14.51 mL) was added dropwise. After stirring 10 minutes, triisopropyl borate (11.02 mL, 47.75 mmol) was added and the solution was warmed to room temperature and stirred for an additional 1 h. The reaction was quenched with water. The reaction mixture was concentrated in vacuo and the resulting solid intermediate was used in the next step without further purification.

The solid intermediate (6.50 g, 27.99 mmol) was taken up in dimethoxyethylene (100 mL), and 2-amino-4,6-dichloropyrimidine (9.18 g, 55.98 mmol), sodium carbonate (10.31 g, 97.26 mmol), and tetrakis(triphenylphosphine) palladium (1.40 g, 1.21 mmol) were added. The mixture was heated at 90° C. for 4 h. The reaction mixture was cooled and extracted with ethyl acetate and brine. The ethyl acetate layer was collected, dried over sodium sulfate, filtered, and concentrated in vacuo. The residue C was purified on silica gel chromatography. Mass Spectrum (ESI): 351.1

STEP 3: A solution of the product from Step 2 C (1.64 g, 4.67 mmol) and 2-furoic hydrazide (0.92 g, 7.01 mmol) in 10 mL of n-butanol was heated at 90° C. overnight. The mixture was cooled to room temperature, extracted with ethyl acetate, and washed with brine. The organic portion was collected, dried over sodium sulfate, filtered and concentrated in vacuo. The residue D was used in the next step without further purification. Mass spectrum (ESI): 441.1.

STEP 4: The product of Step 3 D (2.04 g, 4.63 mmol) was heated in N,O-bis(trimethylsilyl)acetamide (15 mL) at 120° C. overnight. The reaction mixture was cooled, poured on ice water and stirred for 4 h. The mixture was extracted with ethyl acetate, dried over sodium sulfate, filtered, and concentrated in vacuo. The residue was purified on silica gel chromatography to produce a solid E. Mass spectrum (ESI): 309.1, $^1$H NMR (CDCl$_3$) δ 9.19 (s, 1H), 8.59 (s, 2H), 8.53 (s, 1H), 7.76 (s, 1H), 7.52 (s, 1H), 6.66 (m, 1H), 4.76 (s, 2H).

The following compounds were prepared in a similar fashion.

| Compound | Structure | M + 1 (ESI) |
|---|---|---|
| 80 | (structure: aminopyridylmethanol-triazolopyrimidine-furan) | 309.1 |
| 81 | (structure: hydroxyethylphenyl-triazolopyrimidine-furan) | 322.1 |

Example 10

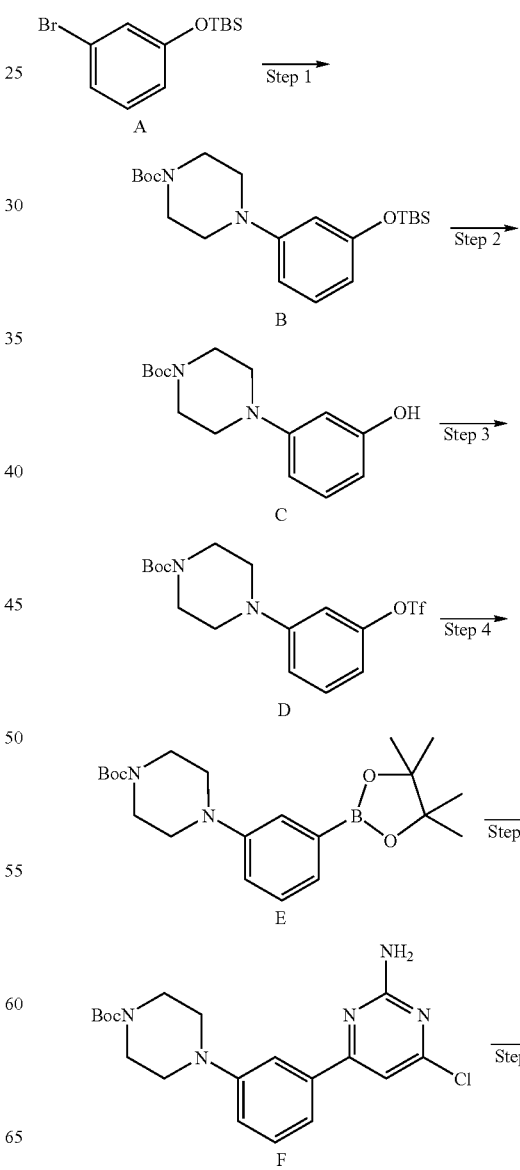

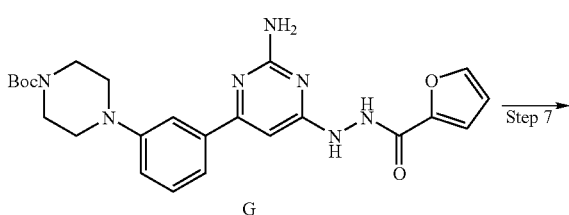

G

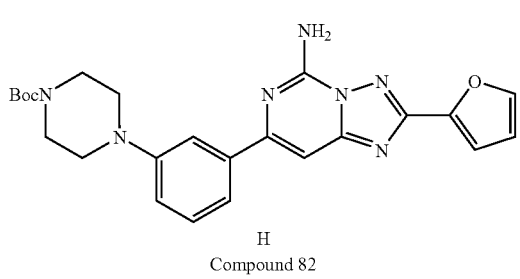

H
Compound 82

Step 1: A mixture of bromide (7.0 g, 24.37 mmol), N-Boc piperazine (5.45 g, 29.24 mmol), palladium acetate (0.22 g, 0.97 mmol), tris(tert-butyl)phosphine (0.79 g, 3.9 mmol) and sodium tert-butoxide (3.28 g, 34.12 mmol) in toluene (50 mL) was heated at reflux for 2 h under a nitrogen atmosphere, cooled to room temperature and then diluted with water. The resultant mixture was extracted by ethyl acetate, dried by sodium sulfate and filtered. This was evaporated under reduced pressure leaving a clean product B which was not purified for its use in Step 2. Mass spectrum (ESI), $M^{+1}$: 393.1, 337.1

Step 2: The compound from step 1 B was treated with tetrabutylammonium fluoride (48.74 g, 48.74 mmol of 1.0M solution in THF) in THF (100 mL) for 1 hr at room temperature, diluted with water, then extracted by ethyl acetate. The resultant ethyl acetate extract was dried with sodium sulfate and evaporated to give a phenol derivative C. Mass spectrum (ESI), $M^{+1}$: 279.0, 242.0.

Step 3: Triflic anhydride was added dropwise to a mixture of phenol from step 2 C and triethyl amine (3.74 mL, 26.81 mmol) in dichloromethane (100 mL) at 0° C. under $N_2$, stirred at this temperature for 1 h and then warmed to room temperature. Saturated sodium bicarbonate solution was added and extracted by dichloromethane. This was dried using sodium sulfate and adsorbed on a small amount of silica gel, transferred to a column and eluted using hexane/ethyl acetate (4:1) to provide the triflate D. Mass spectrum (ESI), $M^{+1}$: 411.1, 355.1.

Step 4: The compound from step 3 D was treated with bis(pinacolato)diboron in the presence of $PdCl_2$(dppf), dppf, and potassium acetate in 1,4-dioxane (90 mL) at 80° C. under $N_2$ overnight, cooled to room temperature, washed with brine, dried with sodium sulfate and evaporated. The residue was purified by column chromatography on silica gel to give the product E. Mass spectrum (ESI), $M^{+1}$: 389.1

Step 5: The compound from step 4 E was treated with 2-amino-4,6-dichloro-pyrimidine as in step 1, example 4, to form compound F. Mass spectrum (ESI), $M^{+1}$: 390.1

Step 6: The same procedure as step 2 of example 4 was performed to form compound G. Mass spectrum (ESI), $M^{+1}$: 480.1

Step 7: The same procedure as step 3 of example 4 was performed to form compound H. $^1$H NMR (CDCl$_3$) δ 7.61(m, 2H), 7.43(d, 1H), 7.38(m, 2H), 7.12 (m, 1H), 7.02 (dd, 1H), 6.60 (dd, 1H), 6.02(br. s, 2H), 3.62 (m, 4H), 3.21 (m, 4H), 1.50 (s, 9H). Mass spectrum (ESI), $M^{+1}$: 462.1

The following compounds were prepared in a similar fashion:

| COMPOUND | STRUCTURE | M + 1 (ESI) |
|---|---|---|
| 83 | [structure] | 434.1 |
| 84 | [structure] | 419.1 |

-continued

| COMPOUND | STRUCTURE | M + 1 (ESI) |
| --- | --- | --- |
| 85 | 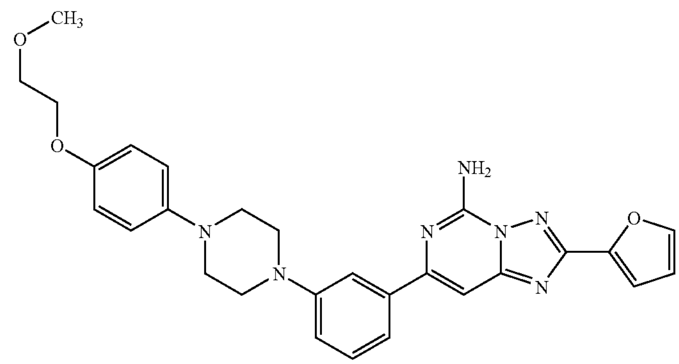 | 512.1 |
| 86 | 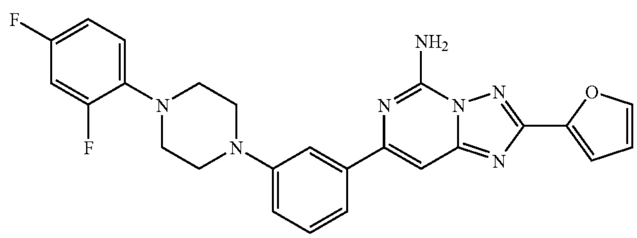 | 474.1 |
| 88 | 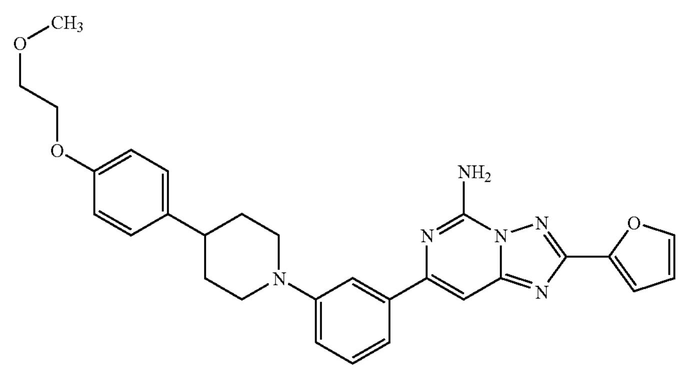 | 511.1 |
| 89 | 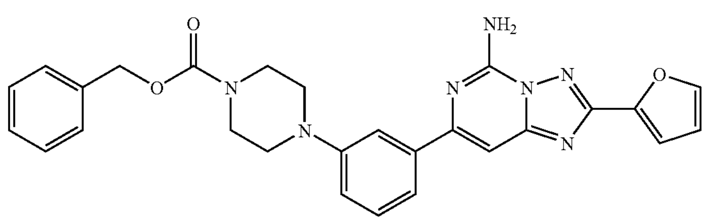 | 496.1 |
| 90 | 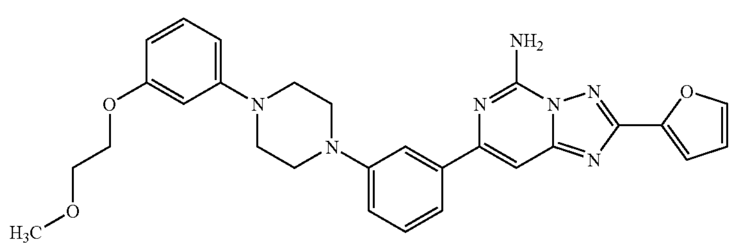 | 512.1 |

| COMPOUND | STRUCTURE | M + 1 (ESI) |
|---|---|---|
| 91 | 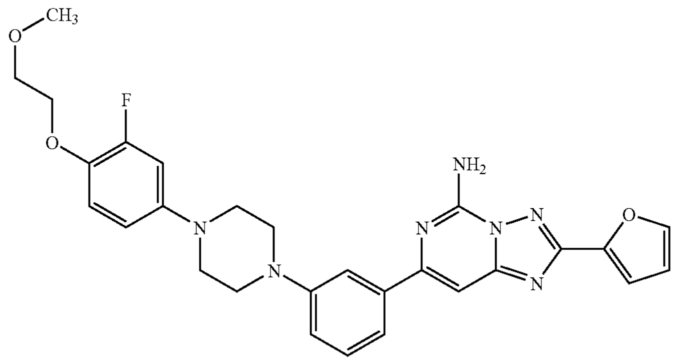 | 530.1 |

Example 11

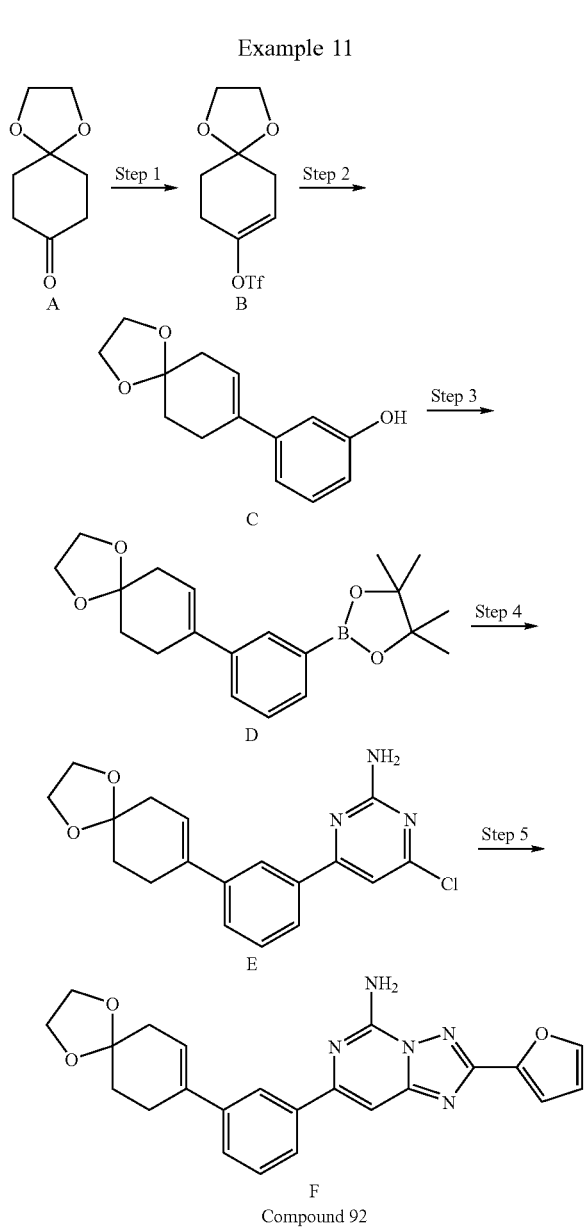

STEP 1: The protected enol triflate B was prepared by an adapted literature procedure (Synthesis, p. 993, 1991). ¹H NMR (CDCl₃) δ 5.66 (t, 1H), 3.99 (s, 4H), 2.54 (m, 2H), 2.41 (m, 2H), 1.90 (t, 2H).

STEP 2: The product of Step 1 B (5.70 g, 19.79 mmol), 3-hydroxyphenyl boronic acid (6.10 g, 27.71 mmol), lithium chloride (2.50 g, 58.98 mmol), a 2N aqueous sodium carbonate solution (27.70 mL), and tetrakis(triphenylphosphine) palladium (1.14 g, 0.98 mmol) in 100 mL of dimethoxyethane was heated at reflux temperature for 2 h. The mixture was cooled to room temperature and concentrated in vacuo. The residue was diluted with dichloromethane and washed with 100 mL of a mixture of 6% ammonium hydroxide in 2 N sodium carbonate solution. The aqueous portion was extracted with an additional 100 mL of dichloromethane. The combined organic portions were dried over sodium sulfate, filtered, and concentrated in vacuo. The residue was purified by silica gel chromatography to afford the product C. ¹H NMR (CDCl₃) δ 7.16 (t, 1H), 6.97 (d, 1H), 6.85 (t, 1H), 6.69 (dd, 1H), 5.98 (m, 1H), 4.77 (s, 1H), 4.02 (s, 4H), 2.63 (m, 2H), 2.46 (m, 2H), 1.92 (t, 2H).

STEP 3: To a solution of the product from Step 2 C (2.20 g, 9.48 mmol) in dichloromethane (60 mL) at 0° C. under an inert atmosphere, was added triethylamine (1.45 mL, 10.43 mmol) then trifluoromethanesulfonic anhydride (1.75 mL, 10.43 mmol). The mixture was stirred warmed to room temperature and stirred an additional 2 h. The mixture was extracted with water. The organic portion was collected, dried over sodium sulfate, filtered and concentrated in vacuo. The residue (1.36 g, 3.74 mmol) was used without further purification and taken up in dioxane (80 mL). To this solution was added bis(pinacolato)diboron (1.14 g, 4.49 mmol), PdCl₂(dppf) (0.16 g, 0.22 mmol), dppf (0.12 g, 0.22 mmol), and potassium acetate (1.10 g, 11.22 mmol) and the mixture was heated to 80° C. under an inert atmosphere overnight. The mixture was cooled to room temperature and then extracted with ethyl acetate and brine. The organic portion was collected, dried over sodium sulfate, filtered, and concentrated in vacuo. The residue was purified by silca gel chromatography to afford the product D. Mass Spectrum (ESI): 343.1

STEP 4: A solution of the product of Step 3 D (0.64 g, 1.87 mmol), 2-amino-4,6-dichloropyrimidine (0.31 g, 1.87 mmol), sodium carbonate (0.79 g, 7.48 mmol), and tetrakis(triphenylphosphine) palladium (0.11 g, 0.09 mmol) in 60 mL of 1/1//acetonitrile/water was heated at 90° C. for 3 h. The reaction mixture was cooled and extracted with ethyl acetate and brine. The ethyl acetate layer was collected, dried over sodium sulfate, filtered, and concentrated in vacuo. The residue was purified on silica gel chromatography resulting in compound E. Mass Spectrum (ESI): 344.1

STEP 5: A solution of the product of Step 4 E (0.60 g, 1.75 mmol) and 2-furoic hydrizide (0.33 g, 2.62 mmol) in 15 mL of n-butanol was heated at 90° C. for 2 h. The mixture was cooled to room temperature and concentrated in vacuo. The residue was taken up in 5 mL of N,O-bis(trimethylsilyl)acetamide and heated to 120° C. under a nitrogen atmosphere for 3 h. The mixture was cooled, poured onto ice water, and then stirred 4 h. The mixture was extracted with ethyl acetate and brine, dried over sodium sulfate, filtered, and concentrated in vacuo. The residue was purified by silica gel chromatography to afford compound F. Mass Spectrum (ESI): 416.1. $^1$H NMR (DMSO-d$_6$) δ 8.10 (s, 1H), 7.92 (m, 2H), 7.87 (s, 1H), 7.51 (s, 1H), 7.38 (m, 1H), 7.15 (t, 1H), 6.03 (s, 1H), 3.86 (s, 1H), 4.02 (s, 4H), 255 (m, 2H), 2.33 (m, 2H), 1.77 (t, 2H).

Example 12

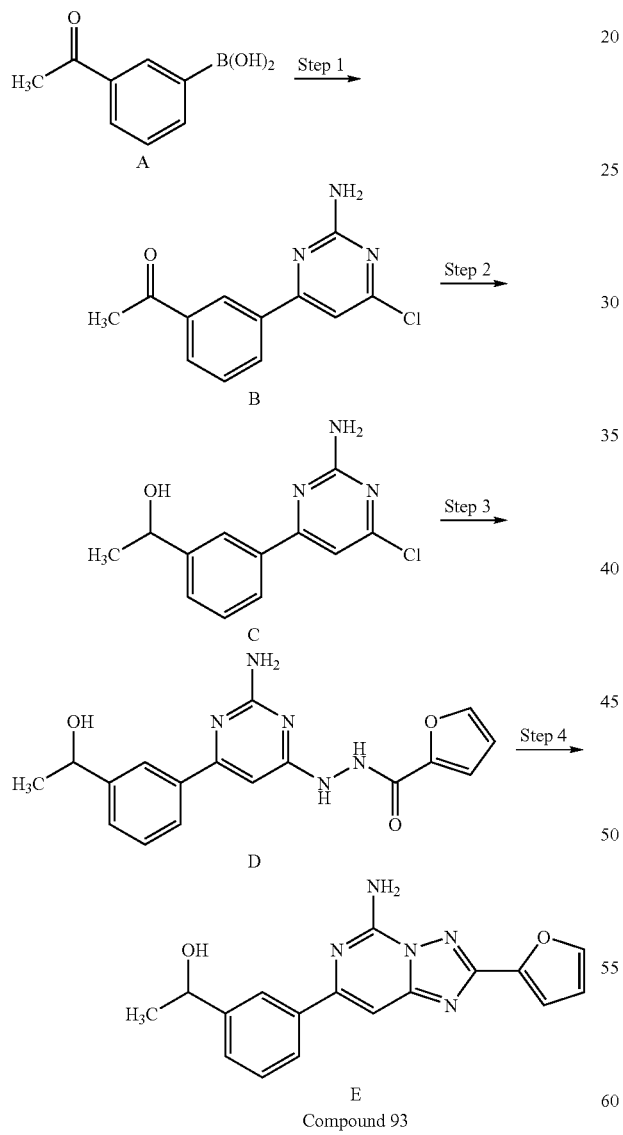

Compound 93

STEP 1: A solution of 3-acetylbenzene boronic acid (2.00 g, 12.20 mmol), 2-amino-4,6-dichloropyrimidine (4.00 g, 24.40 mmol), sodium carbonate (6.47 g, 61.00 mmol), and tetrakis(triphenylphosphine) palladium (0.70 g, 0.61 mmol) in 100 mL of 1/1//acetonitrile/water was heated at 90° C. for 3 h. The reaction mixture was cooled and extracted with ethyl acetate and brine. The ethyl acetate layer was collected, dried over sodium sulfate, filtered, and concentrated in vacuo. The residue was purified on silica gel chromatography to afford the product B. Mass Spectrum (ESI): 248.0

STEP 2: To a solution of the ketone product of Step 1 B (3.00 g, 12.11 mmol) in 75 mL of ethyl alcohol, was added sodium borohydride (0.92 g, 24.22 mmol) at 0° C. then warmed to room temperature and stirred for 1 h. The mixture was extracted with ethyl acetate, and washed with brine. The organic portion was collected, dried over sodium sulfate, filtered and concentrated in vacuo. The residue was purified by silica gel chromatography to afford the product C. Mass spectrum (ESI): 250.0.

STEP 3: A solution of the product C from Step 2 (0.27 g, 1.08 mmol) and 2-furoic hydrizide (0.33 g, 2.62 mmol) in 10 mL of n-butanol was heated at 90° C. overnight. The mixture was cooled to room temperature, extracted with ethyl acetate, and washed with brine. The organic portion was collected, dried over sodium sulfate, filtered and concentrated in vacuo. The residue D was used in the next step without further purification. Mass spectrum (ESI): 340.1.

STEP 4: The product from Step 3 D (0.37 mg, 1.08 mmol was taken up in 5 mL of N,O-bis(trimethylsilyl)acetamide and heated to 120° C. under a nitrogen atmosphere for 3 h. The mixture was cooled, poured onto ice water, and then stirred 4 h. The mixture was extracted with ethyl acetate and brine, dried over sodium sulfate, filtered, and concentrated in vacuo. The residue was purified by silica gel chromatography to afford the compound E. Mass Spectrum (ESI): 322.1. $^1$H NMR (CDCl$_3$) δ 8.05 (s, 1H), 7.86 (m, 1H), 7.64 (d, 1H), 7.47 (m, 2H), 7.41 (s, 1H), 7.25 (s, 1H), 6.60 (m, 1H), 6.05 (br s, 2H), 5.01 (m, 1H), 3.49 (d, 3H).

The following compound was prepared in a similar fashion:

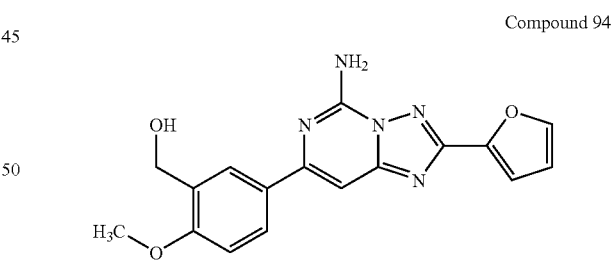

Compound 94

Example 13

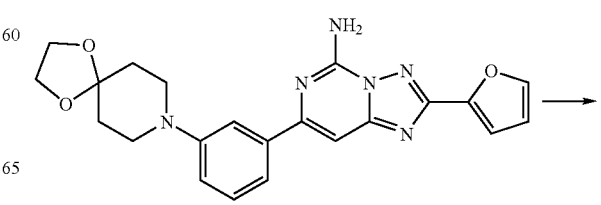

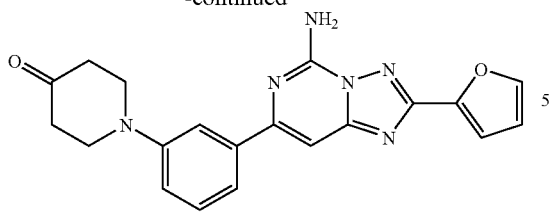

Compound 95

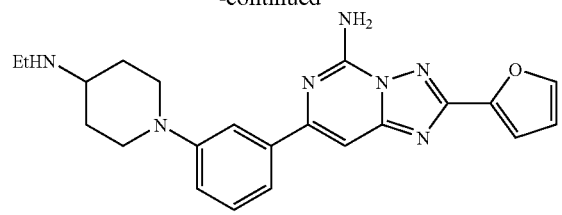

Compound 96

A mixture of the ketal product prepared in a similar manner as in Example 10, (113 mg, 0.27 mmol), 20 mL of a 5% HCl aq. solution, and 20 mL of acetone was heated at 100° C. overnight. The mixture was cooled to room temperature, extracted with ethyl acetate, and washed with water. The organic portion was collected, dried over sodium sulfate, filtered and concentrated in vacuo. The residue was purified by silica gel chromatography to afford the product. Mass spectrum (ESI): 375.1. $^1$H NMR (CDCl$_3$) δ 7.57 (d, 1H), 7.55 (t, 1H), 7.31 (m, 3H), 7.20 (d, 1H), 6.95 (dd, 1H), 6.65 (br s, 2H), 6.53 (m, 1H), 3.60 (t, 4H), 2.51 (t, 4H).

Example 14

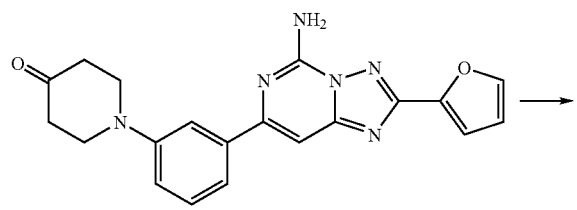

To a solution of the ketone product of example 13 (55 mg, 0.15 mmol), a 70% solution of ethylamine in water (0.01 mL, 0.16 mmol) in 5 mL of tetrahydrofuran, was added sodium triacetoxy borohydride (46 mg, 0.22 mmol) and stirred at room temperature for 2 h. The mixture was quenched with 3N aqueous sodium hydroxide solution, extracted with ethyl acetate, and washed with brine. The organic portion was collected, dried over sodium sulfate, filtered and concentrated in vacuo. The residue was purified by silica gel and chromatography to afford the product. Mass spectrum (ESI): 404.1. $^1$H NMR (CDCl$_3$) δ 7.63 (d, 1H), 7.60 (t, 1H), 7.40 (d, 2H), 7.34 (t, 1H), 7.03 (dd, 1H), 6.60 (m, 1H), 6.00 (br s, 2H), 3.77 (d of t, 2H), 2.85 (t of d, 2H), 2.74 (m, 2H), 2.03 (m, 2H), 1.55 (q of t, 3H), 1.15 (m, 4H).

The following compounds were prepared in a similar fashion.

| COMPOUND | STRUCTURE | M + 1 (ESI) |
|---|---|---|
| 97 | 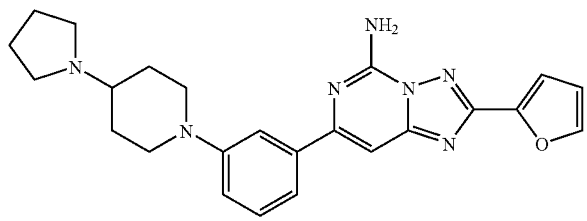 | 430.1 |
| 98. | 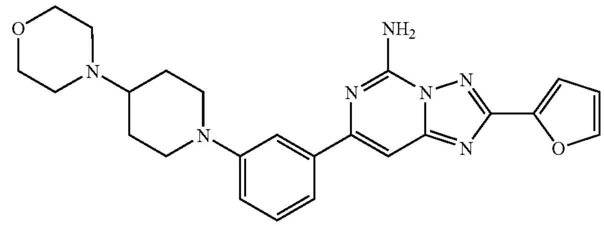 | 446.1 |
| 99 | 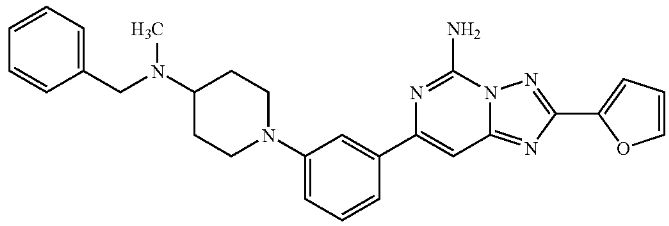 | 480.1 |

-continued
| COMPOUND | STRUCTURE | M + 1 (ESI) |
|---|---|---|
| 100 | 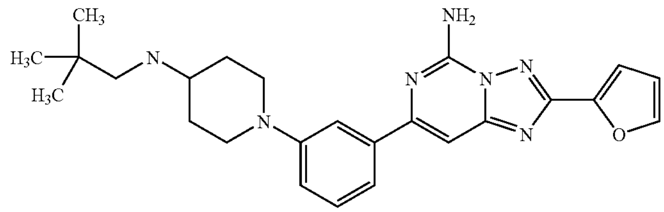 | 446.1 |
| 101 | 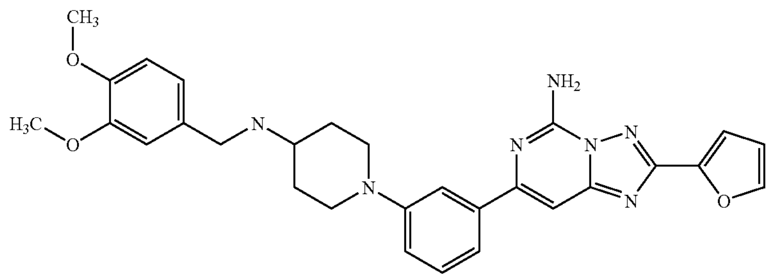 | 526.1 |
| 102 | 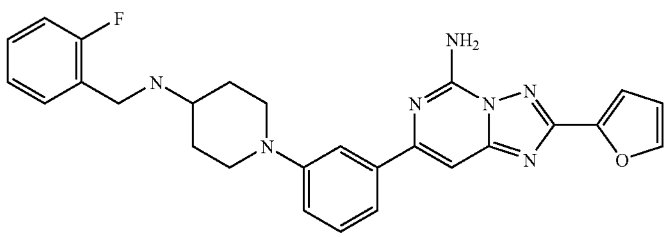 | 484.1 |
| 103 | 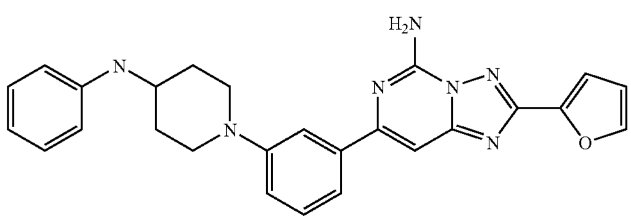 | 452.1 |
| 104 | 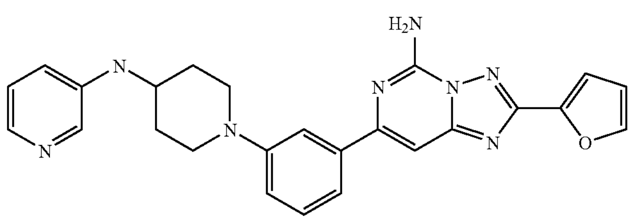 | 453.1 |
Example 15
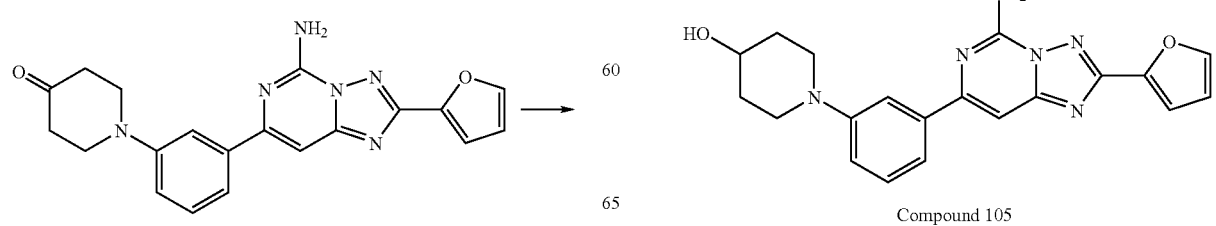
Compound 105

To a solution of the ketone product of example 13 (60 mg, 0.16 mmol) in 5 mL of ethyl alcohol, was added sodium borohydride (12 mg, 0.32 mmol). The mixture was stirred at room temperature for 1 h. The mixture was extracted with ethyl acetate, and washed with brine. The organic portion was collected, dried over sodium sulfate, filtered and concentrated in vacuo. The residue was purified by silica gel chromatography to afford the product. Mass spectrum (ESI): 377.1. $^1$H NMR (CDCl$_3$) δ 7.63 (s, 1H), 7.60 (t, 1H), 7.40 (m, 2H), 7.34 (t, 1H), 7.25 (m, 1H), 7.03 (d, 1H), 6.60 (m, 1H), 6.11 (brs, 2H), 3.88 (m, 2H), 3.65 (m, 2H), 3.01 (m, 2H), 2.04 (m, 2H), 1.17 (br s, 3H).

Example 16

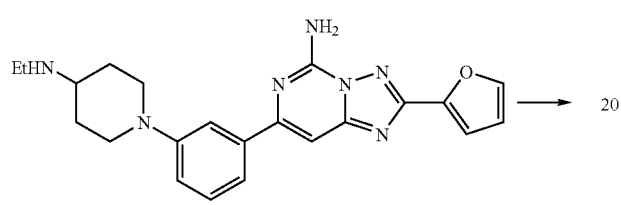

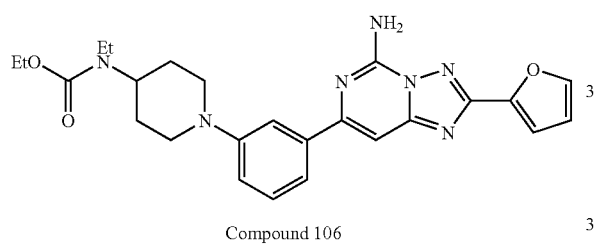

Compound 106

To a solution of the product of Example 14 (35 mg, 0.0868 mmol), diisopropylethylamine (0.02 mL, 0.0955 mmol) in 3 mL of DMF, was added ethyl chloroformate (0.01 mL, 0.0955 mmol). The mixture was stirred at room temperature for 3 h. The mixture was concentrated in vacuo and the residue was purified by silica gel chromatography to afford the product. Mass spectrum (ESI): 476.1. $^1$H NMR (CDCl$_3$) δ 7.61 (d, 1H), 7.58 (t, 1H), 7.39 (m, 2H), 7.33 (t, 1H), 7.22 (d, 1H), 7.00 (dd, 1H), 6.58 (m, 1H), 6.22 (br s, 2H), 4.15 (q, 3H), 3.82 (d, 2H), 3.46 (m, 4H), 3.01 (m, 2H), 2.05 (br s, 1H), 1.59 (br s, 1H), 1.26 (t, 3H), 1.12 (t, 3H). The following compound was prepared in a similar fashion using the acyl chloride.

Example 17

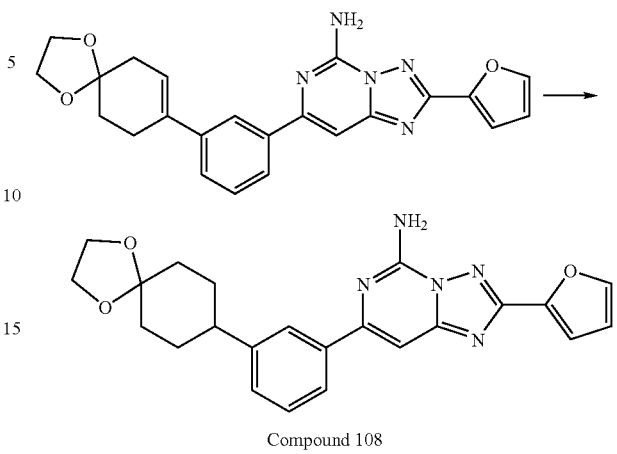

Compound 108

To a solution of the product of Example 11, Step 5 (80 mg, 0.15 mmol) in 5 mL of a solution of 9/1//ethanol/ethyl acetate, was added 10% palladium on carbon (160 mg). The mixture was shaken in a hydrogenation apparatus at room temperature under 40 psi for 1 h. The mixture was filtered over a celite pad and concentrated in vacuo. The residue was purified by silica gel chromatography to afford the product. Mass spectrum (ESI): 418.1. $^1$H NMR (CDCl$_3$) δ 7.90 (s, 1H), 7.77 (d, 1H), 7.63 (d, 1H), 7.48 (m, 2H), 7.40 (m, 1H), 6.59 (dd, 1H), 6.12 (brs, 2H), 4.00 (s, 4H), 1.67–1.96 (m, 9H).

Example 18

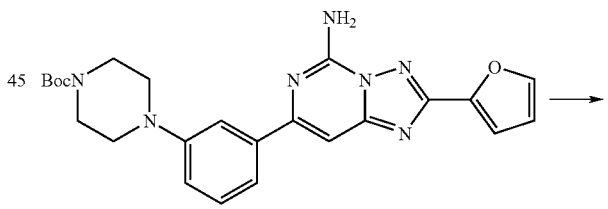

| COMPOUND | STRUCTURE | M + 1 (ESI) |
| --- | --- | --- |
| 107 | 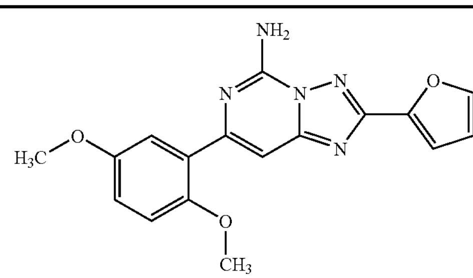 | 474.1 |

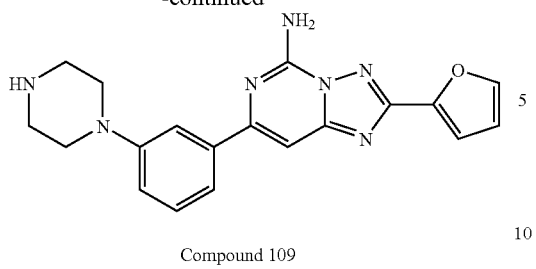

Compound 109

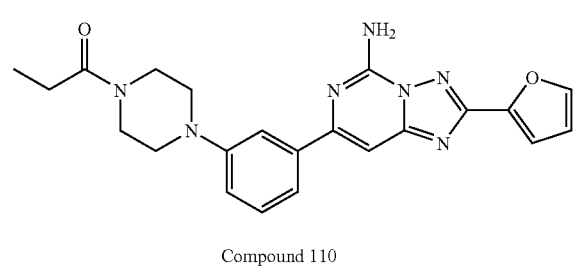

Compound 110

The compound from Example 10, step 7 was deprotected by treatment with a 4.0 M solution of HCl in dioxane at room temperature overnight or with a 50% TFA solution in dichloromethane for 30 min. under $N_2$, evaporated under reduced pressure and used without further purification. $^1$H NMR (DMSO-$d_6$) δ 7.97 (br.s, 2H), 7.94 (s, 1H), 7.64 (s, 1H), 7.50 (m, 2H), 7.30 (t, 1H), 7.08 (dd, 1H), 7.00 (dd, 1H), 6.70 (dd, 1H), 3.70 (br.s, 1H), 3.08 (m, 4H), 2.90 (m, 4H). Mass spectrum (ESI), $M^{+1}$: 362.1

Example 19

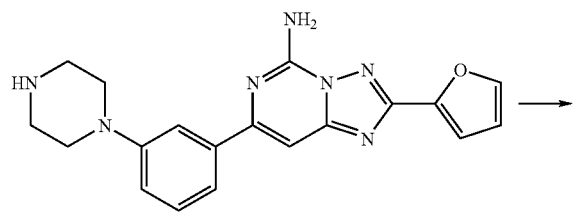

To a solution of the product from Example 18 (0.10 g, 0.25 mmol) and diisopropylethylamine (0.097 g, 0.75 mmol) in DMF (5 mL) was added propionyl chloride (0.025 g, 0.28 mmol) dropwise at room temperature under $N_2$. After 2 h, water was added and resultant extracted by ethyl acetate, dried by sodium sulfate and evaporated. Purification using silica gel Prep. TLC led to the product. $^1$H NMR (CDCl$_3$) δ 7.63 (dd, 1H), 7.60 (m, 1H), 7.46 (d, 1H), 7.40 (s, 1H), 7.37 (d, 1H), 7.24 (m, 1H), 7.01 (dd, 1H), 6.60 (dd, 1H), 6.06 (br. S, 2H), 3.82 (t, 2H), 3.65 (t, 2H), 3.25 (m, 4H), 2.40 (q, 2H), 1.19 (t, 3H). Mass spectrum (ESI) 418.1.

The following compounds were prepared in a similar fashion.

| COMPOUND | STRUCTURE | M + 1 (ESI) |
|---|---|---|
| 111 | 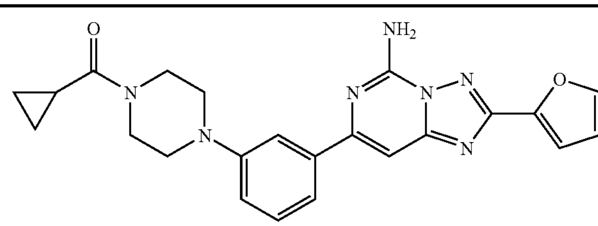 | 430.1 |
| 112 | 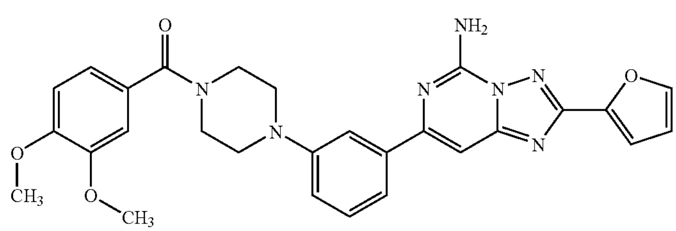 | 526.1 |
| 113 | 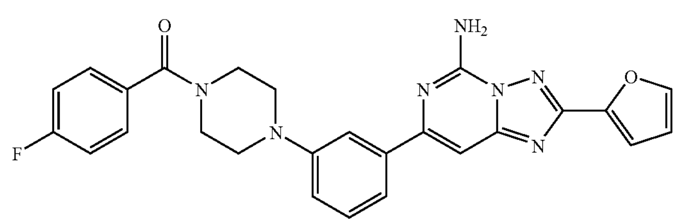 | 484.1 |

| COMPOUND | STRUCTURE | M + 1 (ESI) |
|---|---|---|
| 114 | 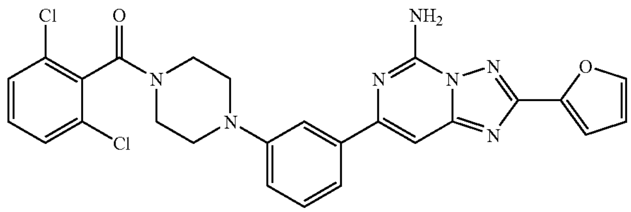 | 534.1 |
| 115 | 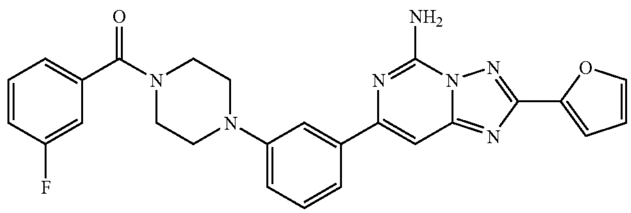 | 484.1 |

Example 20

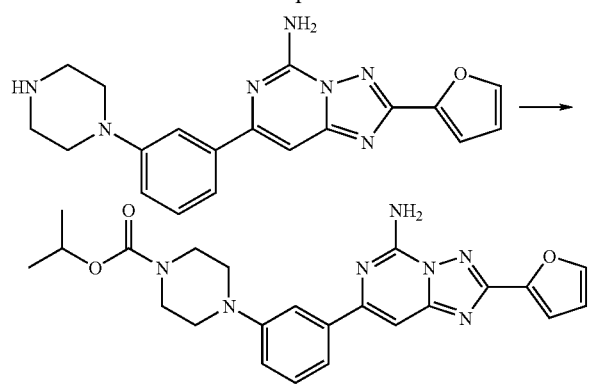

Compound 116

To a solution of the product from example 18 (0.125 g, 0.35 mmol) and diisopropylethylamine (0.134 g, 1.04 mmol) in DMF (5 mL) was added isopropyl chloroformate (7.0 mL, 0.7 mmol) dropwise at room temperature under $N_2$. After 2 h, water was added and the resultant was extracted by ethyl acetate, dried by sodium sulfate and evaporated. Purification was performed using silica gel. Prep. TLC led to product. $^1$H NMR (CDCl$_3$) δ 7.63 (m, 1H), 7.59 (m, 1H), 7.44 (d, 1H), 7.38 (s, 1H), 7.35 (d, 1H), 7.24 (m, 1H), 7.02 (dd, 1H), 6.58 (dd, 1H), 6.22 (br. S, 1H), 4.95 (m, 1H), 3.65 (m, 4H), 3.22 (m, 4H), 1.26 (d, 6H); Mass spectrum (ESI), $M^{+1}$: 448.1

The following compounds were prepared in a similar fashion:

| COMPOUND | STRUCTURE | M + 1 (ESI) |
|---|---|---|
| 117 | 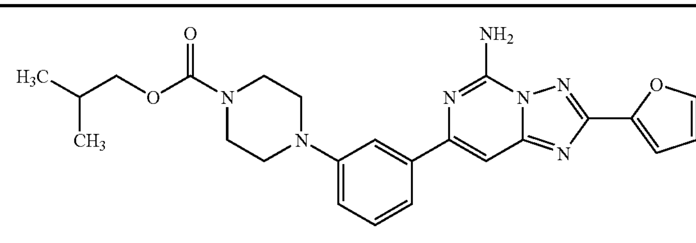 | 462.1 |
| 118 | 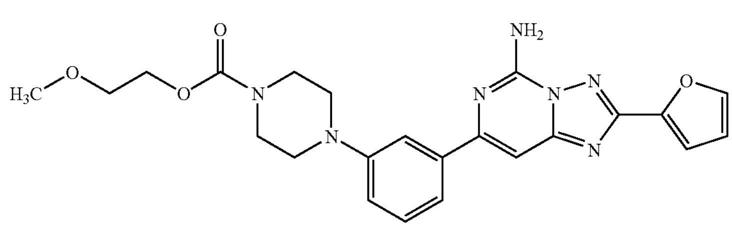 | 464.1 |

Example 21

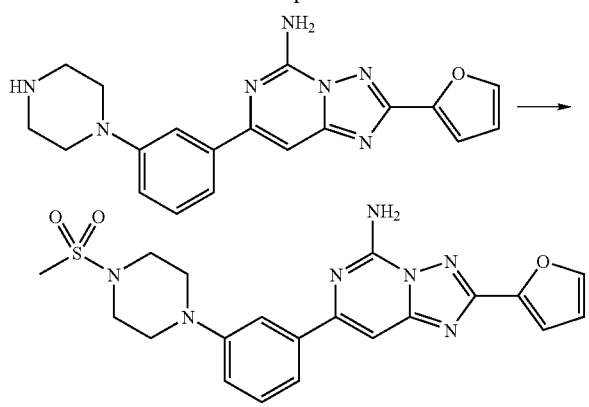

Compound 119

To a solution of the product from example 18 (0.11 g, 0.30 mmol) and diisopropylethylamine (0.043 g, 0.058 mmol) in DMF (5 mL) was added methyl sulfonyl chloride (0.038 mL, 0.026 mmol) dropwise at room temperature under $N_2$. After 3 h, water was added, and the resultant was extracted with ethyl acetate, dried by sodium sulfate and evaporated. Purification was performed using silica gel Prep. TLC led to the product. $^1$H NMR (CDCl$_3$) δ 7.62 (m, 2H), 7.50 (d, 1H), 7.40 (m, 2H), 7.23 (m, 1H), 7.04 (dd, 1H), 6.62 (dd, 1H), 6.00 (br. S, 2H), 3.37–3.42 (m, 8H), 2.82(s, 3H). Mass spectrum (ESI) 440.1.

The following compound was prepared in a similar fashion:

| COMPOUND | STRUCTURE | M + 1 (ESI) |
|---|---|---|
| 120 | 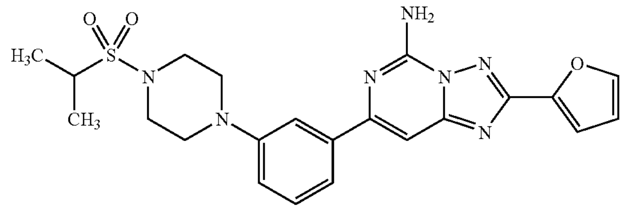 | 468.1 |

Example 22

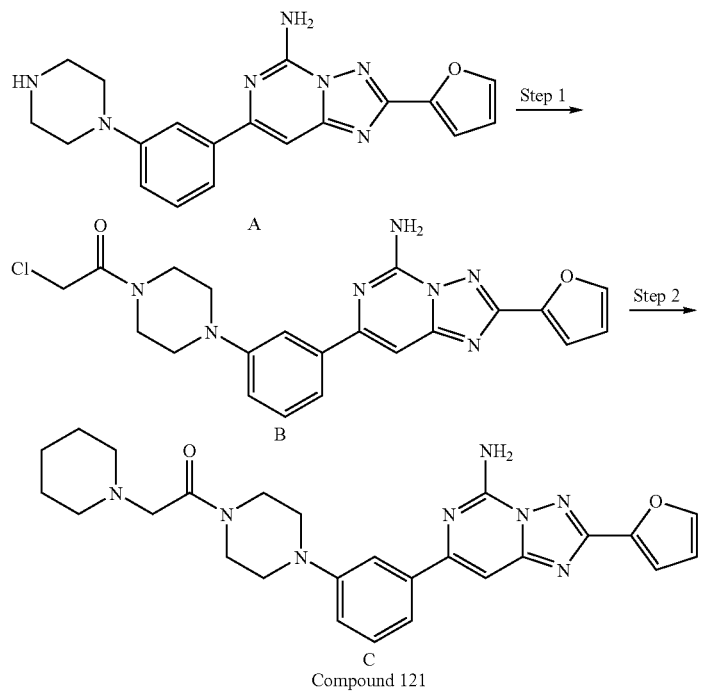

Compound 121

Step 1: To a solution of the product from Example 18 and diisopropylethylamine in DMF (5 mL) was added chloroacetyl chloride dropwise at 0° C. under $N_2$. The mixture was warmed to room temperature and stirred overnight. Water was then added and the resultant extracted by ethyl acetate, dried by sodium sulfate and evaporated. Purification was performed using column chromatography on silica gel using ethyl acetate to provide the intermediate B. Mass spectrum (ESI), $M^{+1}$: 438.1.

Step 2: Compound B from step 1 (0.11 g, 0.25 mmol) was treated with excess piperidine (10 equivalents) in DMF (5 mL) at room temperature under $N_2$, overnight. The mixture was evaporated under reduced pressure and the product C was purified by preparative TLC using ethyl acetate/methanol (9:1). $^1$H NMR (CDCl$_3$) δ 7.59(m, 1H), 7.54 (m, 1H), 7.40 (d, 1H), 7.33 (m, 2H), 7.20 (m, 1H), 6.97 (dd, 1H), 6.55 (dd, 1H), 6.17 (br. S, 2H), 3.80 (m, 2H), 3.74 (m, 2H), 3.20 (m, 4H), 3.13 (s, 2H), 2.38 (m, 4H), 1.49 (m, 4H), 1.38 (m, 2H). Mass spectrum (ESI), $M^{+1}$: 487.1.

The following compounds were prepared in a similar fashion:

| COMPOUND | STRUCTURE | M + 1 (ESI) |
|---|---|---|
| 122 | 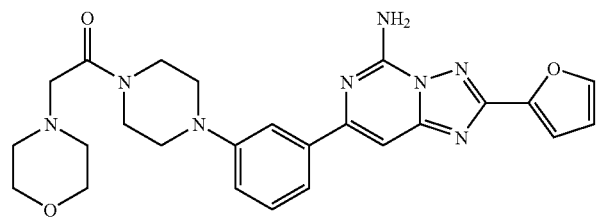 | 462.1 |
| 123 | 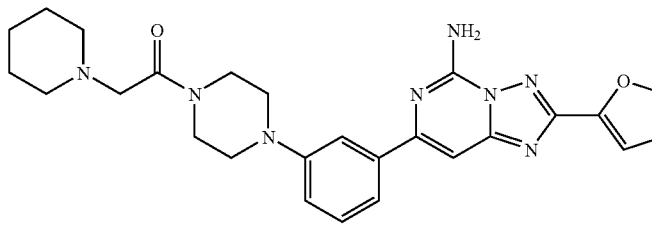 | 487.1 |
| 124 | 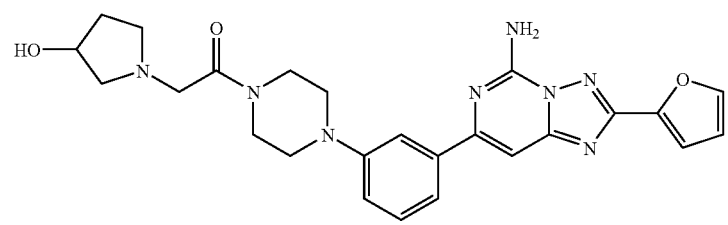 | 489.1 |
| 125 | 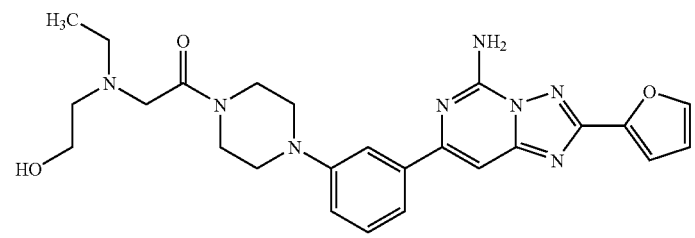 | 491.1 |
| 126 | 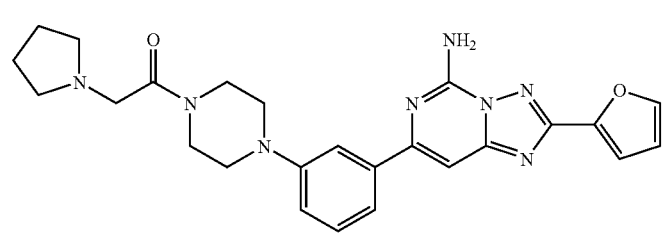 | 473.1 |

-continued

| COMPOUND | STRUCTURE | M + 1 (ESI) |
|---|---|---|
| 127 | 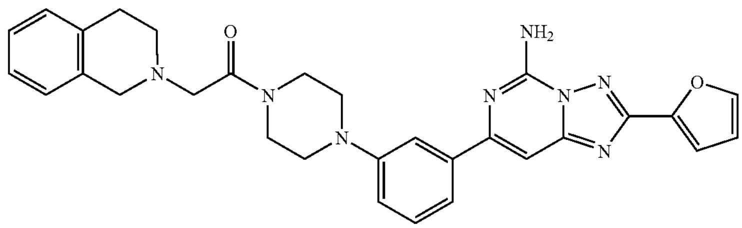 | 535.1 |
| 128 | 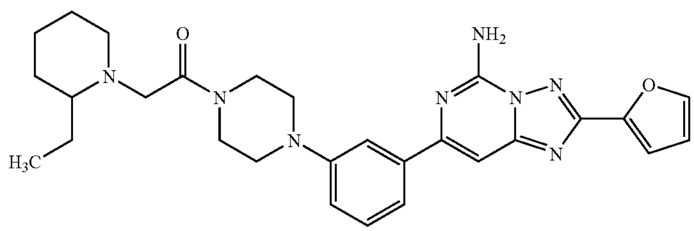 | 515.1 |
| 129 | 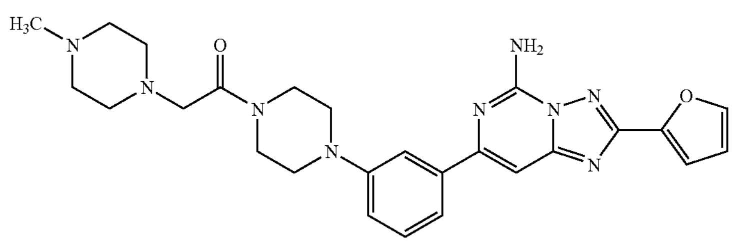 | 502.1 |

Example 23

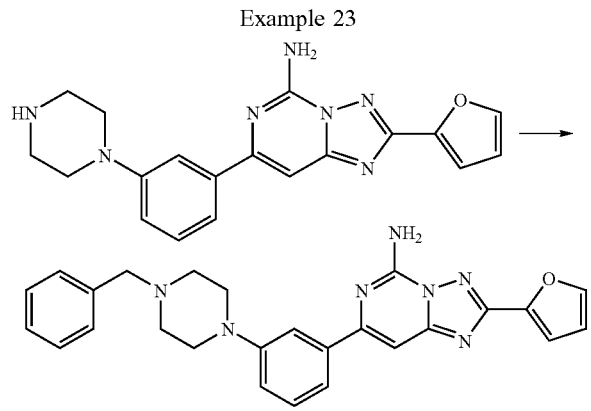

Step 1: To a solution of the product from Example 18 (0.145 g, 0.4 mmol) and benzaldehyde (0.047 g, 0.44 mmol) in dichloromethane (10 mL), was added sodium triacetoxyborohydride (0.127 g, 0.6 mmol) at room temperature under $N_2$. After 5 h, a 2.0 M solution of sodium hydroxide was added and the resultant extracted by dichloromethane, dried by sodium sulfate and evaporated. Purification by Prep. TLC led to the product. $^1$H NMR (CDCl$_3$) δ 7.63 (dd, 1H), 7.58 (m, 1H), 7.20–7.41 (m, 9H), 7.01 (dd, 1H), 6.59 (dd, 1H), 6.04 (br. S, 2H), 3.59 (s, 2H), 3.29 (t, 4H), 2.64 (t, 4H). Mass spectrum (ESI), $M^{+1}$: 452.1.

The following compounds were prepared in a similar fashion.

| COMPOUND | STRUCTURE | M + 1 (ESI) |
|---|---|---|
| 131 | 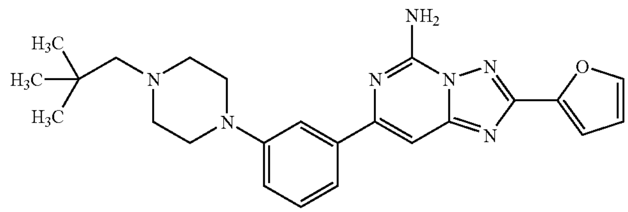 | 432.1 |
| 132 | 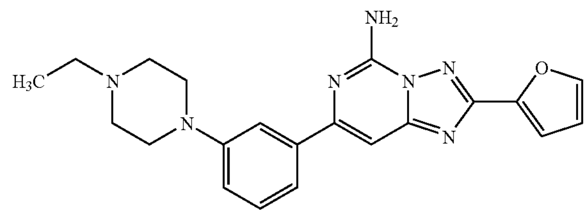 | 390.1 |
| 133 | 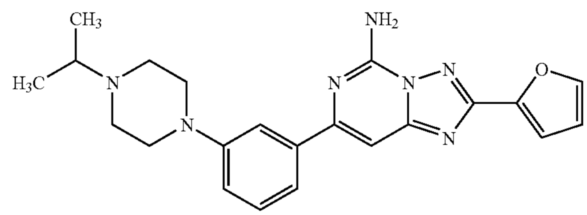 | 404.1 |
| 134 | 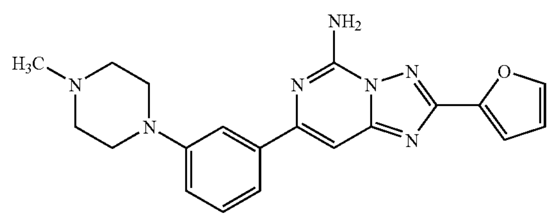 | 376.1 |
Example 24
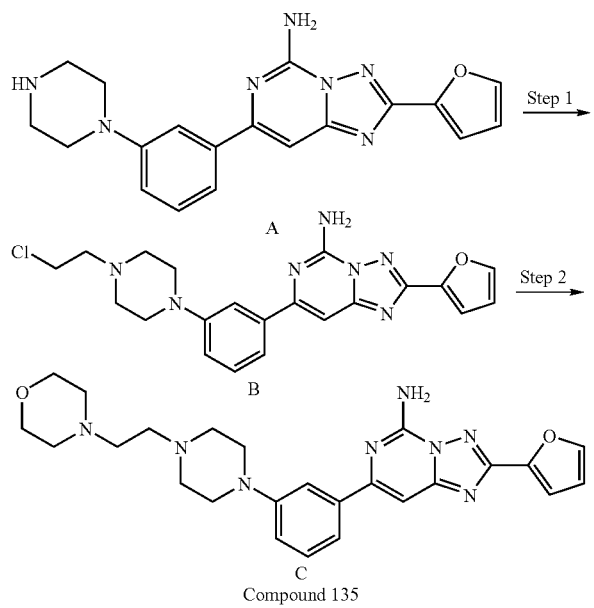
Compound 135

Step 1: To a solution of the product from Example 18 (1.22 g, 3.38 mmol) and chloroacetaldehyde (0.64 g, 4.06 mmol of 50% solution in water) in dichloromethane (60 mL), was added sodium triacetoxyborohydride (1.08 g, 5.07 mmol) at room temperature under $N_2$. After 5 h, a 2.0 M solution of sodium hydroxide was added and the resultant compound B was extracted by dichloromethane, dried by sodium sulfate and evaporated. Purification performed by column chromatography. Mass spectrum (ESI) $M^{+1}$: 424.1

Step 2: The compound from step 1B (0.09, 0.21 mmol) was treated with excess morpholine (10 equivalents) in DMF (5 mL) at room temperature under $N_2$, overnight. The mixture was evaporated under reduced pressure and purified by preparative TLC using ethyl acetate/methanol (9:1) resulting in compound C. $^1$H NMR (CDCl$_3$) δ 7.64 (dd, 1H), 7.58 (m, 1H), 7.30–7.44 (m, 3H), 7.25 (m, 2), 7.01 (dd, 1H), 6.60 (dd, 1H), 6.02 (br. S, 2H), 3.75 (m, 4H), 3.33 (m, 4H), 2.75 (m, 2H), 2.65 (m, 2H), 2.57 (m, 4H), 2.11 (m, 4H). Mass spectrum (ESI), $M^{+1}$: 475.1

The following compounds were prepared in a similar fashion:

Example 25

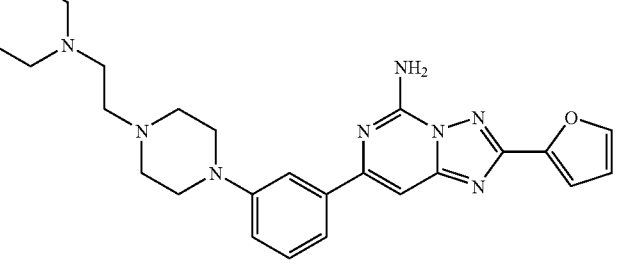

Compound 139

The product of Example 18 (0.10 g, 0.28 mmol) was heated with 1-fluoro-2-nitrobenzene (0.079 g, 0.56 mmol)

| COMPOUND | STRUCTURE | M + 1 (ESI) |
|---|---|---|
| 136 | 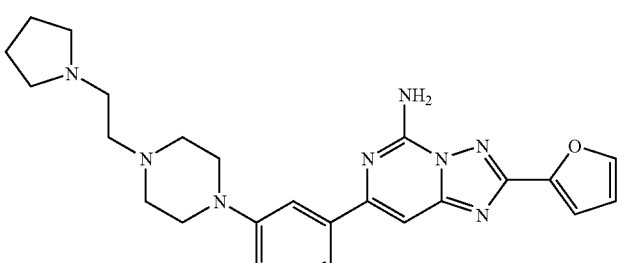 | 473.1 |
| 137 | 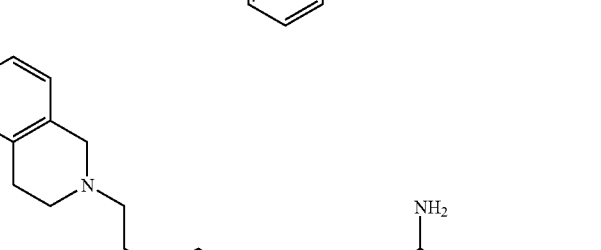 | 459.1 |
| 138 | | 521.1 | and triethylamine (0.085 g, 0.84 mmol) in DMF (5 mL) at 100° C. under N₂ for a period of 12 h. The mixture was evaporated under reduced pressure and purified by preparative TLC using ethyl acetate/hexane(7:3). ¹H NMR (CDCl₃) δ 7.89 (dd, 1H), 7.65 (m, 2H), 7.36–7.63 (m, 4H), 7.19–7.26 (m, 2H), 7.00–7.11 (m, 2H), 6.59 (dd, 1H), 6.11 (br. S, 2H), 3.43 (m, 4H), 3.26 (m, 4H). Mass spectrum (ESI), M⁺¹: 483.1

Example 26

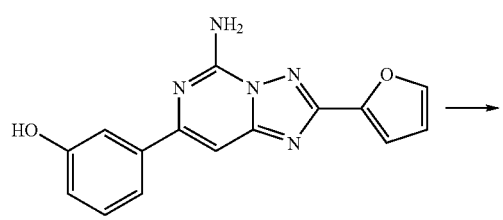

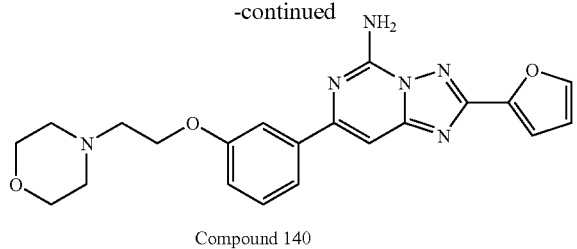

Compound 140

A mixture of phenol derivative prepared as in Example 4 (0.054 g, 0.18 mmol), chloroethylmorpholine hydrochloride (0.041 g, 0.22 mmol), potassium carbonate (0.076 g, 0.55 mmol) and potassium iodide (0.031 g, 0.18 mmol) was heated at 50° C. in acetonitrile (10 mL) under N₂ for a period of 19 h. The mixture was diluted with ethyl acetate and filtered, concentrated under vacuum and purified by chromatography on silica gel. ¹H NMR (CD₃OD) δ 7.76 (m, 1H), 7.71 (m, 1H), 7.66 (m, 1H), 7.38 (m, 2H), 7.24 (dd, 1H), 7.03 (dd, 1H), 6.66 (dd, 1H), 4.23 (t, 2H), 3.73 (t, 4H), 2.85 (t, 2H), 2.63 (t, 4H). Mass spectrum (ESI), Mass spectrum (ESI), M⁺¹: 407.1.

The following compounds were prepared in a similar fashion:

| COMPOUND | STRUCTURE | M + 1 (ESI) |
|---|---|---|
| 141 | 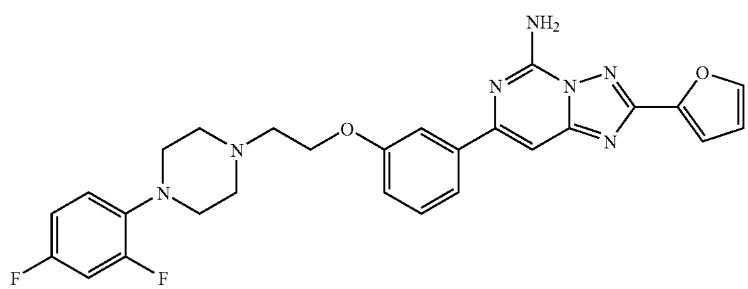 | 518.1 |
| 142 | 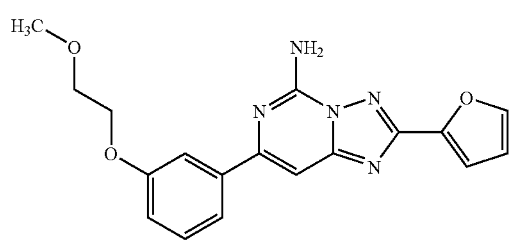 | 352.1 |
| 143 | 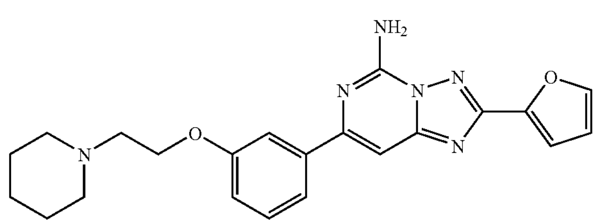 | 405.1 |

-continued

| COMPOUND | STRUCTURE | M + 1 (ESI) |
|---|---|---|
| 144 | 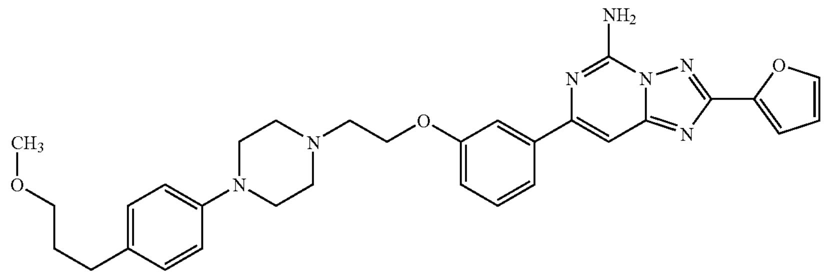 | 556.1 |
| 145 | 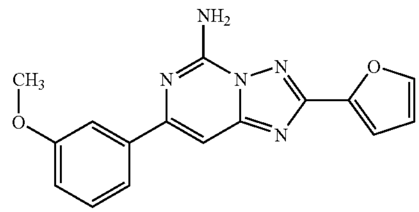 | 308.1 |
| 146 | 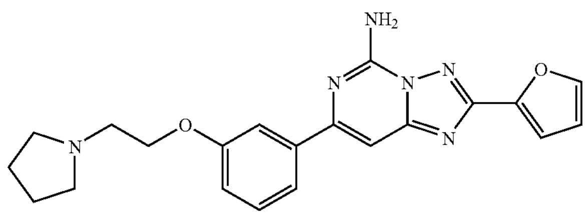 | 391.1 |

Example 27

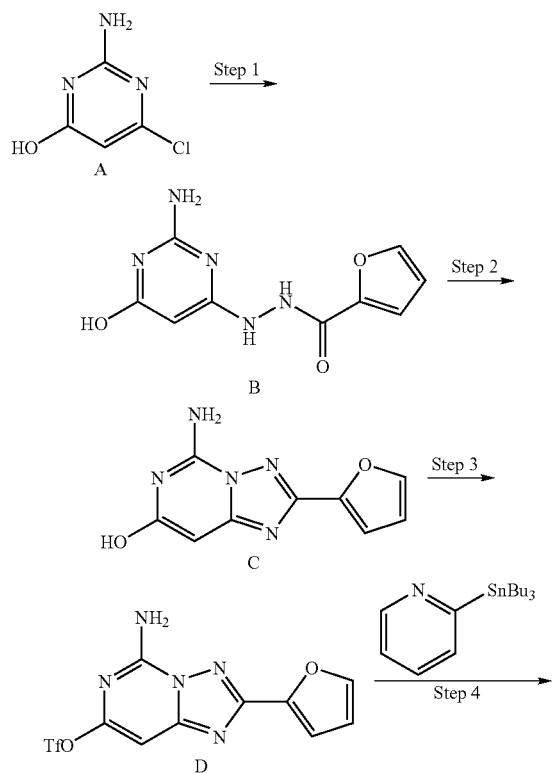

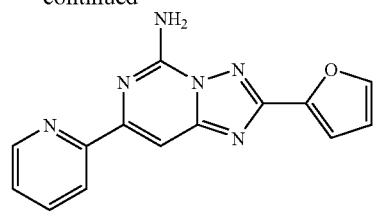

E
Compound 147

Step 1: A mixture of 2-amino-6-chloro-4-pyrimidinol monohydrate (2.0 g, 13.74 mmol) and 2-furoic hydrazide (1.91 g, 15.12 mmol) was heated in n-butanol (50 mL) at 100° C. for 20 h. The mixture was concentrated under vacuum to provide a solid residue B that was used without purification. Mass spectrum (ESI), $M^{+1}$: 236.1

Step 2: The product of step 1 B (3.24 g, 13.74 mmol) was heated in N,O-bis(trimethylsilyl)acetamide (20.5 mL, 82.44 mmol) at 120° C. overnight. The mixture was cooled, and then methanol and water were slowly added and heated to reflux for 4 h. The resulting mixture was cooled to room temperature and the precipitate C was collected by filtration. Mass spectrum (ESI), $M^{+1}$: 218.0

Step 3: Triflic anhydride (1.52 g, 5.37 mmol) was added dropwise to a solution of product from step 2 C (1.06 g, 4.88 mmol) and triethylamine (0.54 g, 5.37 mmol) in dichloromethane (20 mL) at 0° C. under $N_2$. After 1 h, the mixture was warmed to room temperature and added a saturated solution of sodium bicarbonate. The resultant mixture was extracted with dichloromethane, dried by sodium sulfate and evaporated after filtration. Column chromatography on silica gel then led to the product D. Mass spectrum (ESI), M$^{+1}$: 350.1.

Step 4: A mixture of product from step 3 D (0.25 g, 0.72 mmol), 2-pyridyltributyltin (0.32 g, 0.86 mmol), and Pd(dppf)Cl$_2$ (0.029 g, 0.036 mmol) was heated in DMF (5 mL) at 80° C. for 64 h under N$_2$. Water was added followed by extraction with ethyl acetate, drying with sodium sulfate and then filtering. The residue E after evaporation was purified by chromatography on silica gel. $^1$H NMR (DMSO-d$_6$) δ 8.70(dd, 1H), 8.30 (d, 1H), 8.01 (br. S, 2H), 7.95 (m, 2H), 7.82 (s, 1H), 7.47 (m, 1H), 7.22 (dd, 1H), 6.72 (dd, 1H). Mass spectrum (ESI), M$^{+1}$: 279.0

Example 28

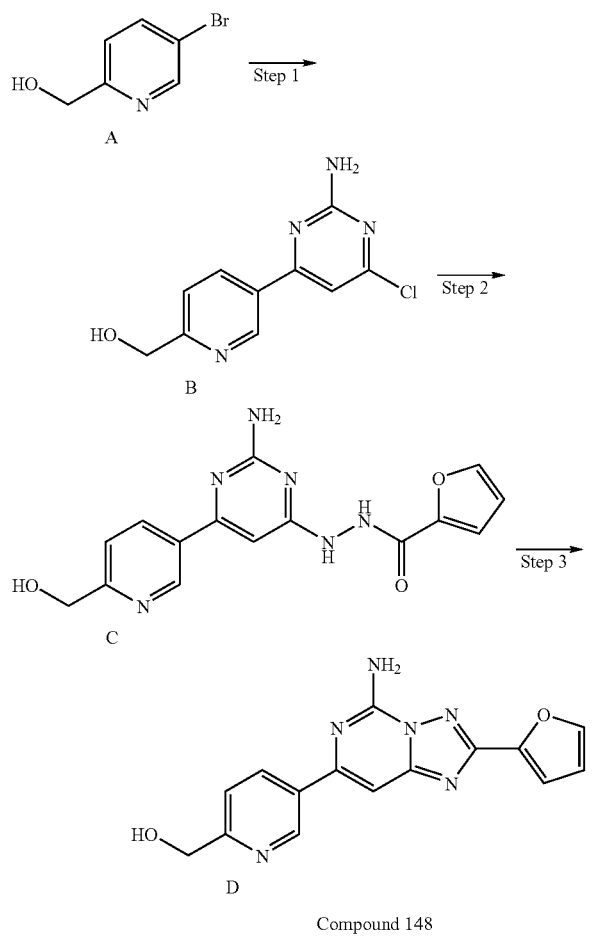

Compound 148

Step 1: A mixture of 2-hydroxymethyl-5-bromopyridine (2.17 g, 11.54 mmol), bis(pinacolato)diboron (2.93 g, 11.54 mmol), PdCl$_2$(dppf) (0.57 g, 0.69 mmol), and potassium acetate (3.40 g, 34.62 mmol) was heated in 1,4-dioxane (65 mL) at 80° C. under N$_2$ overnight. The mixture was cooled to room temperature, then 2-amino-4,6-dichloro-pyrimidine (3.79 g, 23.08 mmol) and a 2.0 M solution of sodium bicarbonate (6.12 g in 20 mL of water) were added. The resultant mixture was heated at 80° C. for 20 h, cooled, and then diluted by ethyl acetate and water. Organic extract was washed with brine, dried with sodium sulfate and evaporated. The residue was purified by column chromatography on silica gel to give product B. $^1$H NMR (CD$_3$OD) δ 9.21 (d, 1H), 8.55 (dd, 1H), 7.76 (d, 1H), 7.75 (d, 1H), 7.49(s, 1H), 7.25 (dd, 1H), 6.66 (dd, 1H), 4.78 (2H). Mass spectrum (ESI), M$^{+1}$: 309.1.

Steps 2 and 3: Same as steps 2, and 3 of example 4. $^1$H NMR (CD$_3$OD) δ 9.21 (d, 1H), 8.55 (dd, 1H), 7.76 (d, 1H), 7.75 (d, 1H), 7.49(s, 1H), 7.25 (dd, 1H), 6.66 (dd, 1H), 4.78 (2H). Mass spectrum (ESI), M$^{+1}$: 309.1.

Example 29

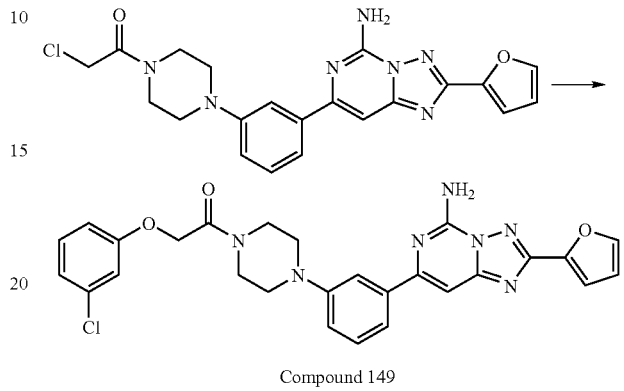

Compound 149

Step 1: To a solution of 3-chlorophenol (0.062 g, 0.48 mmol) and sodium hydride (0.058 g, 1.44 mmol of 60% NaH in mineral oil) in DMF (5 mL) at room temperature under N$_2$, was added the product of step 1 example 22 (0.11 g, 0.24 mmol) and the mixture was stirred overnight. Water was then added and the mixture was extracted by ethyl acetate, dried by sodium sulfate, filtered and concentrated under vacuum. Purification by preparative TLC on silica gel using ethyl acetate gave the product. $^1$H NMR (CDCl$_3$) δ 7.61 (s, 1H), 7.60 (m, 1H), 7.47 (m, 1H), 7.22 (m, 3H), 7.00 (m, 2H), 6.88 (dd, 1H), 6.60 (dd, 1H), 5.93 (br.s, 2H), 4.75 (s, 2H), 3.80 (m, 4H), 3.17 (m, 4H). Mass spectrum (ESI), M$^{+1}$: 530.1

Example 30

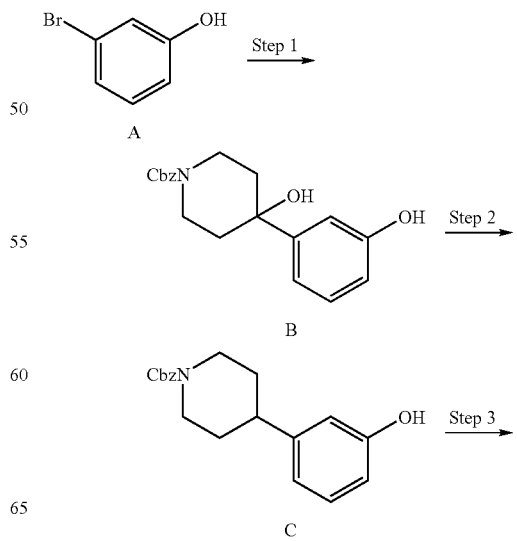

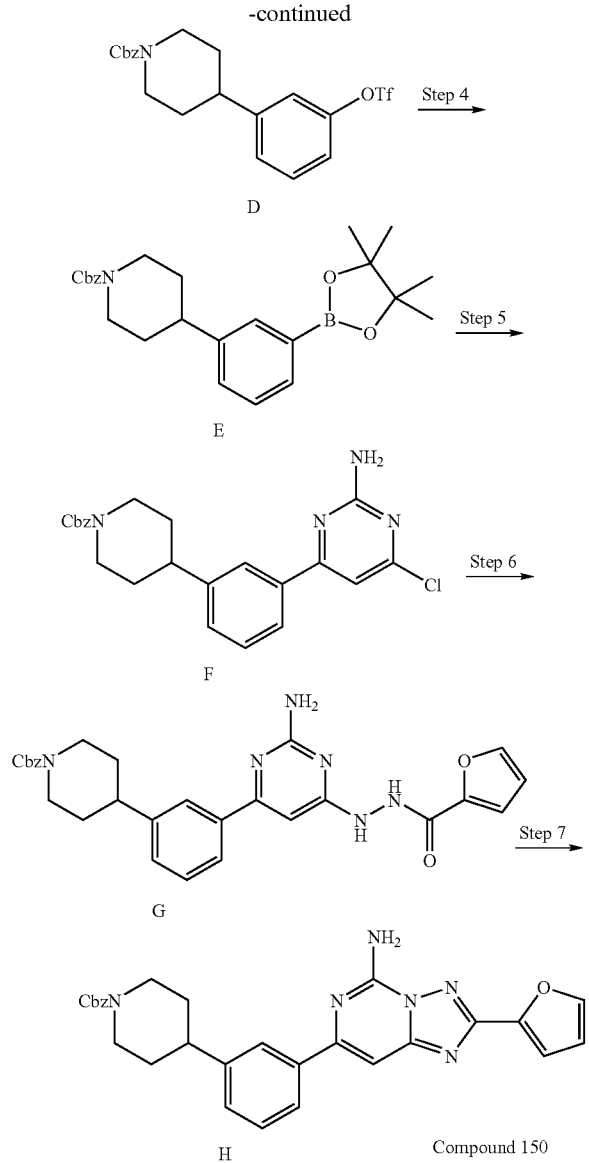

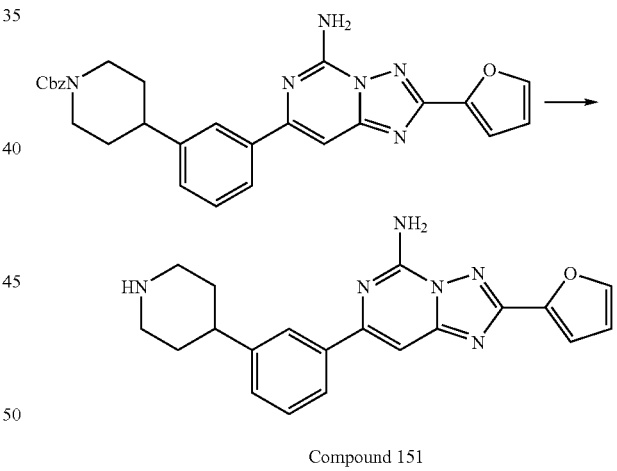

Compound 151

STEP 4: The product of Step 3 D (412 mg, 0.93 mmol) was treated as in Example 11, Step 4 to afford E. Mass spectrum (ESI): 422.1

STEP 5: The product of Step 4 E (250 mg, 0.59 mmol) was treated with 2-amino-4,6-dichloropyrimidine (195 mg, 1.18 mmol) as in Example 4, Step 1 (except 4 eq. of Na₂CO₃ was used) to afford F. Mass spectrum (ESI): 423.1

STEP 6: The product of Step 5 F (155 mg, 0.37 mmol) was combined with 2-furoic hydrazide (60 mg, 0.48 mmol) in nBuOH (3 mL). The mixture was stirred and heated at 110° C. for 20 h. The temperature was cooled to room temperature, and concentrated in vacuo to afford a solid G, which was carried on without further purification. Mass spectrum (ESI): 513.1

STEP 7: The product of Step 6 G was combined (188 mg, 0.37 mmol) with N,O-bis(trimethylsilyl)acetamide (1.65 g, 8.5 mmol). The mixture was stirred and heated at 110° C. for 4 h under N₂. The mixture was cooled to room temperature and concentrated in vacuo. The residue was taken up in 2:1 H₂O/MeOH, heated at 100° C. for 2 h, concentrated in vacuo and partitioned between H₂O and EtOAc. The organics were washed with brine, dried over MgSO₄, filtered, concentrated in vacuo, and chromatographed to afford a solid H. Mass spectrum (ESI): 495.1, ¹H NMR (CDCl₃) δ 7.93 (s, 1H), 7.82 (d, 1H), 7.64 (m, 2H), 7.28–7.52 (m, 7H), 6.78 (bs, 1H), 6.63 (m, 1H), 5.19 (s, 2H), 4.38 (bs, 2H), 2.92 (bs, 2H), 2.80 (m, 1H), 1.91 (d, 2H), 1.70 (m, 2H)

Example 31

STEP 1: t-Butyl lithium in pentane (11.56 mL, 19.7 mmol of 1.7 N in pentane) was added dropwise to a solution of 3-bromophenol (1.0 g, 5.8 mmol) in THF (86 mL) and cooled to −78° C. under N₂. The mixture was stirred for 10 min. Benzyl-4-oxo-1-piperidine carboxylate (1.35 g, 5.8 mmol) in THF (14 mL) was added at −78° C. The mixture was warmed to room temperature, stirred for 2 h, and partitioned between sat'd NaHCO₃ and EtOAc. The organics were washed with H₂O, brine, dried over MgSO₄, filtered, concentrated in vacuo, and chromatographed to afford B. Mass spectrum (ESI): 328.1, 310.0

STEP 2: Triethylsilane (1.45 g, 12.5 mmol) and trifluoroacetic acid (1.42 g, 12.5 mmol) were added to a solution of the product of Step 1 B (0.87 g, 2.66 mmol) in CH₂Cl₂ (23 mL) and cooled to −78° C. under N₂. Stirring was continued for 2 h at −78° C. and 20 h at room temperature. The mixture was partitioned between sat'd NaHCO₃ and CH₂Cl₂. The organics were washed with H₂O, brine, dried over MgSO₄, filtered, concentrated in vacuo, and chromatographed to afford C. Mass spectrum (ESI): 312.0

STEP 3: The product of Step 2 C (458 mg, 1.47 mmol) was treated as in Example 11, Step 3 to afford D. Mass spectrum (ESI): 444.1

The product of Example 30, Step 7 (54 mg, 0.11 mmol), was combined in 10 ammonium acetate (7 mg, 0.091 mmol), and 10% Pd/C (8 mg) in MeOH (3 mL). The mixture was stirred under H₂ at atmospheric pressure and room temperature for 3 h. The mixture was filtered over celite, and the filtrate was concentrated in vacuo. The filtrate was partitioned between sat'd NaHCO₃ and CH₂Cl₂. The organics were washed with brine, dried over MgSO₄, filtered, and concentrated in vacuo to afford a solid. Mass spectrum (ESI): 361.1, ¹H NMR (CD₃OD) δ 8.00 (s, 1H), 7.94 (d, 1H), 7.76 (s, 1H), 7.34–7.44 (m, 3H), 7.25 (m, 1H), 6.67 (m, 1H), 3.23 (d, 2H), 2.82 (m, 3H), 1.93 (d, 2H), 1.80 (m, 2H)

Example 32

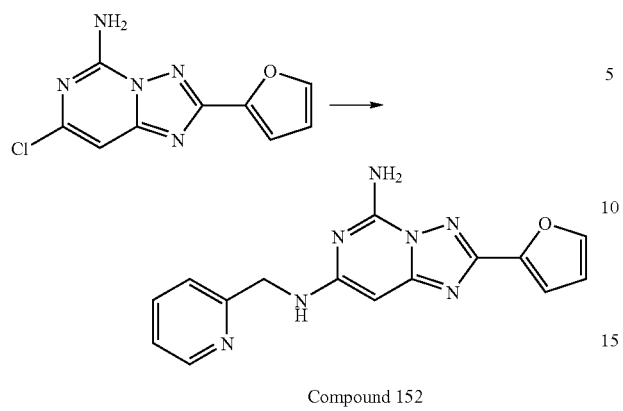

Compound 152

A mixture of 2-(aminomethyl)pyridine (92 mg, 0.85 mmol), the product of Example 2, Step 2 (100 mg, 0.43 mmol), and $K_2CO_3$ (177 mg, 1.28 mmol) in nBuOH (2 mL) was heated at 120° C. for 48 h in a sealed tube. The mixture was cooled to room temperature, filtered, and concentrated in vacuo. The residue was chromatographed on silica gel to afford a solid. Mass spectrum (ESI): 308.1, $^1$H NMR (CDCl$_3$) δ 8.57 (m, 1H), 7.68 (m, 1H), 7.57 (s, 1H), 7.34 (d, 1H), 7.21 (m, 1H), 7.14 (dd, 1H), 6.55 (m, 1H), 6.39 (bs, 1H), 6.05 (s, 2H), 5.87 (s, 1H), 4.54 (d, 2H)

The following compounds were prepared in a similar manner:

Example 33

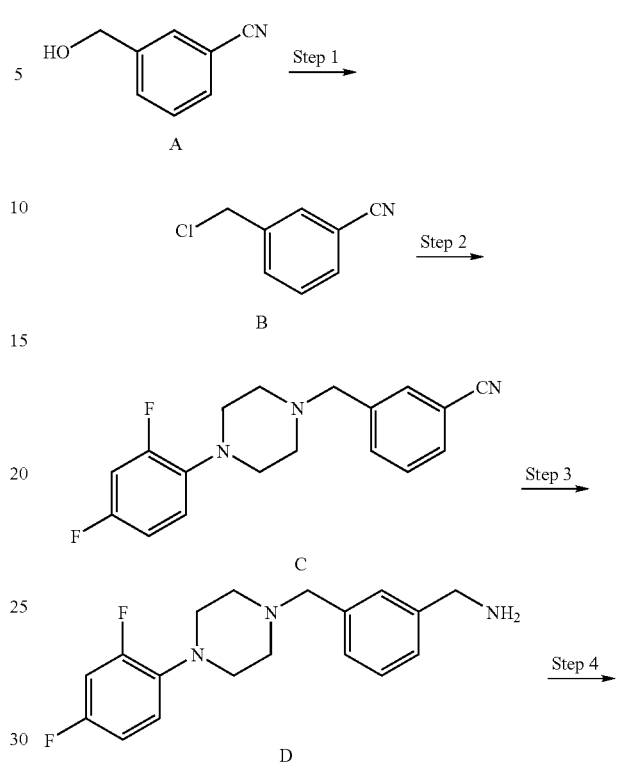

| COMPOUND | STRUCTURE | M + 1 (ESI) |
|---|---|---|
| 153 | 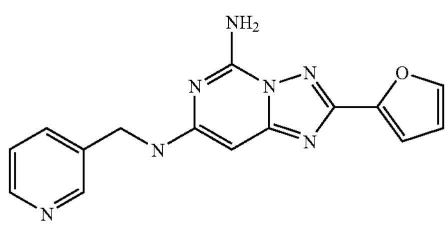 | 308.1 |
| 154 | 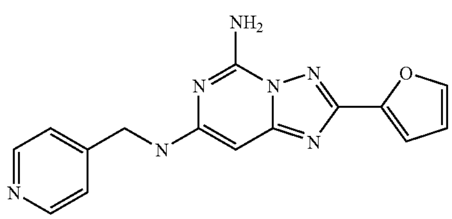 | 308.1 |
| 155 | 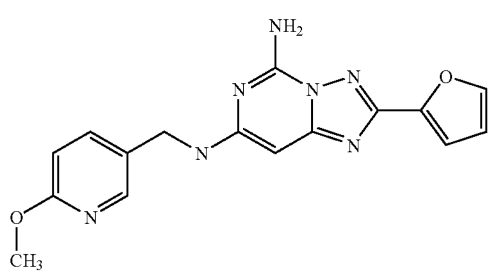 | 338.1 |

-continued

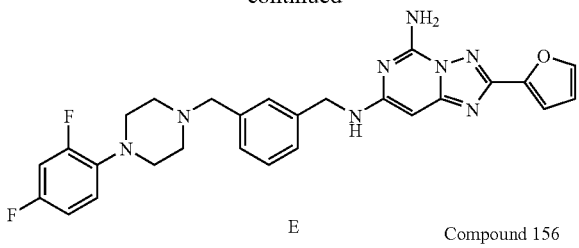

E  Compound 156

STEP 1: 3-(hydroxymethyl)benzonitrile (2.0 g, 15 mmol) was combined with triethylamine (9.11 g, 90 mmol) in CH$_2$Cl$_2$ (200 mL). The mixture was cooled to 0° C. under N$_2$ and SOCl$_2$ (8.94 g, 75 mmol) was added dropwise. The mixture was stirred for 1 h at 0° C., treated with ice, neutralized with sat'd NaHCO$_3$, and extracted with CH$_2$Cl$_2$. The organics were washed with H$_2$O and brine, dried over MgSO$_4$, filtered, and concentrated in vacuo to afford a solid B which was carried on without further purification. $^1$H NMR (CDCl$_3$) δ 7.70 (s, 1H), 7.63 (m, 2H), 7.49 (t, 1H), 4.59 (s, 2H)

STEP 2: The product of Step 1 B (1.04 g, 6.86 mmol), 2,4-difluorophenylpiperazine (1.24 g, 6.24 mmol), K$_2$CO$_3$ (2.59 g, 19 mmol), and KI (1.04 g, 6.24 mmol) were combined in CH$_3$CN (75 mL) and refluxed under N$_2$ for 20 h. The mixture was filtered, concentrated in vacuo, and chromatographed on silica gel to afford C. Mass spectrum (ESI): 314.1

STEP 3: A solution of the product of Step 2 C (0.96 g, 3.06 mmol) in THF (5 mL) was added dropwise to a suspension of LAH (0.128 g, 3.37 mmol) in THF (7 mL), and cooled to 0° C., under N$_2$. The mixture was stirred for 1 h at room temperature, cooled to 0° C., treated with ice, quenched with 1 N NaOH, and warmed back to room temperature. The resultant solid was filtered and washed with THF. The filtrate was concentrated in vacuo to afford D which was carried on without further purification. Mass spectrum (ESI): 318.1

STEP 4: The product of Step 3 D (270 mg, 0.85 mmol) was combined with the product of Example 2, Step 2 (100 mg, 0.43 mmol) as in Example 32 to afford a solid E. Mass spectrum (ESI): 517.1, $^1$H NMR (CD$_3$OD) δ 7.68 (s, 1H), 7.39 (s, 1H), 7.27 (m, 3H), 7.21 (m, 1H), 7.07 (d, 1H), 6.92 (m, 3H), 6.60 (dd, 1H), 5.69 (s, 1H), 4.54 (s, 2H), 3.61 (s, 2H), 2.92 (m, 4H), 2.60 (m, 4H)

The following compounds were prepared in a similar manner:

| COMPOUND | STRUCTURE | M + 1 (ESI) |
|---|---|---|
| 157 | 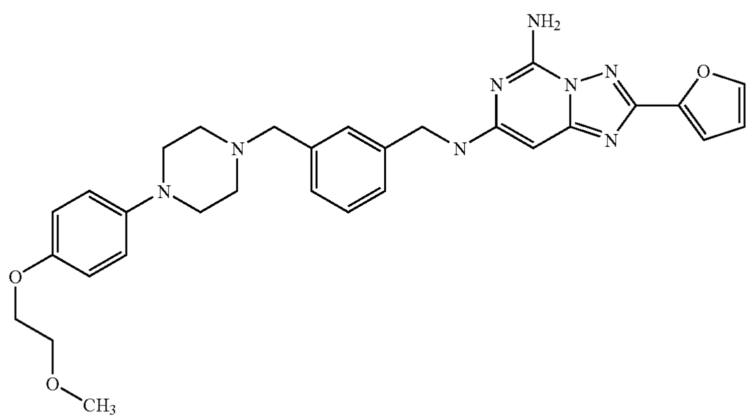 | 555.1 |
| 158 | 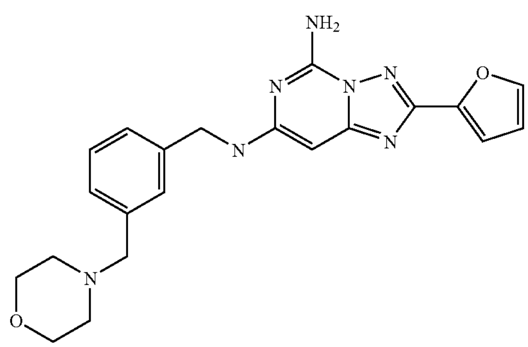 | 406.1 |

-continued

| COMPOUND | STRUCTURE | M + 1 (ESI) |
|---|---|---|
| 159 | 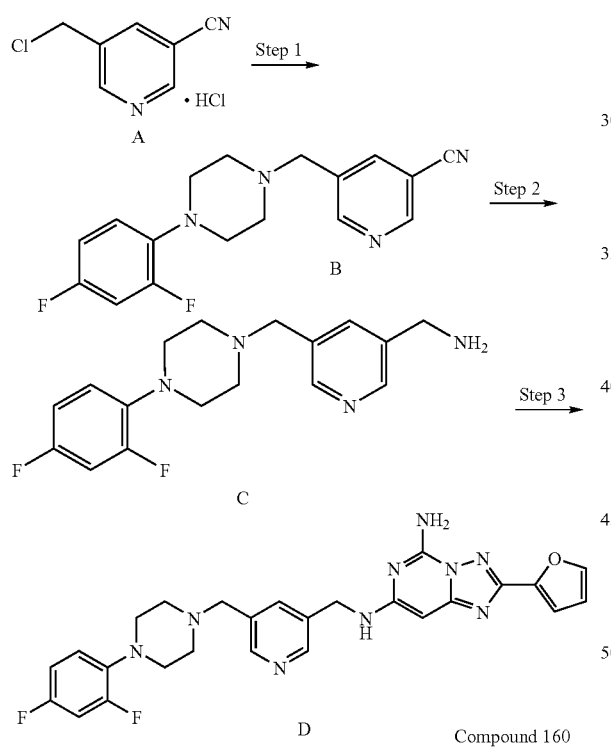 | 419.1 |

Example 34

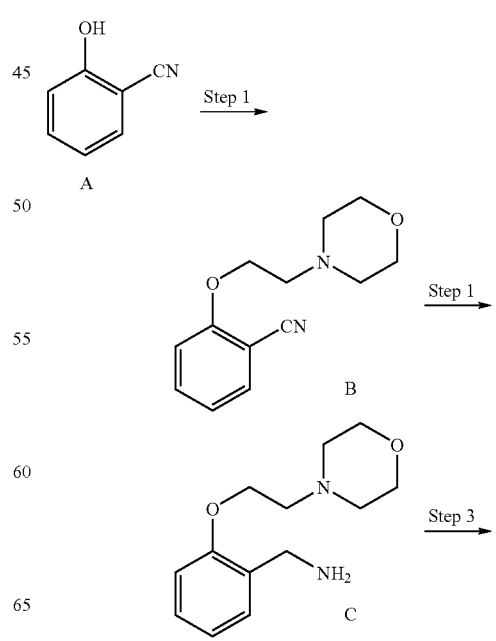

Compound 160

STEP 1: 3-(chloromethyl)-5-cyanopyridinium hydrochloride [prepared as described in: *Chem. Pharm. Bull.* 38, 1990, 2446–58; *Chem. Eur. J.* 3, 1997, 410–16] (260 mg, 1.38 mmol), 2,4-difluorophenylpiperazine (228 mg, 1.15 mmol), and triethylamine (326 mg, 3.22 mmol) were combined in DMF (7 mL). The mixture was stirred at room temperature for 48 h. The mixture was concentrated in vacuo and partitioned between $H_2O$ and $CH_2Cl_2$. The organics were washed with brine, dried over $MgSO_4$, filtered, concentrated in vacuo, and chromatographed to afford a solid B. Mass spectrum (ESI): 315.1

STEP 2: The product of Step 1 B (223 mg, 0.71 mmol), MeOH (3 mL), THF (3 mL), 25% $NH_4OH$ (aq) (3 mL), and Raney nickel were combined, washed wet with EtOH, (0.050 g) in a Parr bottle and hydrogenated under 50 psi for 24 h. The mixture was filtered over celite and the filtrate was concentrated in vacuo to afford a solid C, which was carried on without further purification. Mass spectrum (ESI): 319.1

STEP 3: The product of Step 2 C (230 mg, 0.72 mmol) and the product of Example 2, Step 2 (85 mg, 0.36 mmol) were combined as in Example 32 to afford a solid D. Mass spectrum (ESI): 518.1, $^1H$ NMR ($CD_3OD$) δ 8.47 (s, 1H), 8.37 (s, 1H), 7.88 (s, 1H), 7.69 (s, 1H), 7.08 (d, 1H), 6.86 (m, 4H), 6.60 (dd, 1H), 5.77 (s, 1H), 4.62 (s, 2H), 3.62 (s, 2H), 3.04 (m, 2H), 2.89 (m, 2H), 2.65 (m, 2H), 2.56 (m, 2H)

Example 35

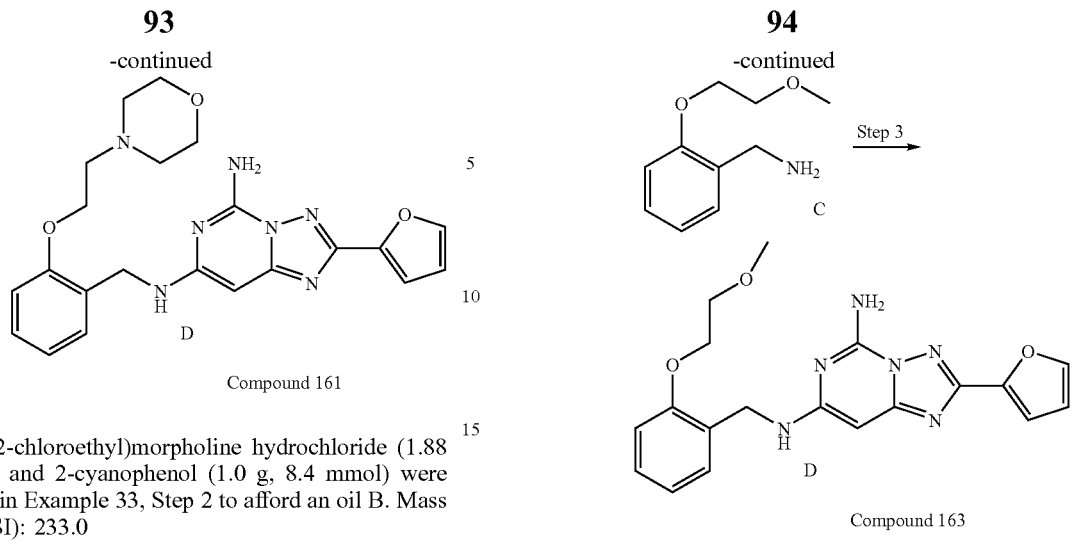

Compound 161

STEP 1: 4-(2-chloroethyl)morpholine hydrochloride (1.88 g, 10 mmol) and 2-cyanophenol (1.0 g, 8.4 mmol) were combined as in Example 33, Step 2 to afford an oil B. Mass spectrum (ESI): 233.0

STEP 2: The product of Step 1 B (502 mg, 2.16 mmol) was hydrogenated as in Example 34, Step 2 to afford an oil C. Mass spectrum (ESI): 237.0

STEP 3: The product of Step 2 C (202 mg, 0.85 mmol) and the product of Example 2, Step 2 (100 mg, 0.43 mmol) were combined as in Example 32 to afford a solid D. Mass spectrum (ESI): 436.1, $^1$H NMR (CD$_3$OD) δ 7.69 (s, 1H), 7.28 (m, 2H), 7.10 (dd, 1H), 6.93 (m, 2H), 6.60 (dd, 1H), 5.75 (s, 1H), 4.48 (s, 2H), 4.21(t, 2H), 3.70 (m, 4H), 2.86 (t, 2H), 2.61 (m, 4H)

The following compound was prepared in a similar manner:

| COMPOUND | STRUCTURE | M + 1 (ESI) |
|---|---|---|
| 162 | 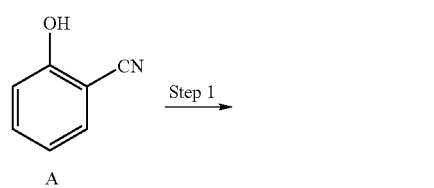 | 436.1 |

Example 36

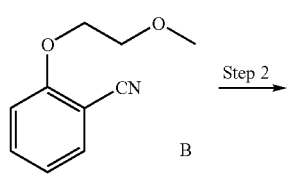

STEP 1: A solution of 2-cyanophenol (1.0 g, 8.4 mmol) in DMF (30 ml) was added dropwise to a suspension of NaH (60% in oil, 502 mg, 12.6 mmol) in DMF (12 ml) cooled to 0° C. under N$_2$. After the addition was complete, the mixture was stirred for 20 min. at room temperature. 2-bromoethyl methyl ether (1.4 g, 10 mmol) was added and the mixture was stirred for 70 h. The mixture was concentrated in vacuo. The resultant solid was suspended in hexane, which was decanted off. The undissolved solid was partitioned between H$_2$O and EtOAc. The organics were washed with H$_2$O, brine, dried over MgSO$_4$, filtered, concentrated in vacuo, combined with the above hexane wash and chromatographed to afford an oil B. Mass spectrum (ESI): 178.1

STEP 2: The product of Step 1 (623 mg, 3.52 mmol) was hydrogenated as in Example 34, Step 2 to afford an oil C. Mass spectrum (ESI): 182.0

STEP 3: The product of Step 2 (152 mg, 0.85 mmol) and the product of Example 2, Step 2 (100 mg, 0.43 mmol) were combined as in Example 32 to afford an oil D. Mass spectrum (ESI): 381.1, $^1$H NMR (CD$_3$OD) δ 7.68 (s, 1H), 7.24 (m, 2H), 7.09 (dd, 1H), 6.93 (m, 2H), 6.60 (m, 1H), 5.75 (s, 1H), 4.50 (s, 2H), 4.19 (m, 2H), 3.80 (m, 2H), 3.45 (s, 3H)

Example 37

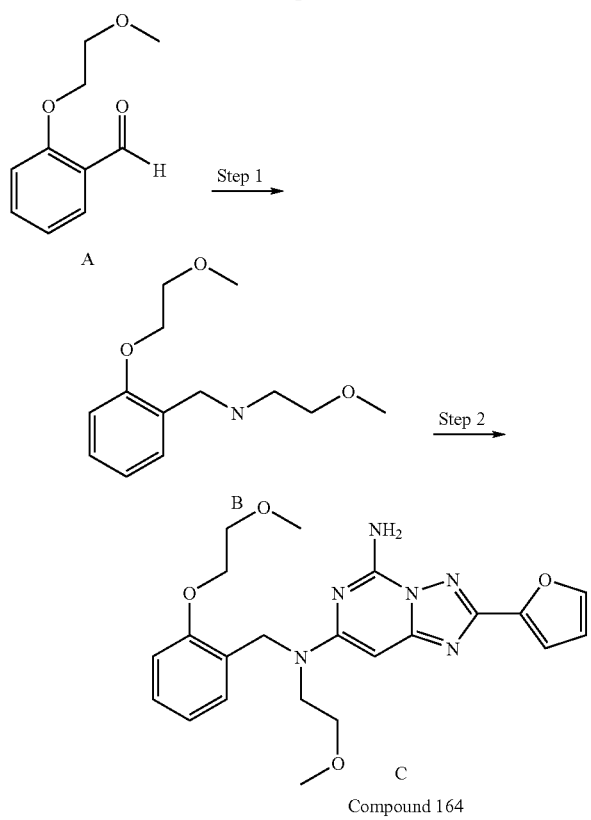

Compound 164

STEP 1: 2-(2-methoxyethoxy)benzaldehyde [prepared as described in: *Chem. Pharm. Bull.* 35, 1987, 1953–68] (400 mg, 2.22 mmol) and 2-methoxyethylamine (228 mg, 1.15 mmol) were combined in MeOH (10 mL) and the mixture was stirred at room temperature for 20 h, under $N_2$. The mixture was cooled to 0° C., and $NaBH_4$ (134 mg, 3.55 mmol) was added. The mixture was stirred for 20 h at room temperature under $N_2$. The mixture was partitioned between sat'd $NaHCO_3$ and $Et_2O$. The organics were washed with $H_2O$ and brine, and dried over $MgSO_4$. The mixture was filtered and concentrated in vacuo to afford an oil B, which was carried on without further purification. Mass spectrum (ESI): 240.1

STEP 2: The product of Step 1 B (183 mg, 0.77 mmol) and the product of Example 2, Step 2 (90 mg, 0.38 mmol) were combined as in Example 32 to afford a solid C. Mass spectrum (ESI): 439.1, $^1$H NMR ($CD_3OD$) δ 7.68 (s, 1H), 7.21 (t, 1H), 7.09 (m, 2H), 6.98 (d, 2H), 6.88 (t, 1H), 6.60 (m, 1H), 5.80 (s, 1H), 4.80 (s, 2H), 4.18 (m, 2H), 3.77 (m, 4H), 3.62 (t, 2H), 3.42 (s, 3H), 3.34 (s, 3H)

The following compounds were prepared in a similar manner:

| COMPOUND | STRUCTURE | M + 1 (ESI) |
|---|---|---|
| 165 | 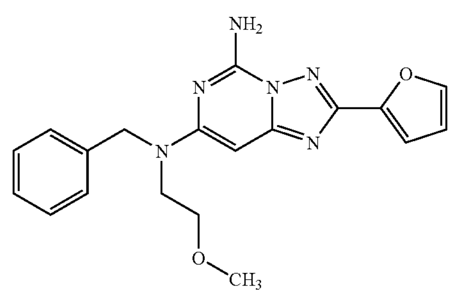 | 365.1 |
| 166 | 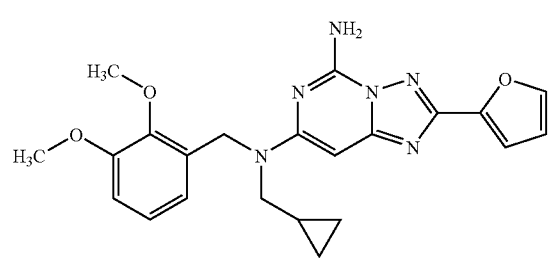 | 361.1 |

-continued
| COMPOUND | STRUCTURE | M + 1 (ESI) |
|---|---|---|
| 167 | 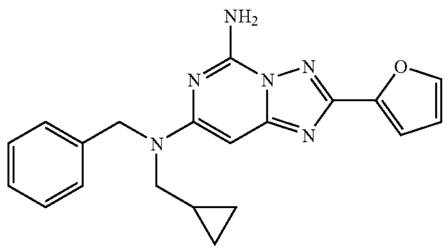 | 425.1 |
| 168 | 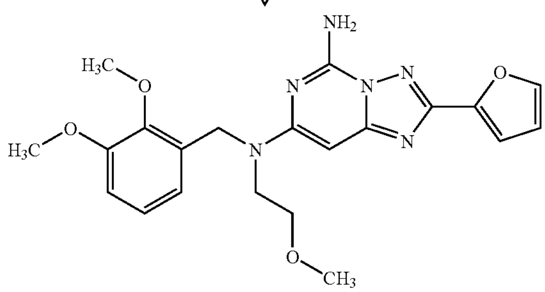 | 421.1 |
| 169 | 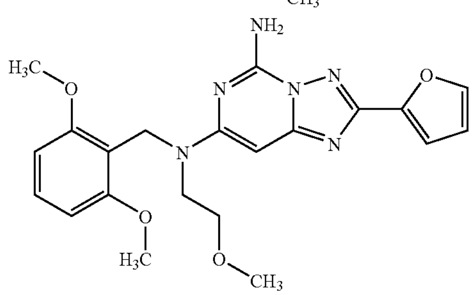 | 425.1 |
| 170 | 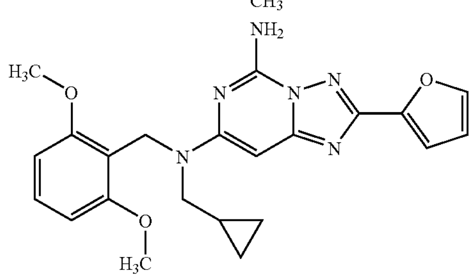 | 421.1 |
Example 38
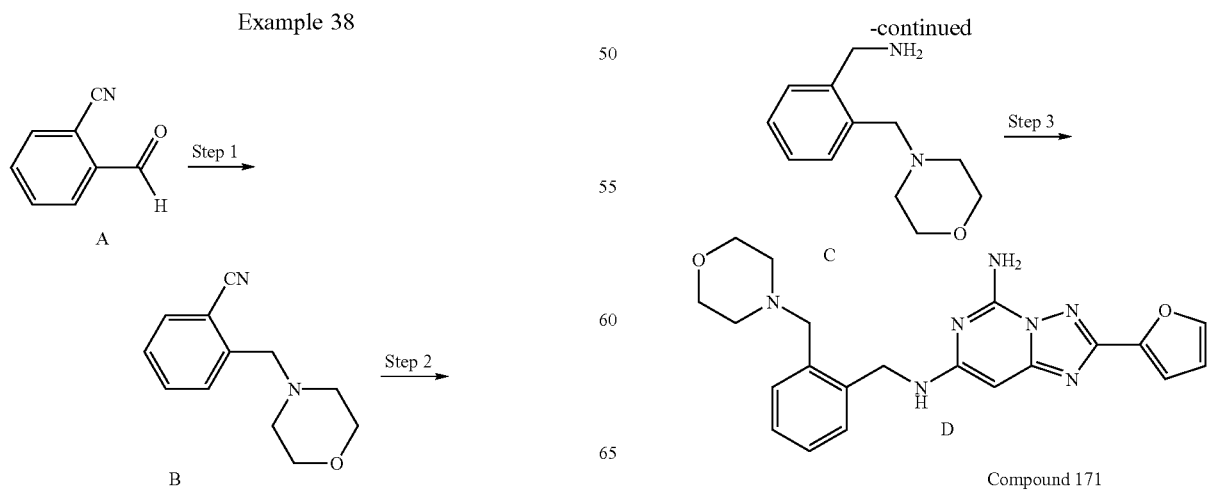
Compound 171

STEP 1: 2-cyanobenaldehyde (500 mg, 3.8 mmol), morpholine (365 mg, 4.2 mmol), and NaBH(OAc)$_3$ (1.21 g, 5.72 mmol) were combined in THF (20 mL). The mixture was stirred for 20 h at room temperature under N$_2$. The mixture was quenched with 1 N NaOH and partitioned between H$_2$O and EtOAc. The organics were washed with H$_2$O and brine, and then dried over MgSO$_4$, filtered, concentrated in vacuo, and chromarographed to afford an oil B. Mass spectrum (ESI): 203.0

STEP 2: The product of Step 1 (172 mg, 0.85 mmol) was hydrogenated as in Example 34, Step 2 to afford an oil C. Mass spectrum (ESI): 207.0

STEP 3: The product of Step 2 C (160 mg, 0.77 mmol) was combined with the product of Example 2, Step 2 (90 mg, 0.38 mmol) as in Example 32 to afford a solid D. Mass spectrum (ESI): 406.1 $^1$H NMR (CD$_3$OD) δ 7.69 (s, 1H), 7.41 (d, 1H), 7.24 (m, 3H), 7.11 (s, 1H), 6.61 (m, 1H), 5.77 (s, 1H), 4.60 (s, 2H), 3.74 (t, 4H) 3.59 (s, 2H), 2.48 (s, 4H)

Example 39

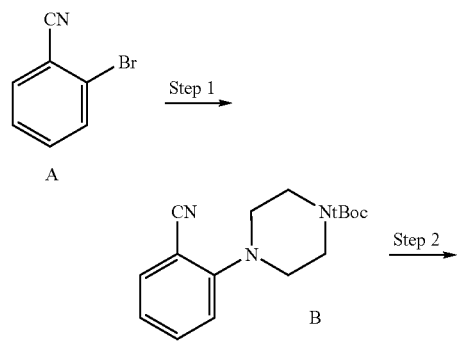

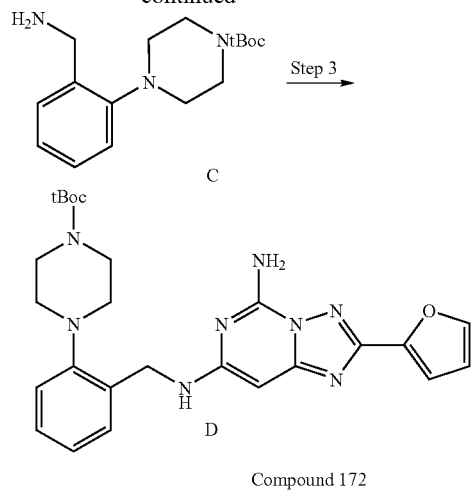

Compound 172

STEP 1: 2-bromobenzonitrile (3 g, 16.5 mmol) and tbutyl 1-piperazine carboxylate (3.68 g, 19.8 mmol) were combined as in Example 10, Step 1 (except reflux time is 20 h and the crude product is chromatographed) to afford an oil B. $^1$H NMR (CD$_3$OD) δ 7.60 (m, 2H), 7.14 (m, 2H), 3.62 (s, 4H), 3.14 (t, 4H), 1.49 (s, 9H)

STEP 2: The product of Step 1 (440 mg, 1.53 mmol) was hydrogenated as in Example 34, Step 2 to afford an oil C. Mass spectrum (ESI): 292.0

STEP 3: The product of Step 2 C (477 mg, 1.64 mmol) and the product of Example 2, Step 2 (193 mg, 0.82 mmol) were combined as in Example 32 to afford a solid D. Mass spectrum (ESI): 491.1, $^1$H NMR (CD$_3$OD) δ 7.68 (s, 1H), 7.39 (d, 1H), 7.24–7.06 (m, 4H), 6.60 (m, 1H), 5.69 (s, 1H), 4.57 (s, 2H), 3.62 (bs, 4H), 2.91 (bs, 4H), 1.48 (s, 9H)

The following compound was prepared in a similar manner:

| COMPOUND | STRUCTURE | M + 1 (ESI) |
|---|---|---|
| 173 | 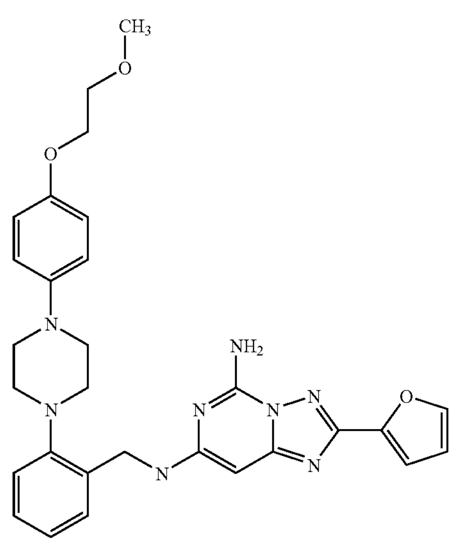 | 541.1 |

Example 40

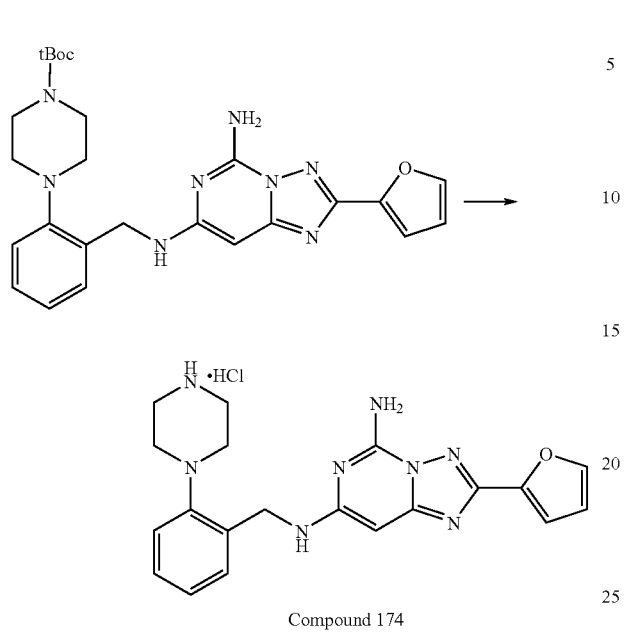

Compound 174

The product from Example 39, Step 3 (150 mg, 0.31 mmol), 4 M HCl/dioxane (1 mL), and dioxane were combined (2 mL). The mixture was stirred for 20 h at room temperature, under $N_2$, then concentrated in vacuo. The residue was suspended in $Et_2O$, reconcentrated in vacuo, and repeated several times. The resultant solid was taken up in $Et_2O$, filtered, and dried (vacuum oven, 50° C.) to afford a solid. Mass spectrum (ESI): 391.1, $^1$H NMR ($CD_3OD$) δ 7.91 (s, 1H), 7.43–7.17 (m, 6H), 6.78 (m, 1H), 3.66 (s, 2H), 3.43 (bs, 4H), 3.20 (m, 4H)

Example 41

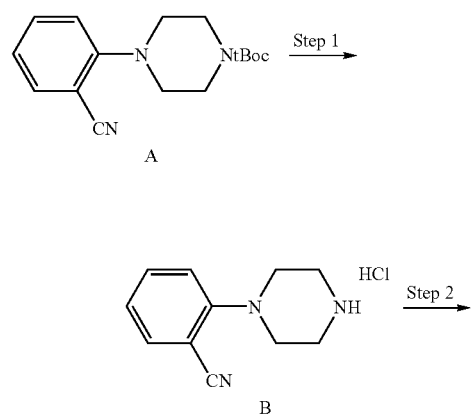

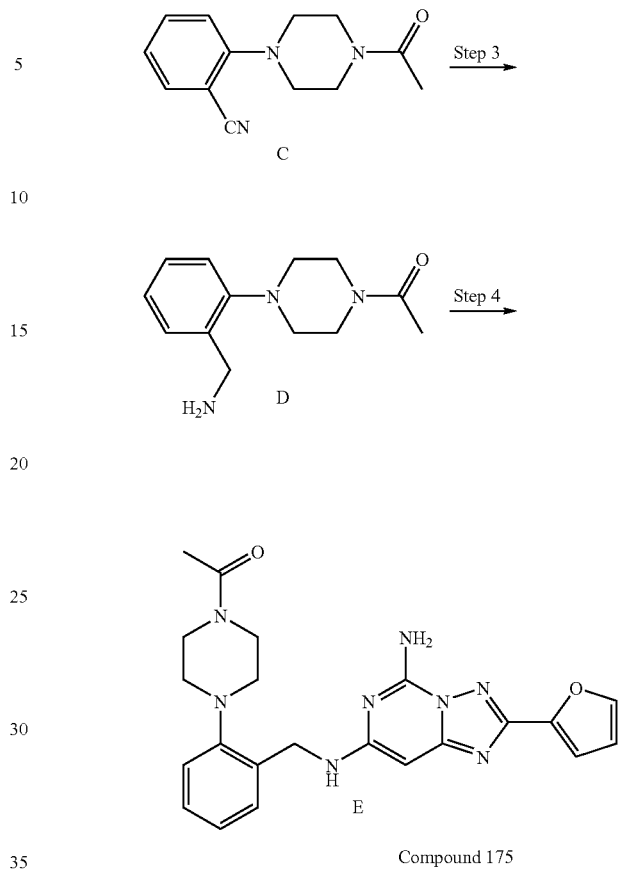

Compound 175

STEP 1: The product from Example 39, step 1 (1.11 g, 4.1 mmol) was deprotected, as in Example 40 to afford a solid B. Mass spectrum (ESI): 188.0

STEP 2: The free base of the product from Step 1 B (200 mg, 1.1 mmol), triethylamine (130 mg, 1.3 mmol), and acetic anhydride (4 mL) were combined. The mixture was stirred for 20 h at room temperature, under $N_2$. The mixture was concentrated in vacuo and partitioned between sat'd $NaHCO_3$ and $CH_2Cl_2$. The organics were washed with $H_2O$, brine, and dried over $MgSO_4$, filtered, and concentrated in vacuo to afford an oil C, which was carried on without further purification. Mass spectrum (ESI): 230.0

STEP 3: The product of Step 2 C (230 mg, 1.0 mmol) was hydrogenated as in Example 34, Step 2 to afford an oil D. Mass spectrum (ESI): 234.0

STEP 4: The product of Step 3 D (235 mg, 1.0 mmol) and the product of Example 2, Step 2 (119 mg, 0.50 mmol) were combined as in Example 32 to afford a solid E. Mass spectrum (ESI): 433.1, $^1$H NMR ($CD_3OD$) δ 7.68 (s, 1H), 7.40 (d, 1H), 7.24–7.10 (m, 4H), 6.60 (m, 1H), 5.70 (s, 1H), 4.60 (s, 2H), 3.78 (bs, 2H), 3.73 (t, 2H), 2.96 (dt, 4H), 2.15 (s, 3H)

The following compounds were prepared in a similar manner:

| COMPOUND | STRUCTURE | M + 1 (ESI) |
|---|---|---|
| 176 | 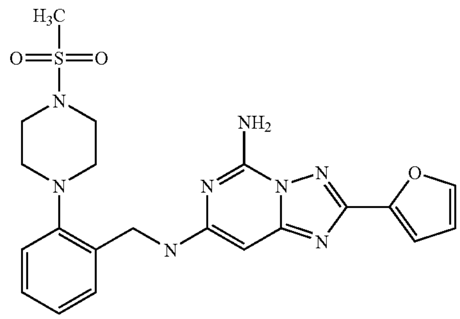 | 569.1 |
| 177 | 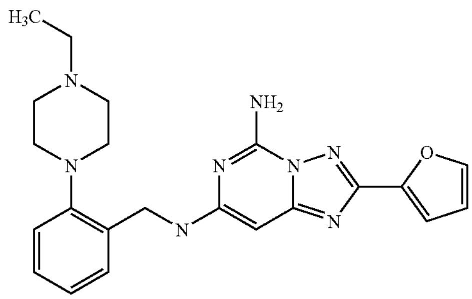 | 419.1 |
Preferred compounds of this invention include, but are not limited to, the following compounds selected from the group consisting of:
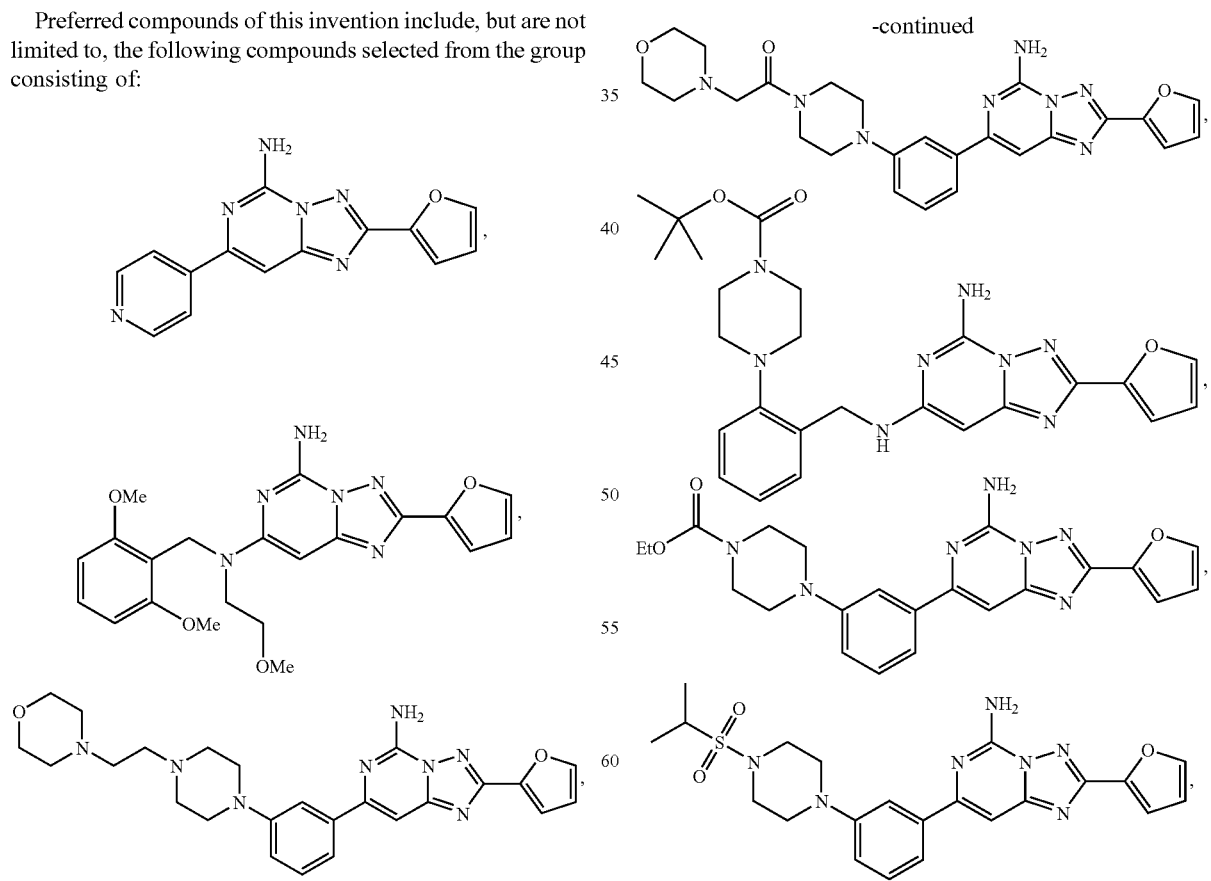

Example 42

The pharmacological activity of the compounds of the invention is determined by the following in vitro and in vivo assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/mL methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175–200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275–300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 1971, 6-OHDA and Cathecolamine Neurons, North Holland, Amsterdam, 101–127), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µl of saline with 0.05% ascorbic acid as antioxidant, and infused at the constant flow rate of 1 µl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Example 43

The following are examples of pharmaceutical dosage forms which contain a compound of the invention.

Pharmaceutical Dosage Form Examples

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the structural formula I

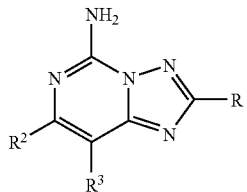

or a pharmaceutically acceptable salt thereof; wherein:

R is selected from the group consisting of $R^4$-heteroaryl, $R^5$-phenyl, $(C_4-C_6)$cycloalkenyl, —C(=CH$_2$)CH$_3$, —C≡C—CH$_3$,

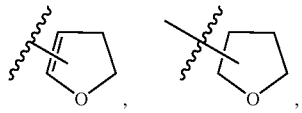

—CH=C(CH$_3$)$_2$,

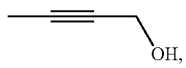

and —CH=CH—CH$_3$;

$R^2$ is selected from the group consisting of —W—X, —NR$^{19}$(CH$_2$)$_m$—W—X, and —NR$^{19}$CH(CH$_3$)—W—X;

$R^3$ is hydrogen;

$R^4$ is 1 to 3 substituents, which can be the same or different, and are independently selected from the group consisting of hydrogen, $(C_1-C_6)$-alkyl, —CF$_3$, halogen, —NO$_2$, —NR$^{15}$R$^{16}$, $(C_1-C_6)$alkoxy, $(C_1-C_6)$alkylthio, $(C_1-C_6)$alkylsulfinyl, $(C_1-C_6)$alkylsulfonyl, —COOR$^{17}$ and —C(O)NR$^6$R$^7$;

$R^5$ is 1 to 5 substituents, which can be the same or different, and are independently selected from the group consisting of hydrogen, halogen, $(C_1-C_6)$alkyl, hydroxy, $(C_1-C_6)$alkoxy, —CN, —NH$_2$, $(C_1-C_6)$alkylamino, di-$((C_1-C_6)$alkyl)amino, —CF$_3$, —OCF$_3$, —S(O)$_{0-2}(C_1-C_6)$alkyl and —CH$_2$—SO$_2$-phenyl;

$R^6$ and $R^7$, which can be the same or different, are each independently selected from the group consisting of hydrogen and $(C_1-C_6)$alkyl;

$R^8$ is 1 to 5 substituents, which can be the same or different, and are independently selected from the group consisting of hydrogen, halogen, $(C_1-C_6)$alkyl, hydroxy, $C_1-C_6$ alkoxy, —CN, amino, di-$((C_1-C_6)$alkyl)amino, —CF$_3$, —OCF$_3$, acetyl, —NO$_2$, hydroxy$(C_1-C_6)$alkoxy, $(C_1-C_6)$-alkoxy$(C_1-C_6)$alkoxy, di-$((C_1-C_6)$-alkoxy$)(C_1-C_6)$alkoxy, $(C_1-C_6)$-alkoxy$(C_1-C_6)$alkoxy-$(C_1-C_6)$-alkoxy, carboxy$(C_1-C_6)$-alkoxy, $(C_1-C_6)$-alkoxycarbonyl$(C_1-C_6)$alkoxy, $(C_3-C_6)$cycloalkyl$(C_1-C_6)$alkoxy, di-$((C_1-C_6)$alkyl)amino$(C_1-C_6)$alkoxy, morpholinyl, $(C_1-C_6)$alkyl-SO$_2$—, $(C_1-C_6)$alkyl-SO$_2$—$(C_1-C_6)$alkoxy, tetrahydropyranyloxy, $(C_1-C_6)$alkylcarbonyl$(C_1-C_6)$-alkoxy, $(C_1-C_6)$-alkoxycarbonyl, $(C_1-C_6)$ alkylcarbonyloxy$(C_1-C_6)$-alkoxy, —SO$_2$NH$_2$, phenoxy,

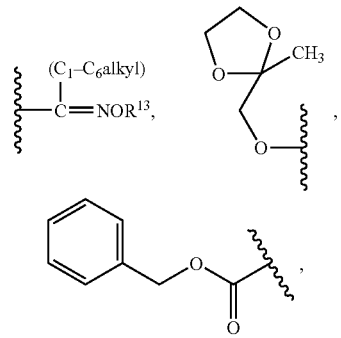

—O—CH$_2$—P(O)(OR$^6$)$_2$,— and —P(O)(OR$^6$)$_2$; or adjacent $R^8$ substituents together are —O—CH$_2$—O—, —O—CH$_2$CH$_2$—O—, —O—CF$_2$—O— or —O—CF$_2$CF$_2$—O— and form a ring with the carbon atoms to which they are attached;

$R^9$ is selected from the group consisting of $(C_1-C_6)$alkyl, $R^8$-aryl-, $R^8$-aryl$(C_1-C_6)$alkyl-, thienyl, pyridyl, $(C_3-C_6)$-cycloalkyl, $(C_1-C_6)$alkyl-OC(O)—NH—$(C_1-C_6)$alkyl-, di-$((C_1-C_6)$alkyl)aminomethyl, cycloheteroalkyl$(C_1-C_6)$alkyl, aryloxy$(C_1-C_6)$alkyl, alkoxy$(C_1-C_6)$alkyl and

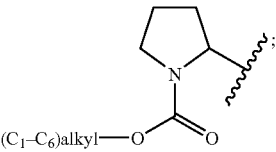

$R^{10}$ is 1–2 substituents, which can be the same or different, and are independently selected from the group consisting of hydrogen, $(C_1-C_6)$alkyl, $R^5$-aryl and $R^4$-heteroaryl, or two $R^{10}$ substituents on the same carbon can form =O;

$R^{11}$ is hydrogen or $(C_1-C_6)$alkyl; —C(O)alkyl, or $R^{17}$ and $R^{11}$ taken together are —(CH$_2$)$_p$-A-(CH$_2$)$_q$, wherein p and q are each independently 2 or 3 and A is selected from the group consisting of a bond, —CH$_2$—, —S— and —O—, and form a ring with the nitrogen to which they are attached;

$R^{12}$ is 1–2 substituents, which can be the same or different, and are independently selected from the group consisting of hydrogen, $(C_1-C_6)$alkyl, hydroxy, $(C_1-C_6)$alkoxy, halogen, and —CF$_3$;

$R^{13}$ is selected from the group consisting of H, $(C_1-C_6)$ alkyl, phenyl, benzyl, $(C_2-C_6)$alkenyl, $(C_1-C_6)$alkoxy$(C_1-C_6)$alkyl, di-$((C_1-C_6)$alkyl)amino$(C_1-C_6)$alkyl, pyrrolidinyl$(C_1-C_6)$alkyl and piperidino$(C_1-C_6)$alkyl;

$R^{14}$ is selected from the group consisting of H, halogen, $(C_1-C_6)$alkyl or $(C_1-C_6)$alkoxy;

$R^{15}$ is selected from the group consisting of H and $(C_1-C_6)$alkyl;

$R^{16}$ is selected from the group consisting of H, $(C_1-C_6)$ alkyl-C(O)— and $(C_1-C_6)$alkyl-SO$_2$—;

$R^{17}$ is selected from the group consisting of $(C_1-C_6)$alkyl, $(C_1-C_6)$hydroxyalkyl, $(C_3-C_6)$cycloalkyl, $(C_1-C_6)$alkoxy$(C_1-C_6)$alkoxy, $(C_1-C_6)$alkoxy, $(C_1-C_6)$alkoxy$(C_1-C_6)$alkyl, allyl, propargyl, $R^8$-heteroaryl-, $R^8$-aryl- and $R^8$-aryl$(C_1-C_6)$alkyl-;

$R^{18}$ is selected from the group consisting of a bond, —CH$_2$—, —CH(OH)—, —CH(CH$_3$)—, —C(CH$_3$)$_n$—, —(CH$_2$)$_n$—, and —O(CH$_2$)$_n$—, $R^{19}$ is selected from the group consisting of H, $(C_1-C_6)$ alkyl, $(C_1-C_6)$alkyl$(C_1-C_6)$cycloalkyl, $(C_1-C_6)$cycloalkyl$(C_1-C_6)$alkyl and $(C_1-C_6)$alkoxy$(C_1-C_6)$alkyl;

Q and $Q^1$ can be the same or different and are each independently selected from the group consisting of

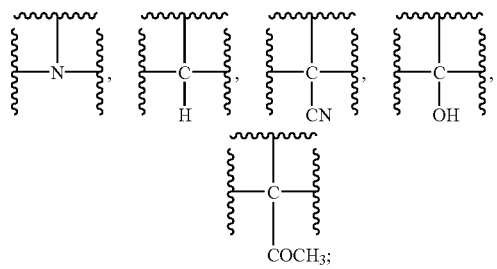
and m and n are each independently 1–3;
p and q are each independently 0–2;
s is 0–4;
W is aryl pyridyl or thienyl, and wherein said aryl, pyridyl or thienyl is optionally substituted with 1–3 substituents, which can be the same or different, and are independently selected from the group consisting of alkyl, aryl, alkylcycloalkyl, halo, hydroxy, hydroxyalkyl, alkoxy, alkylalkoxy, alkoxyalkoxy, —$NR^6R^7$, $(C_2-C_6)$alkenyl, and —CN;

X is selected from the group consisting of H, $NH_2$, —$N(R^6)(CH_2)_s$-aryl, —$N(R^6)(CH_2)_s$-heteroaryl, —$N(R^6)(CH_2)_{m+1}$—OH, and —$N(CH_3)_2$, or X is —$R^{18}$—Y-Z;

Y is selected from the group consisting of —$N(R^5)$ $CH_2CH_2N(R^7)$—, —$N(R^6)(CH_2)_n$aryl, —$OCH_2CH_2N$ $(R^6)$—, —O—, —S—, —$CH_2S$—, —$(CH_2)_{2-3}$—N $(R^6)$—, $R^8$-divalent heteroaryl,

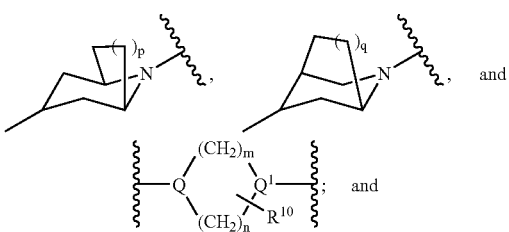
and

Z is selected from the group consisting of H, alkyl, alkoxyalkyl, $R^8$-aryl-, $R^8$-aryl$(C_1-C_6)$alkyl-, $R^8$-heteroaryl-, $R^8$-bicyclicalkyl-, aminoalkyl, alkylamino, $NH_2$, —N—$(R^6)$ $(CH_2)_s$-aryl, —$N(R^6)(CH_2)_s$-heteroaryl, —$N(R_6)C(O)$ $OR^{17}$, alkylcycloheteroalkyl, cycloheteroalkyl, cycloheteroalkylalkyl, alkoxycycloheteroalkyl, heteroaryl; $R^8$-benzofused heteroaryl-, diphenylmethyl and $R^9$—C (O)—; or when Y is

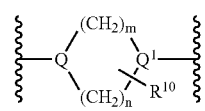

Z can also be —OH, $R^9$—$SO_2$—, $R^{17}$—$N(R^{11})(CH_2)_s$—C (O)—, $R^{17}$—OC(O)—, $R^{17}$—O$(CH_2)_n$C(O)—, benzofused heteroaryl$(CH_2)_n$C(O)—, benzofused heteroaryl$(CH_2)_n$— or $R^{17}$—$N(R^{11})$—C(S)—; or when Q is

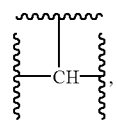

Z can also be $R^{17}R^{11}N$—, phenylamino or pyridylamino; or Z and Y taken together are selected from the group consisting of

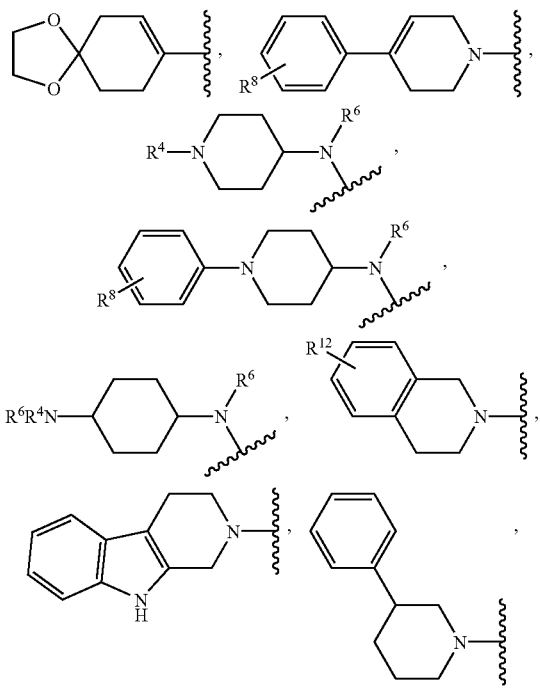

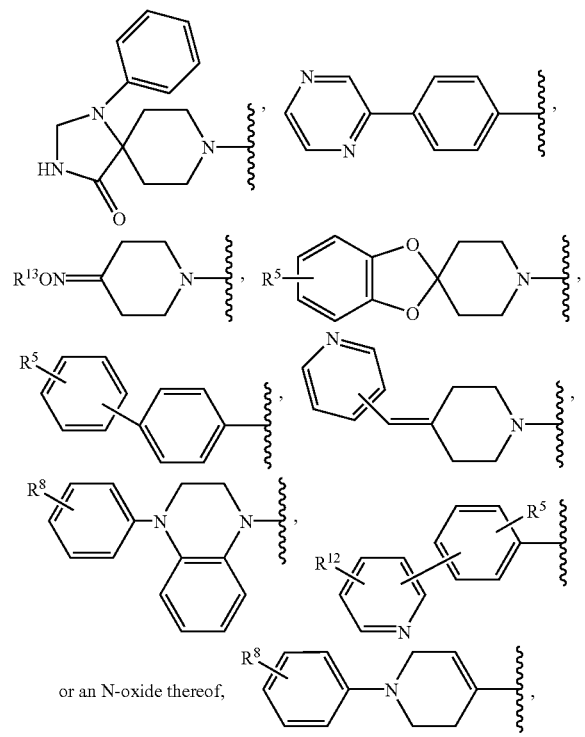

or an N-oxide thereof,

-continued
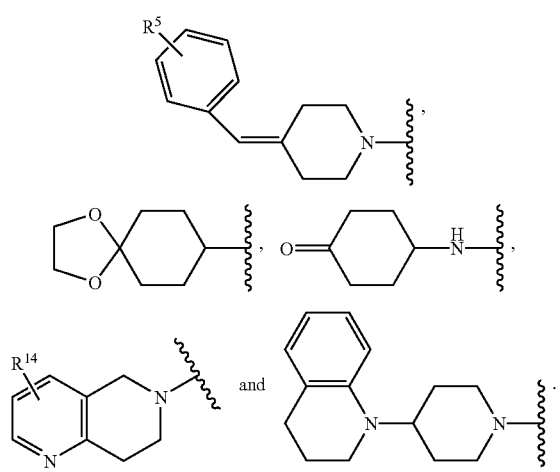
2. The compound according to claim 1 wherein R is
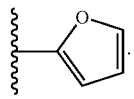
3. The compound according to claim 1 wherein $R^3$ is H.
4. The compound according to claim 1 wherein R is
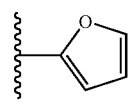
and $R^3$ is H.
5. A compound selected from the group consisting of
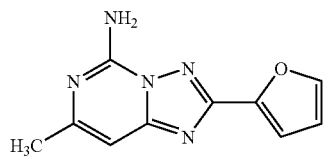
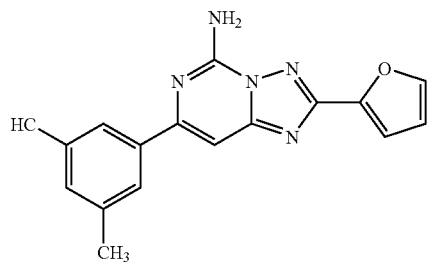
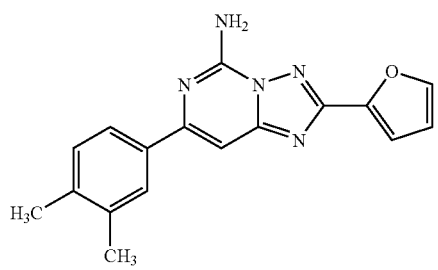
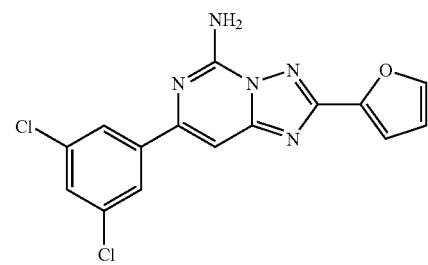
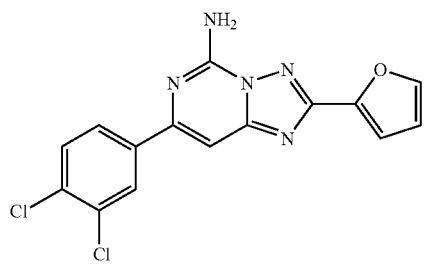
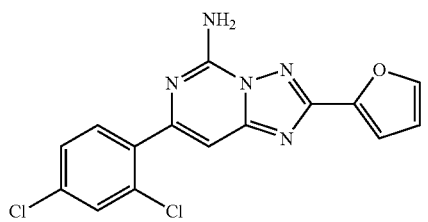
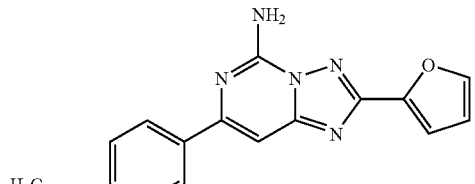
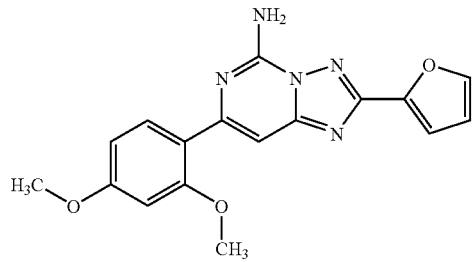

-continued
115
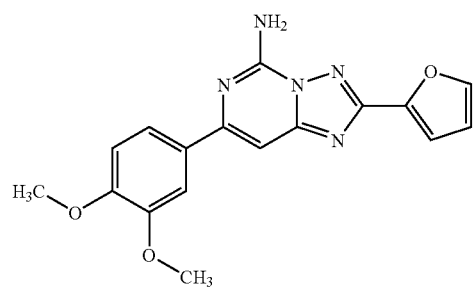
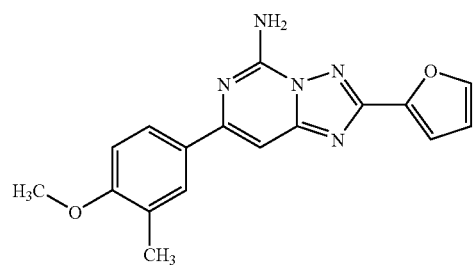
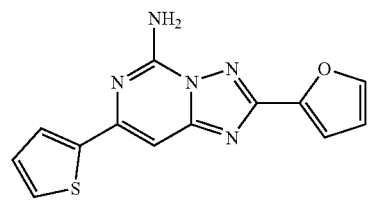
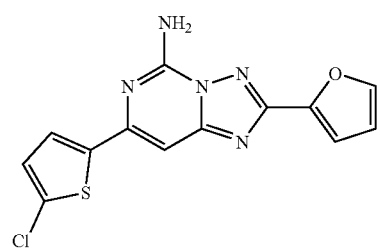
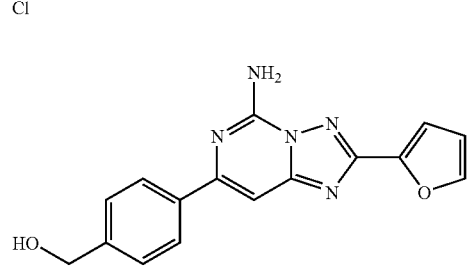
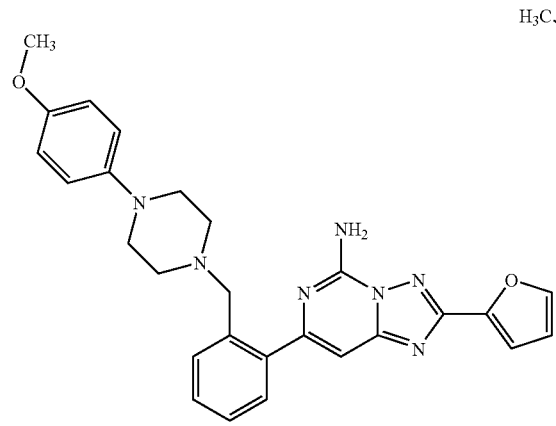
116
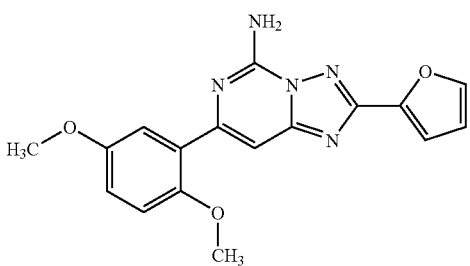
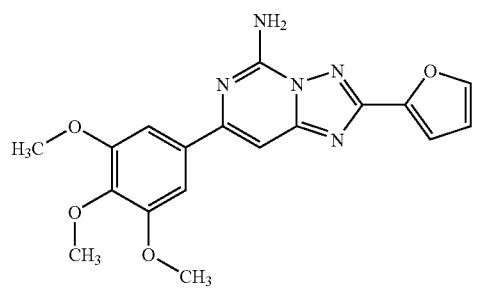
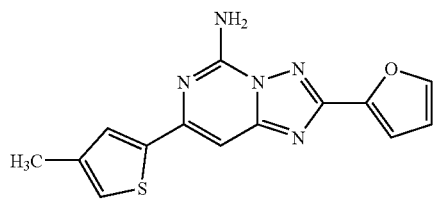
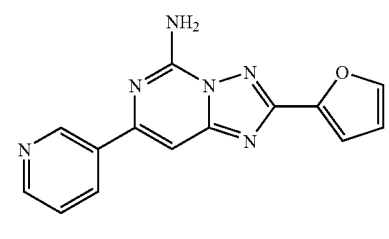
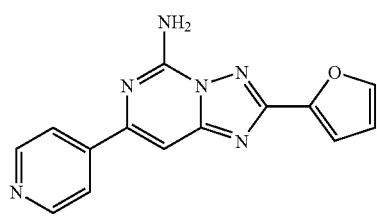
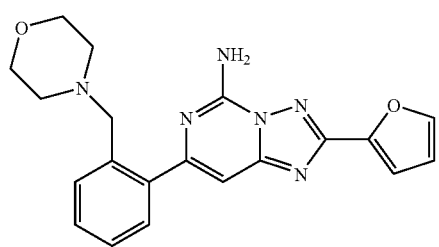
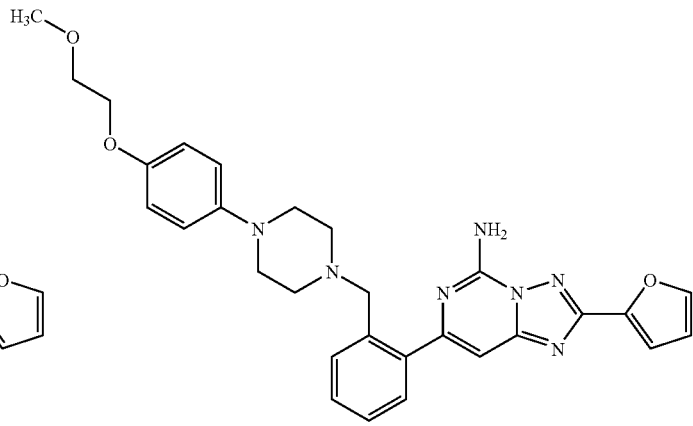

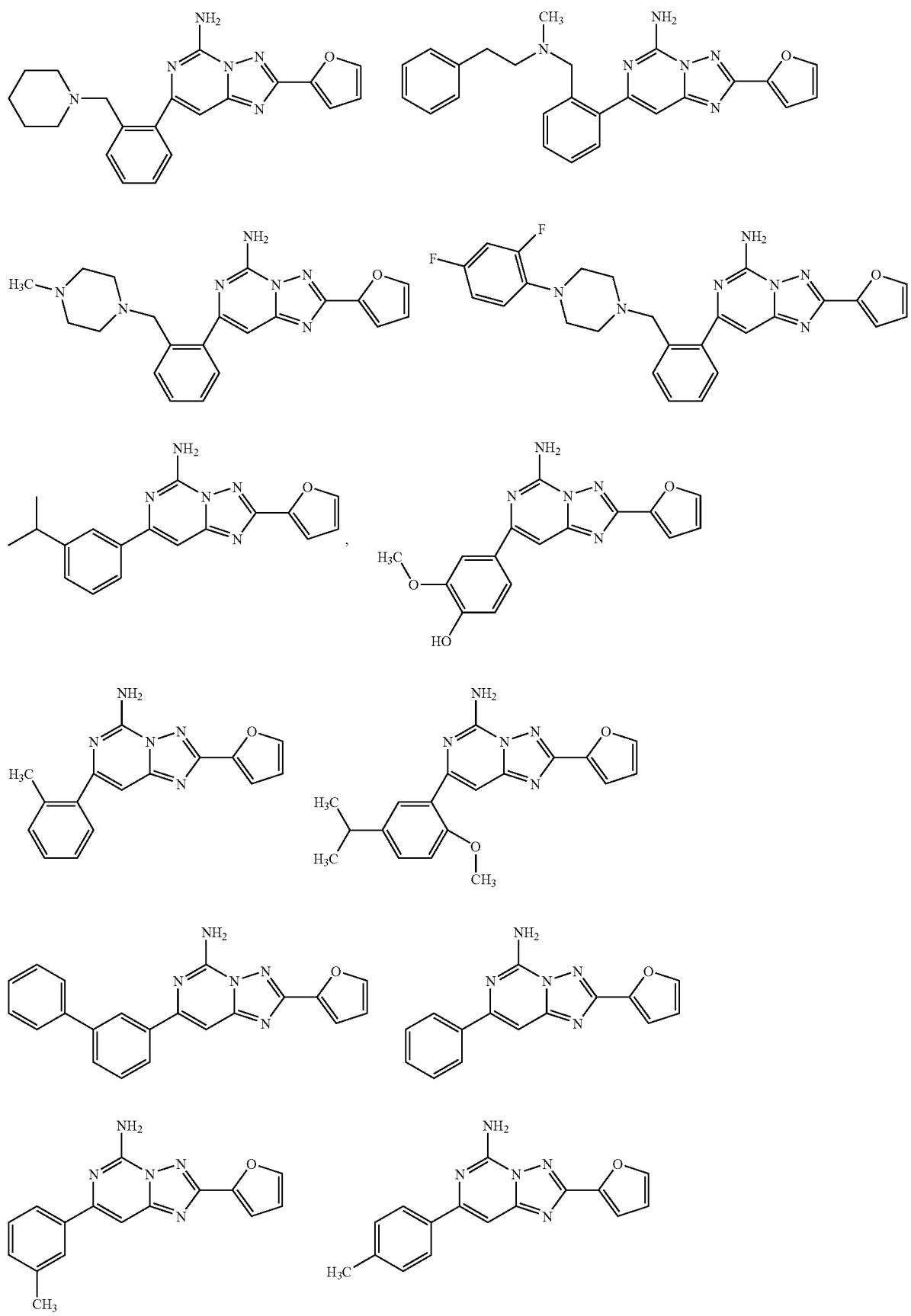

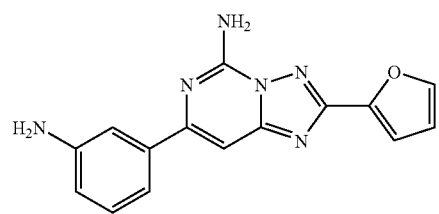
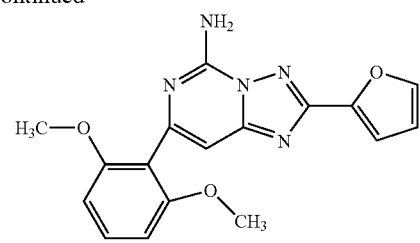
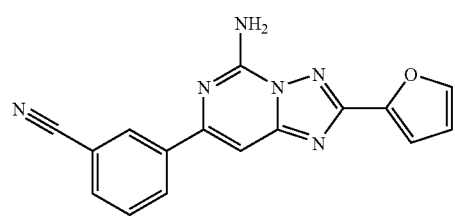
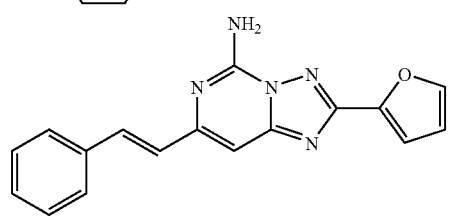
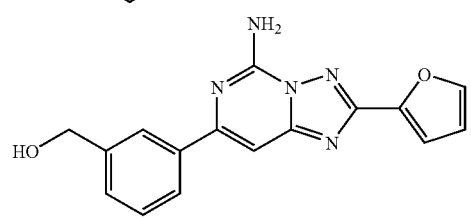
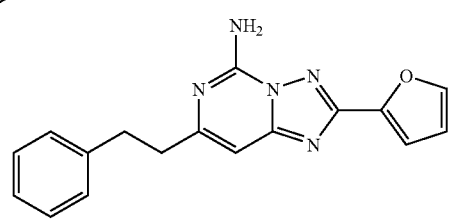
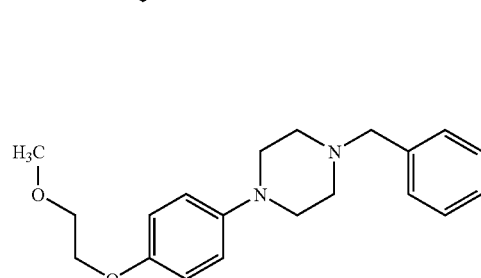
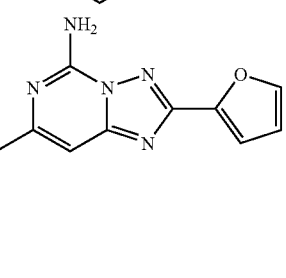
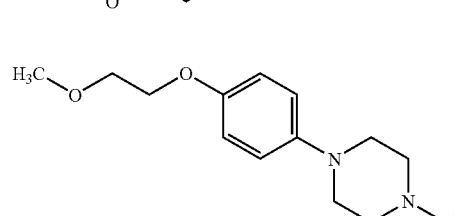
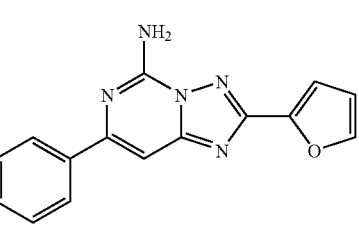
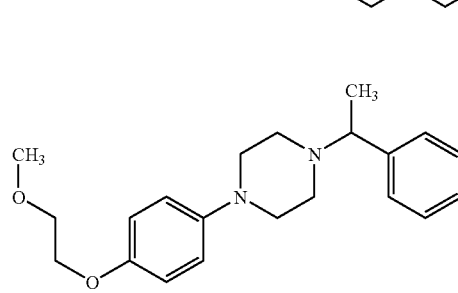
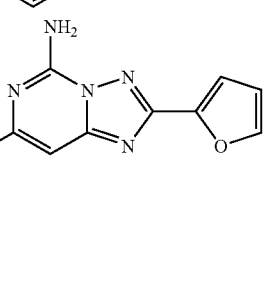
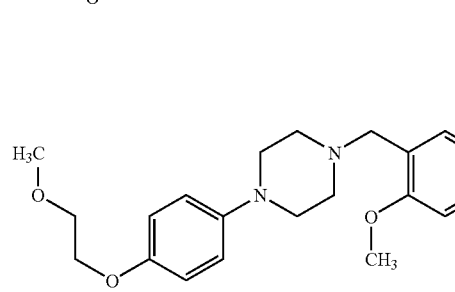
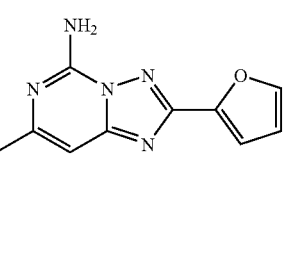

-continued
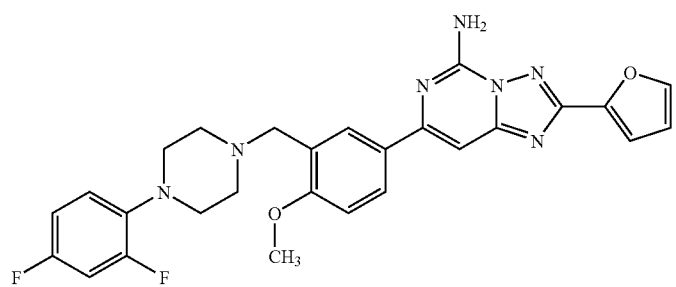
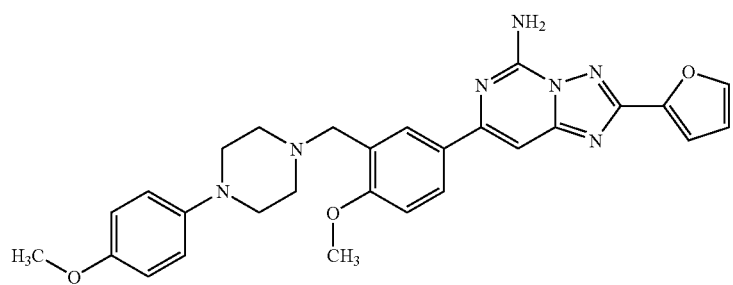
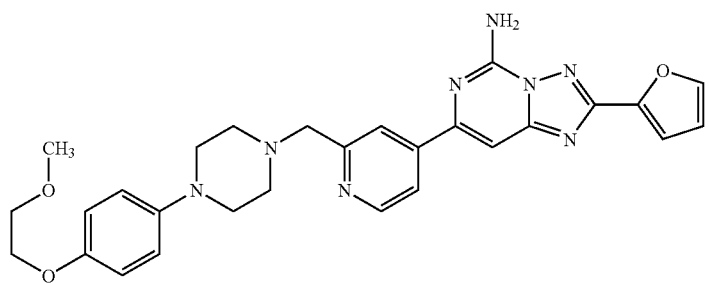
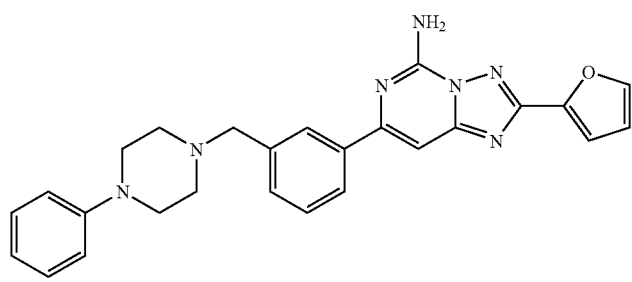
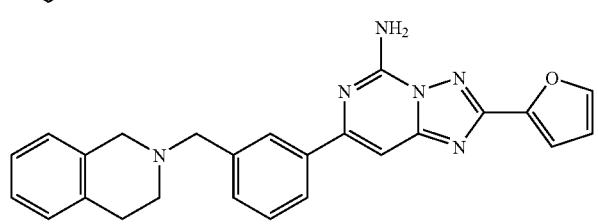
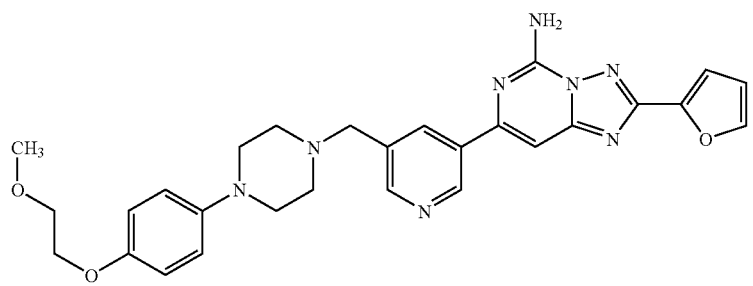

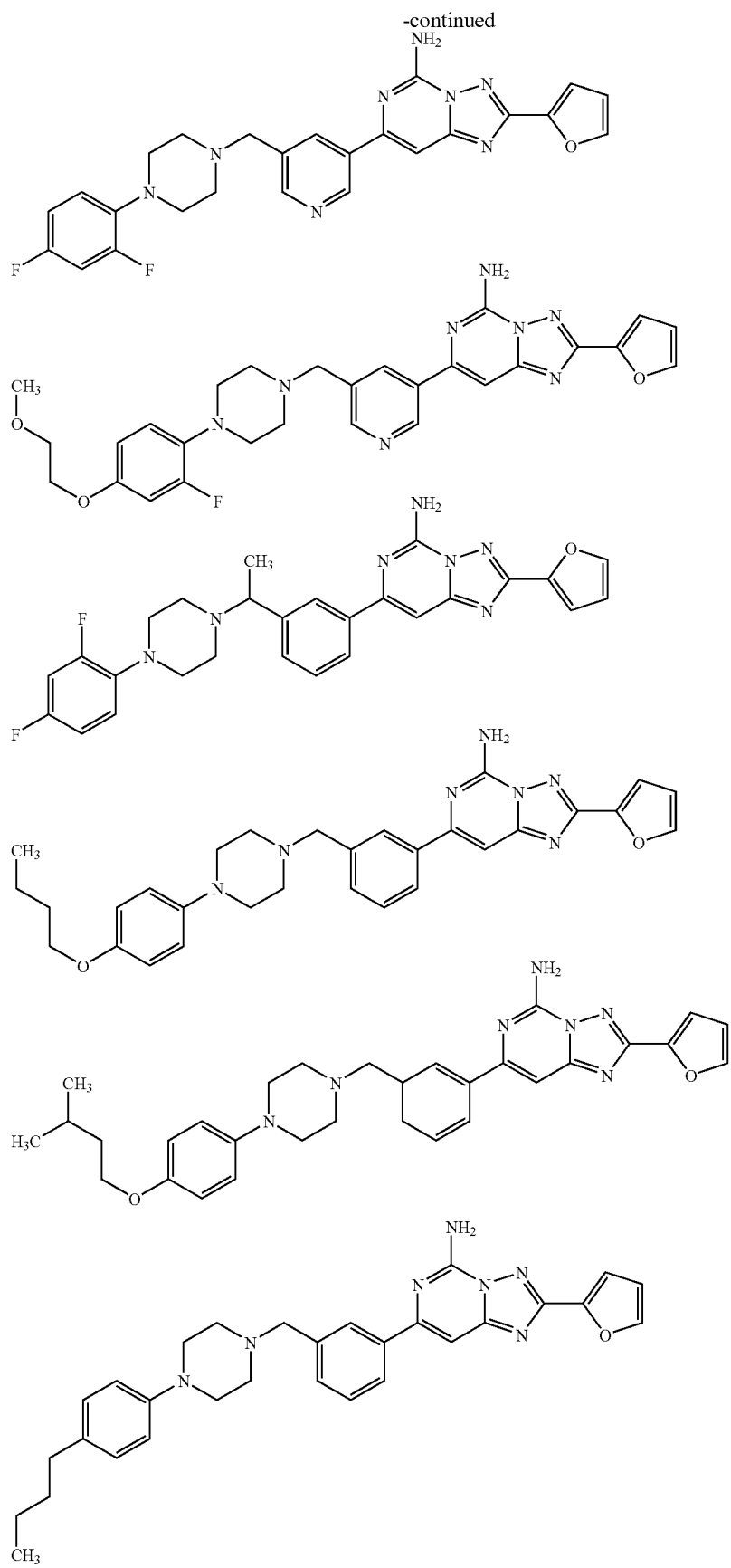

-continued
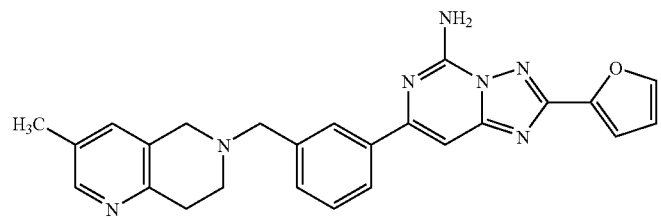
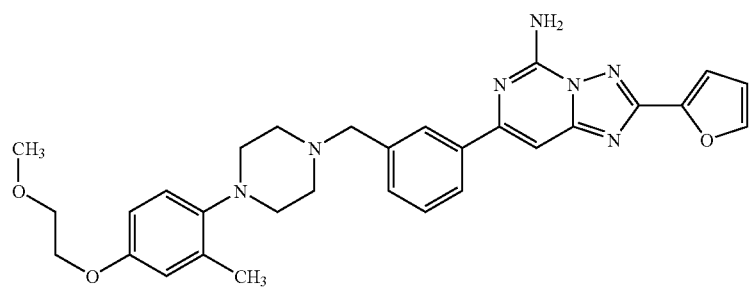
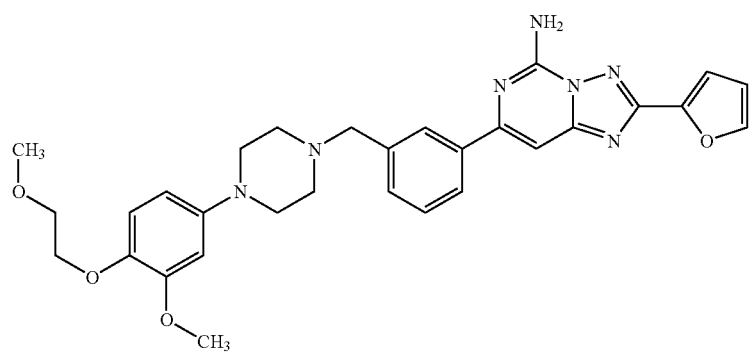
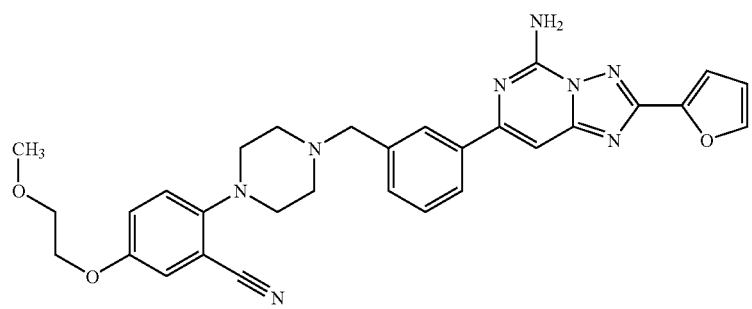
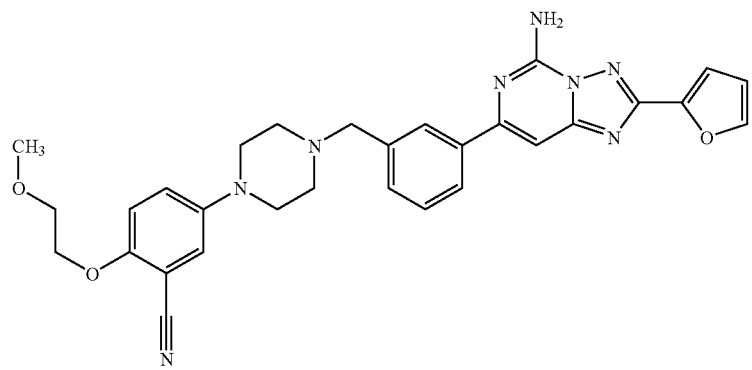

-continued
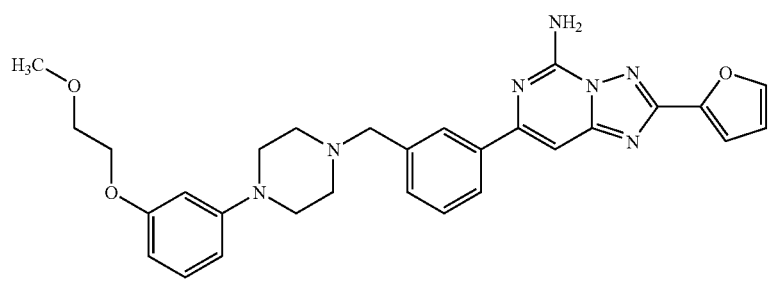
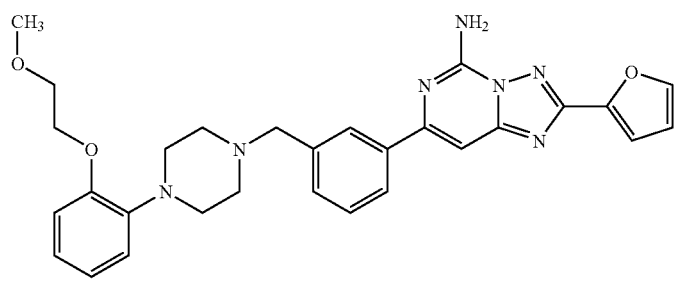
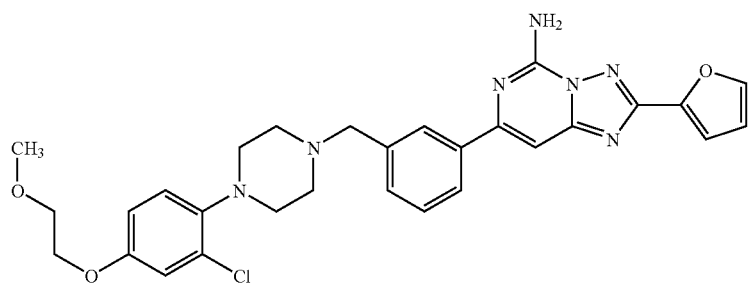
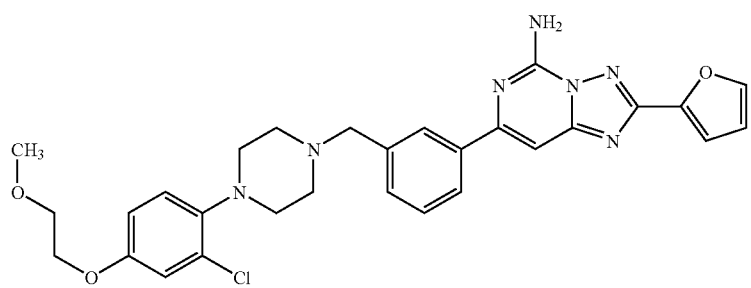
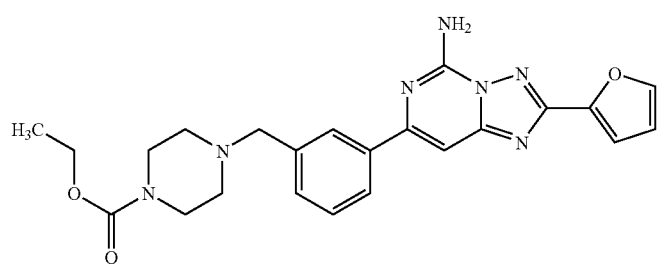
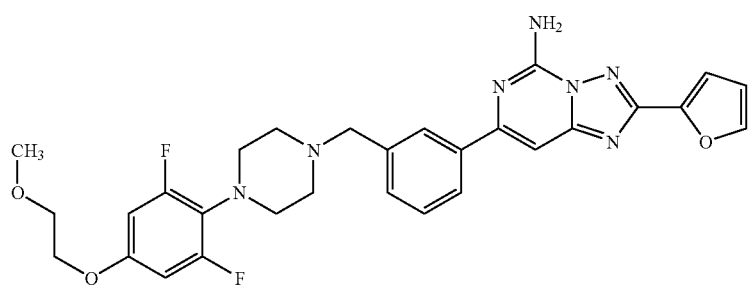

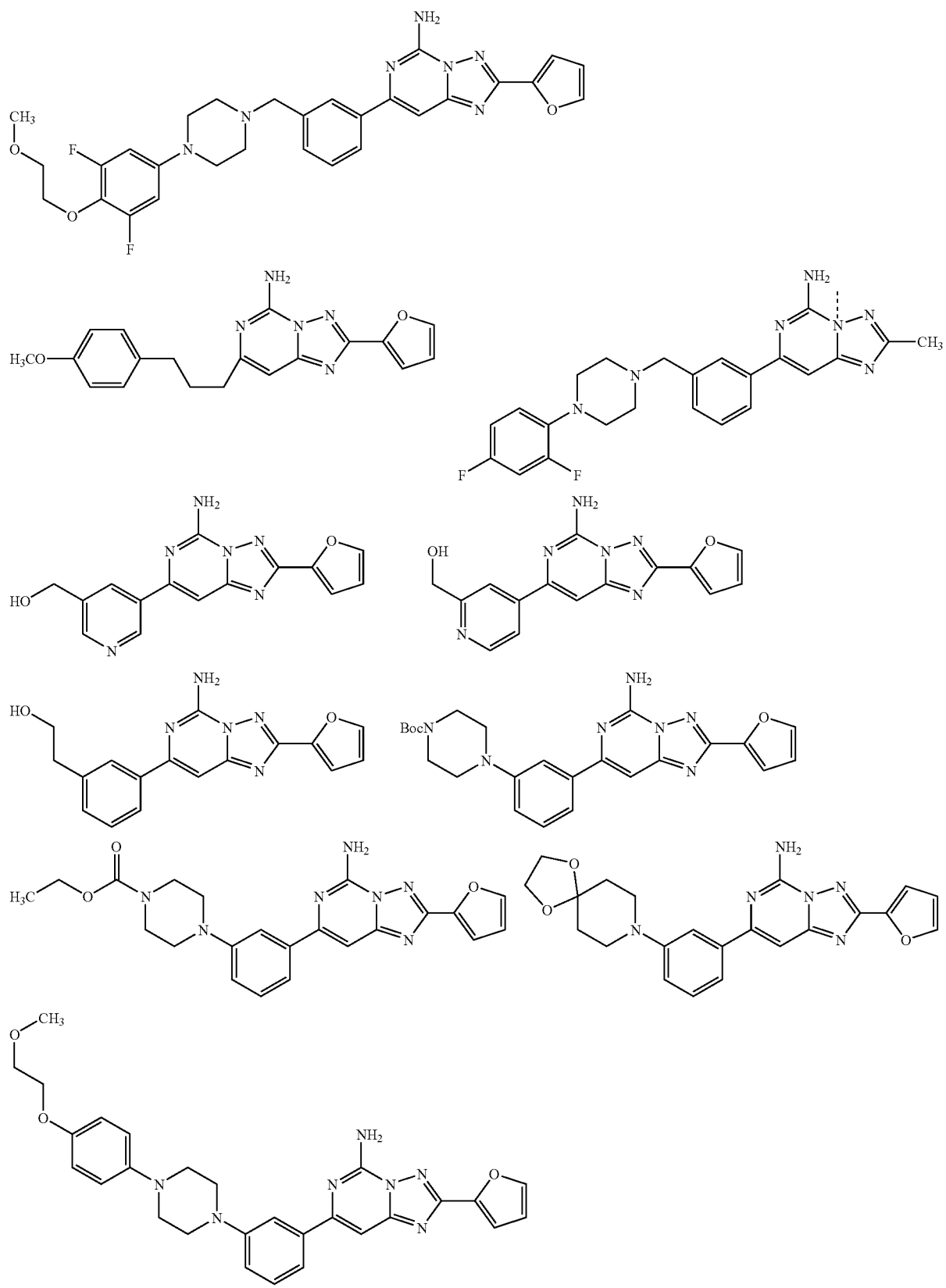

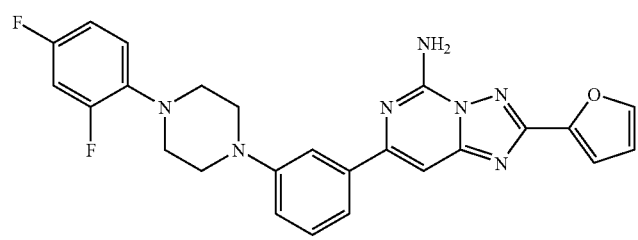
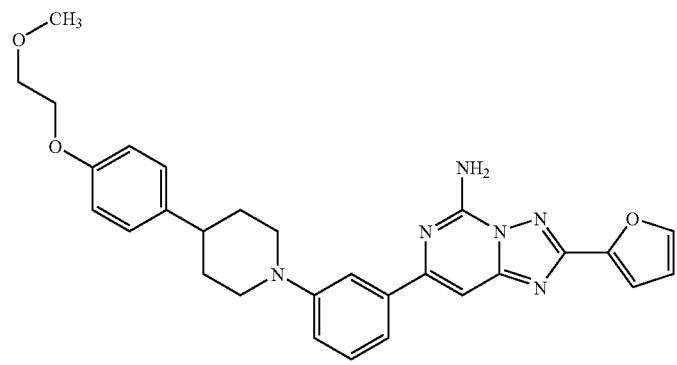
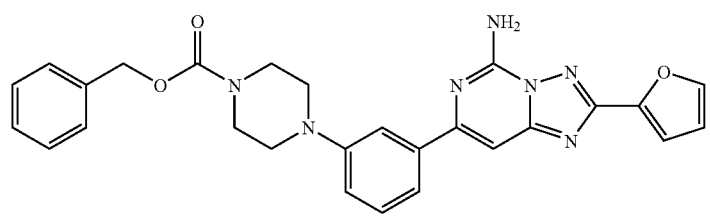
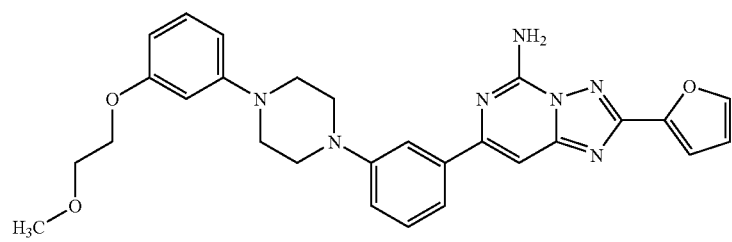
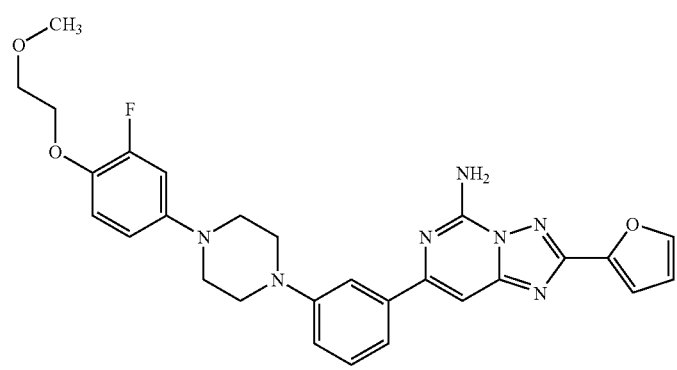
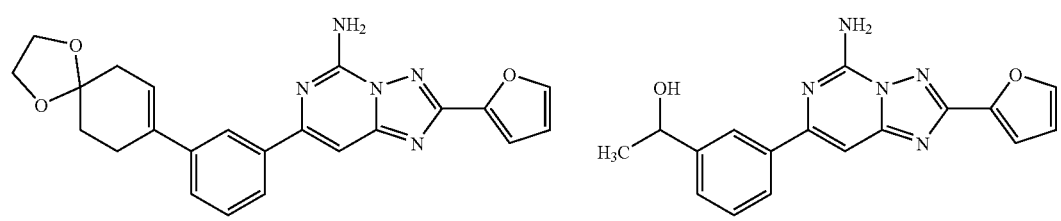

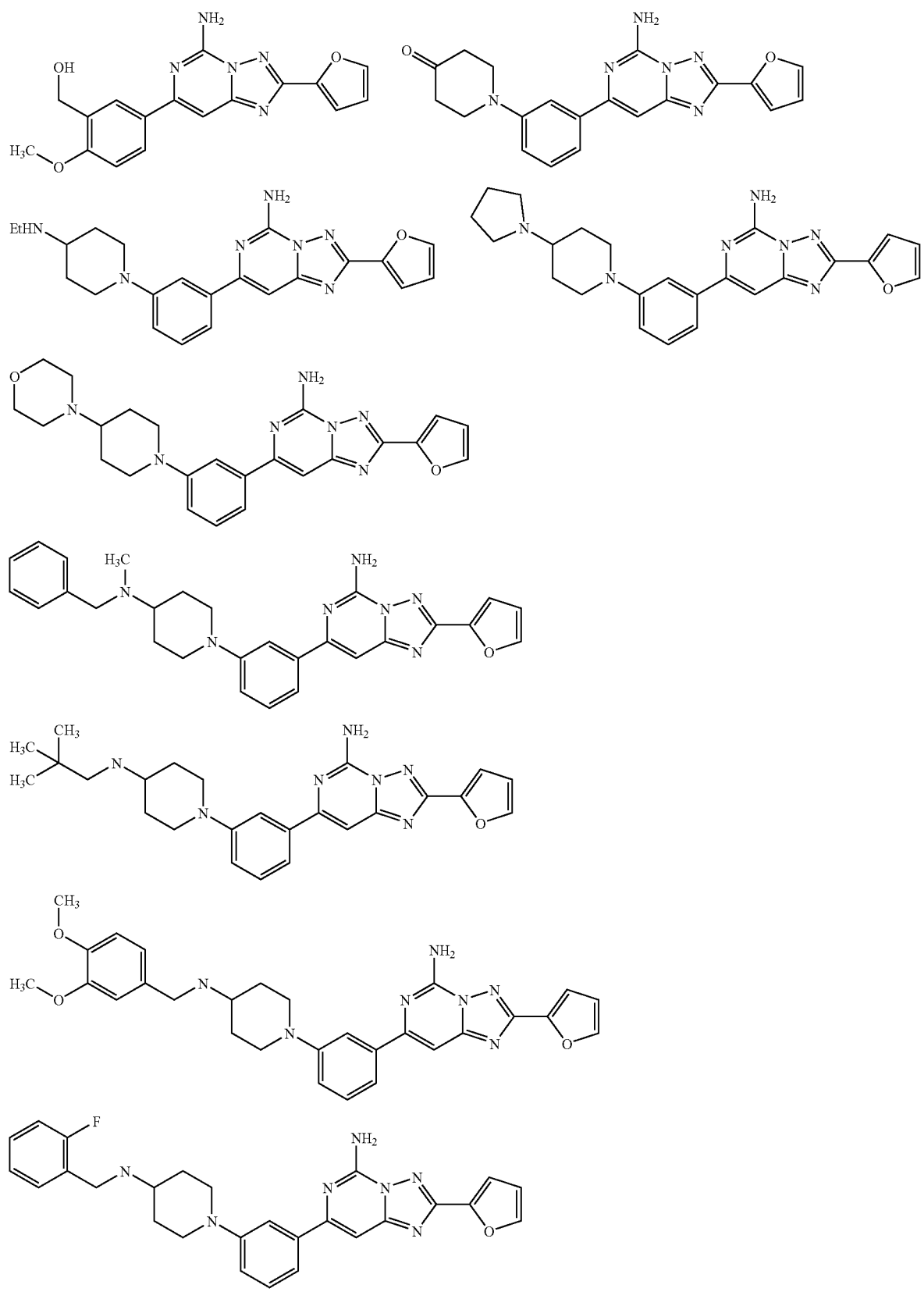

-continued
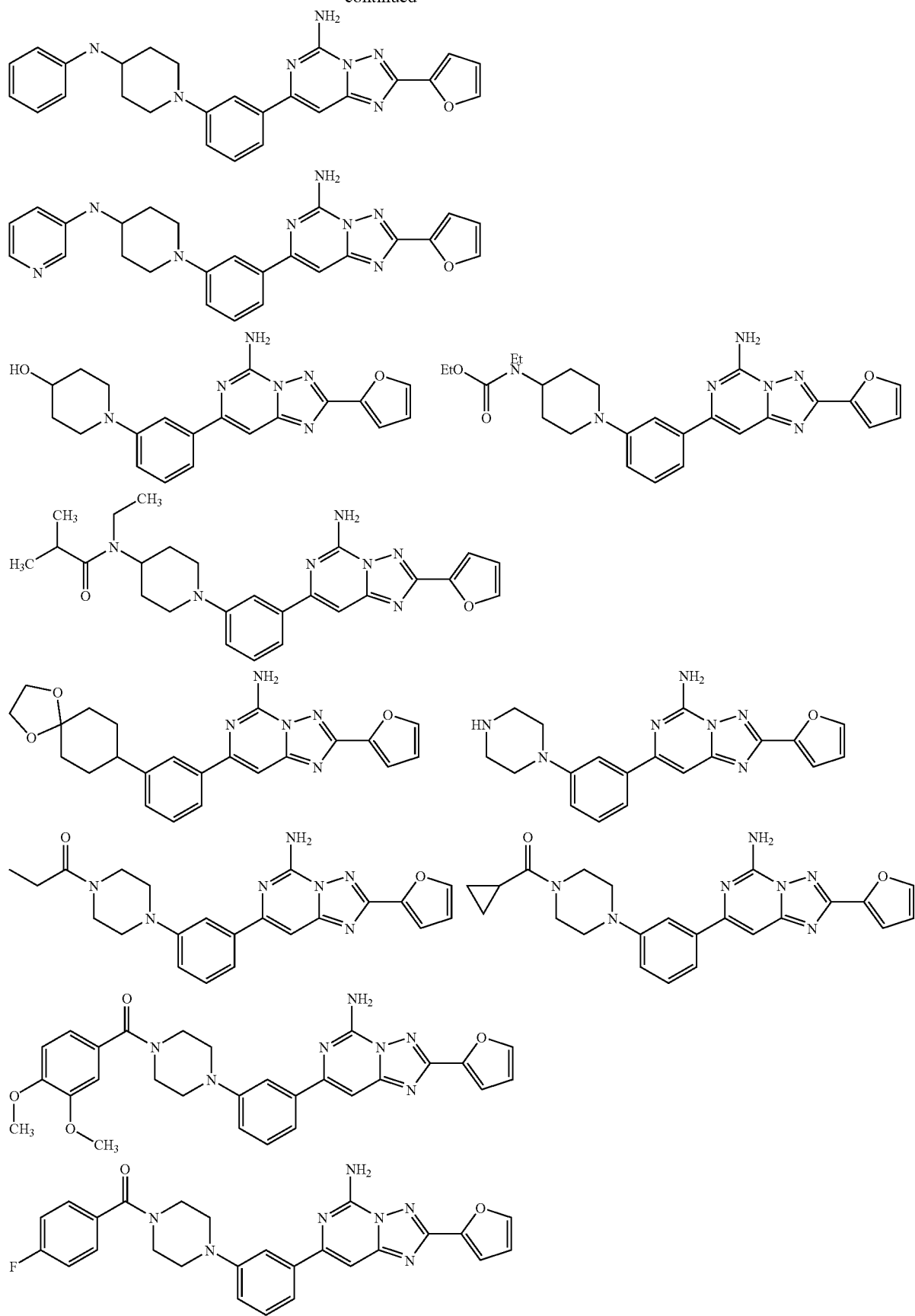

-continued
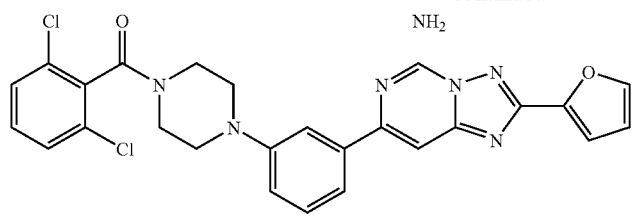
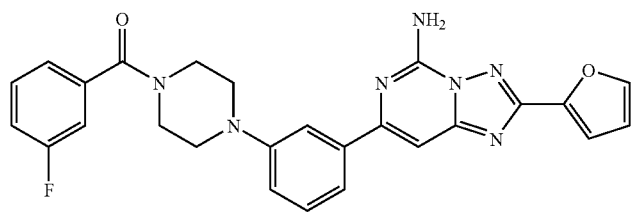
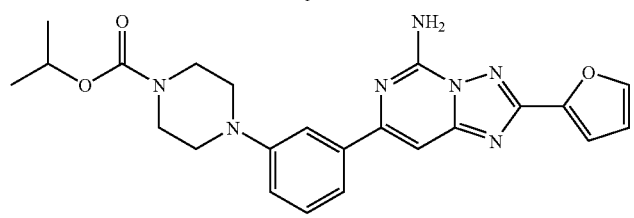
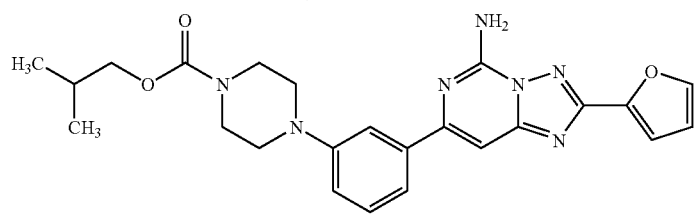
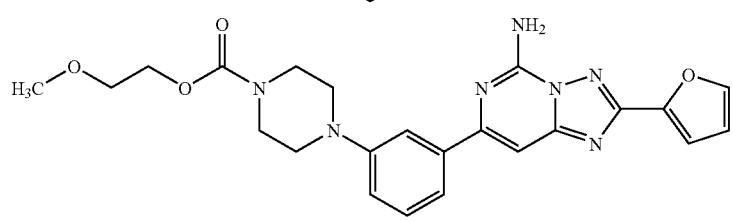
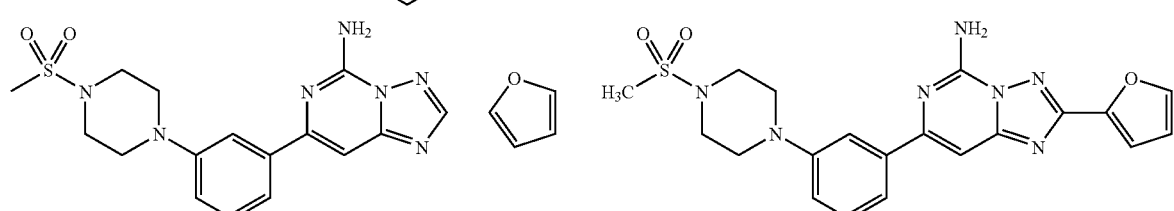
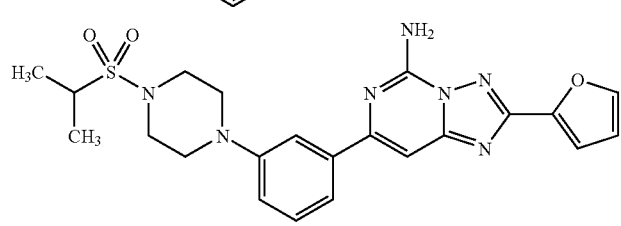
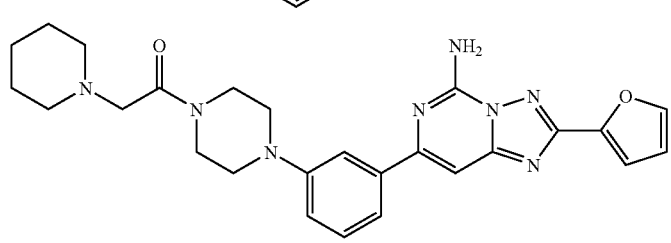

-continued
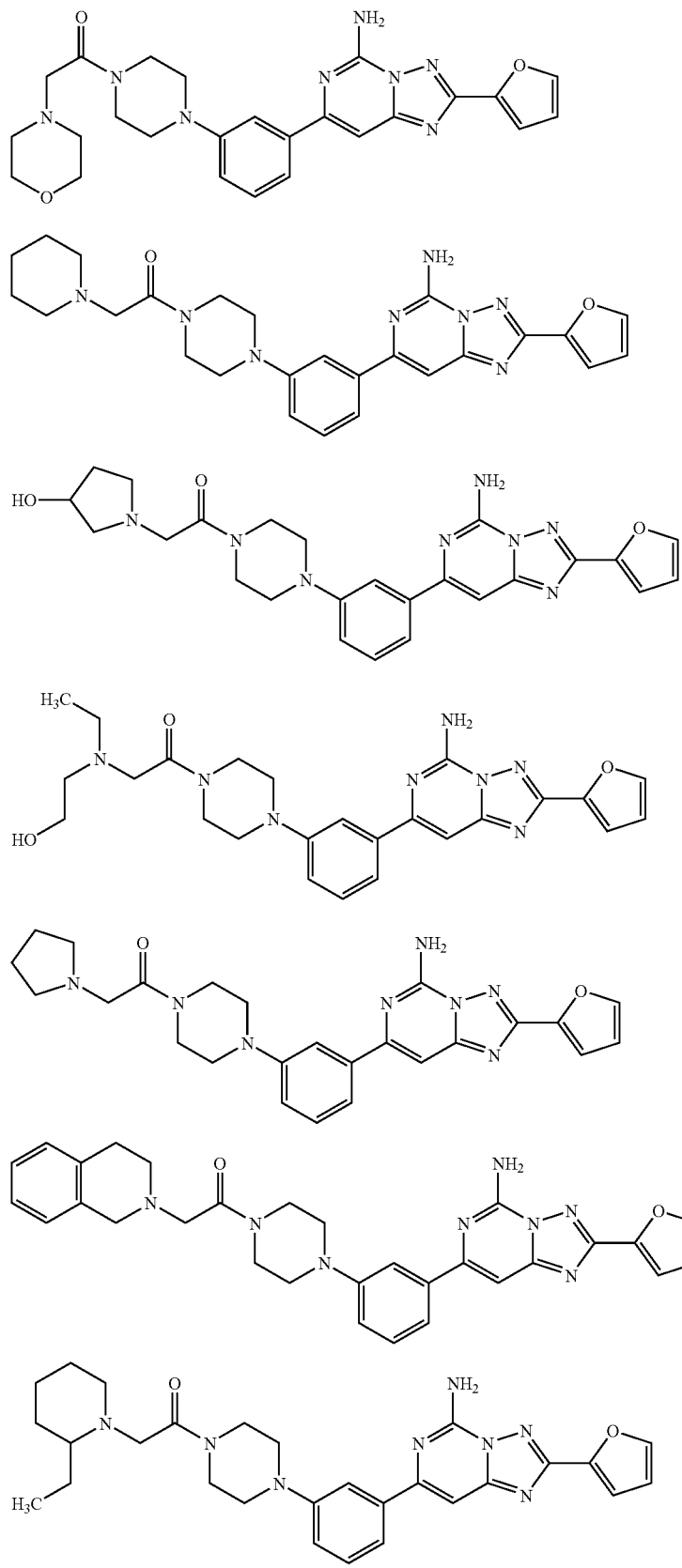

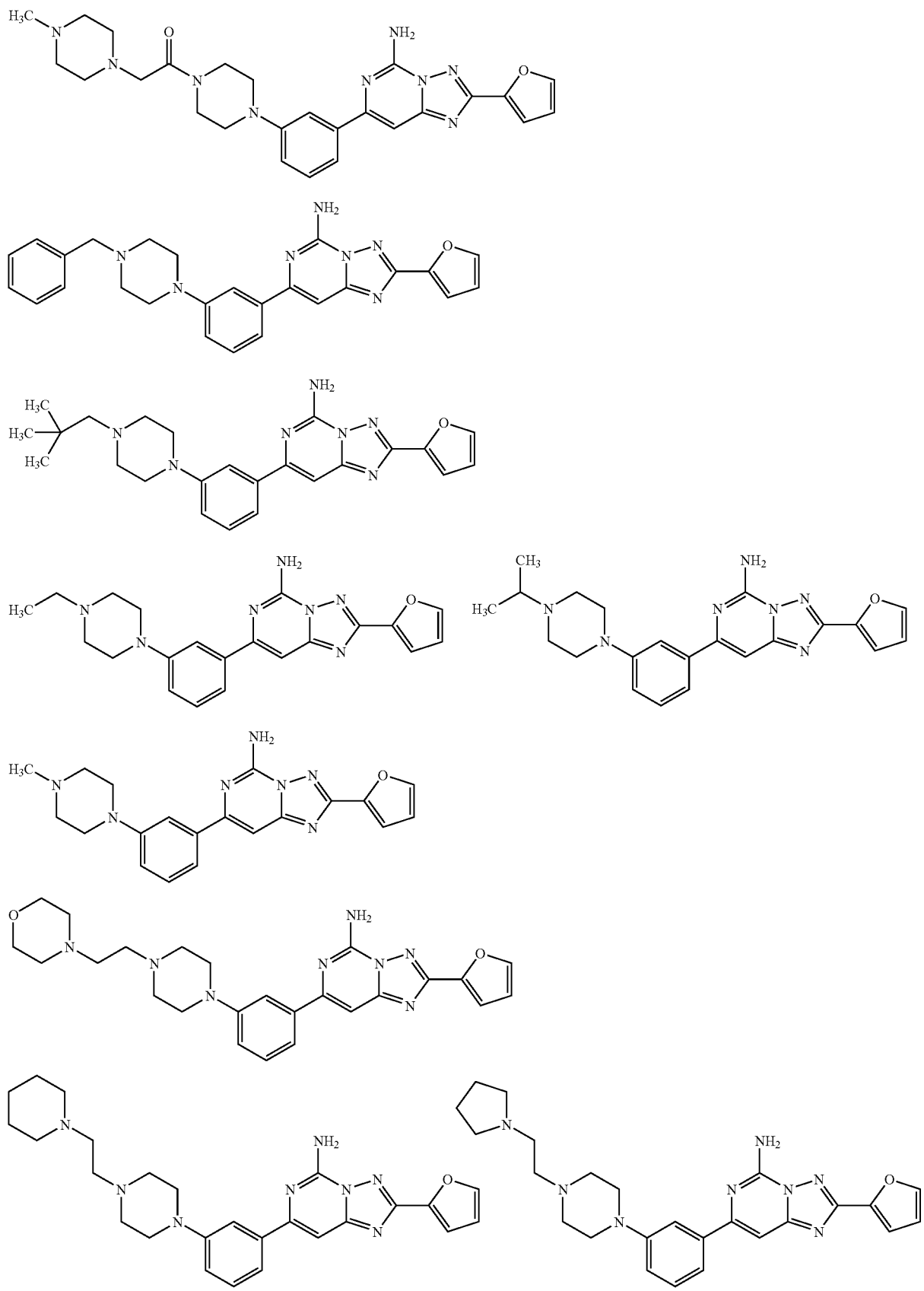

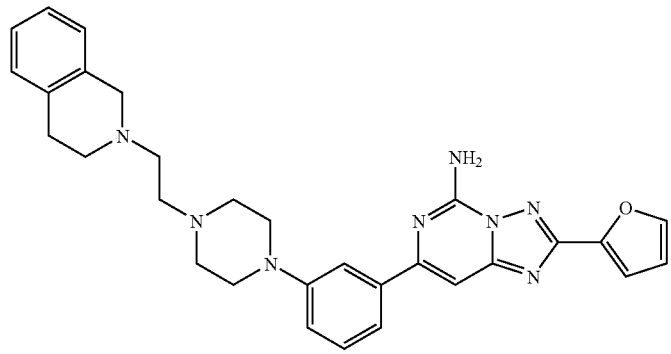
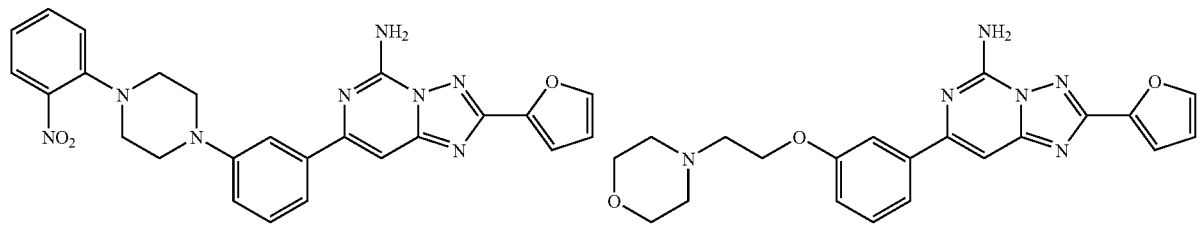
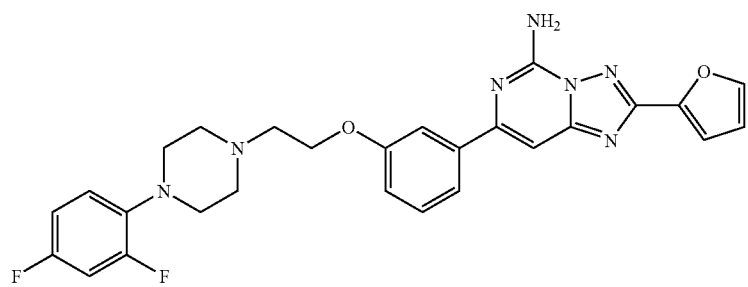
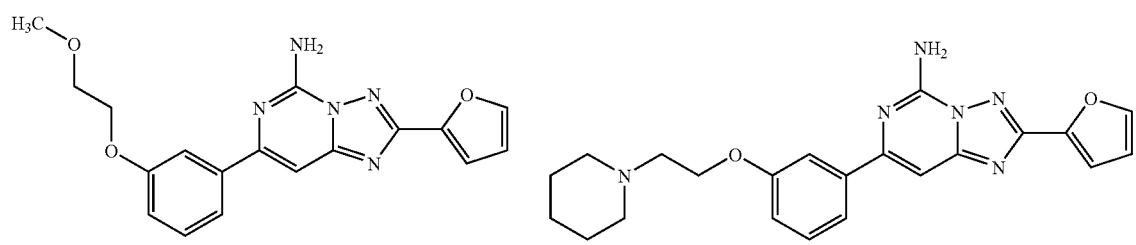
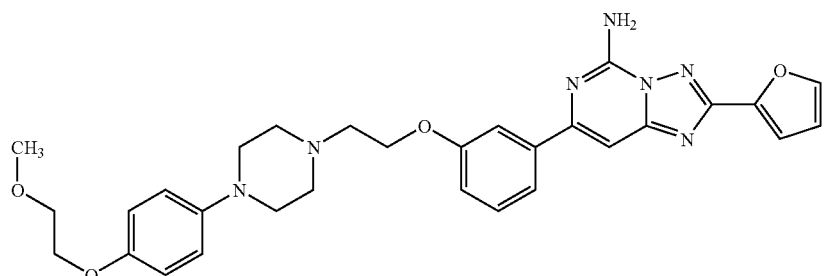
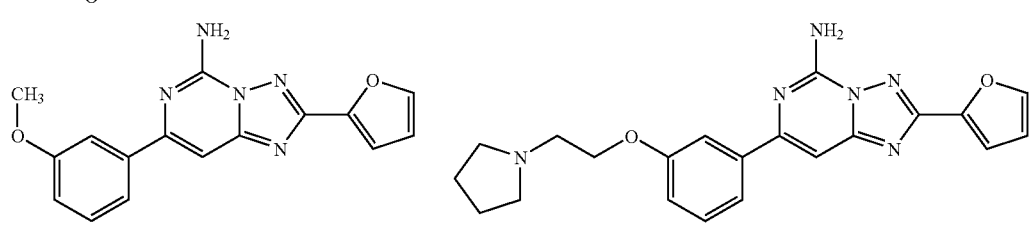

-continued
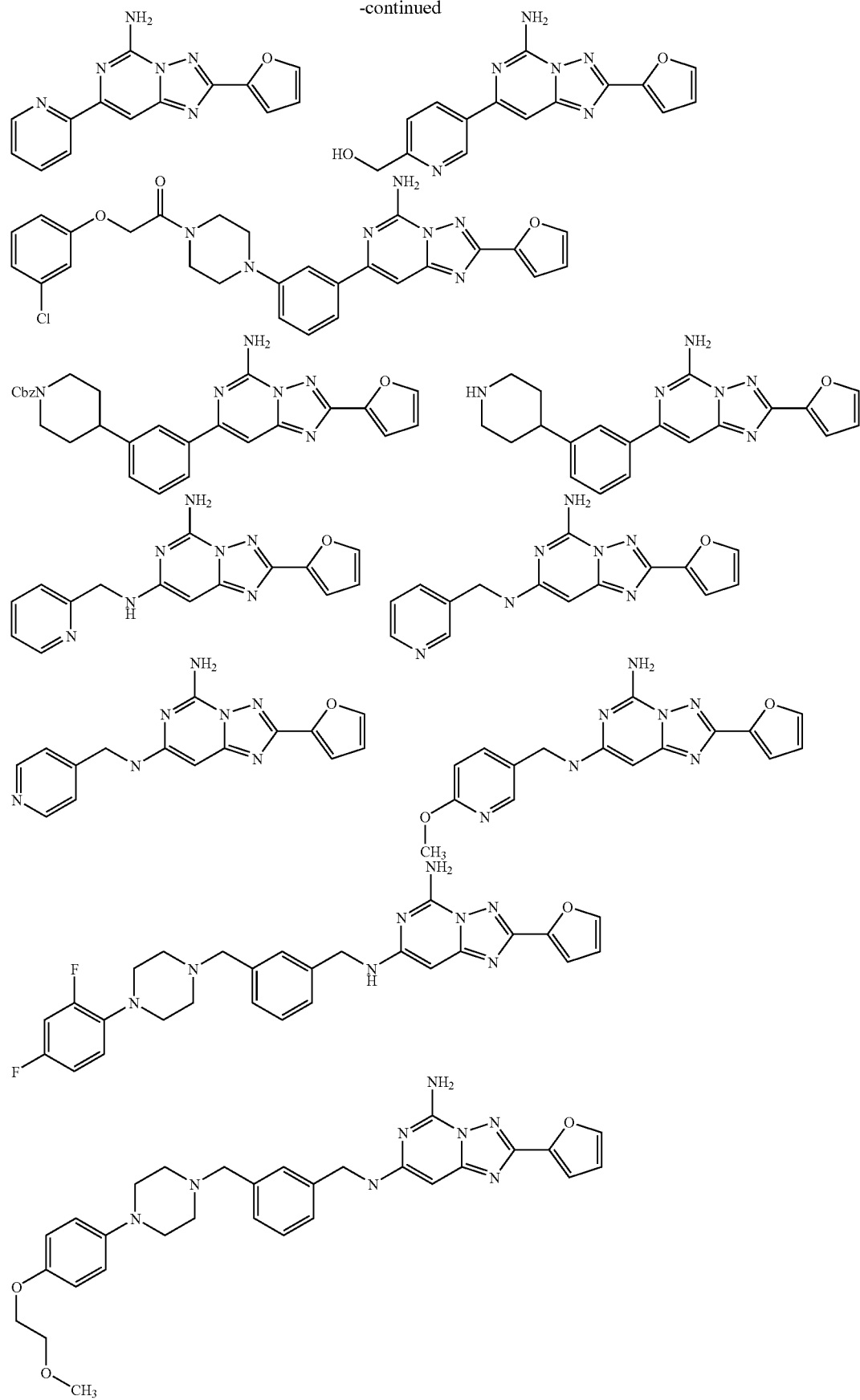

147 148
-continued
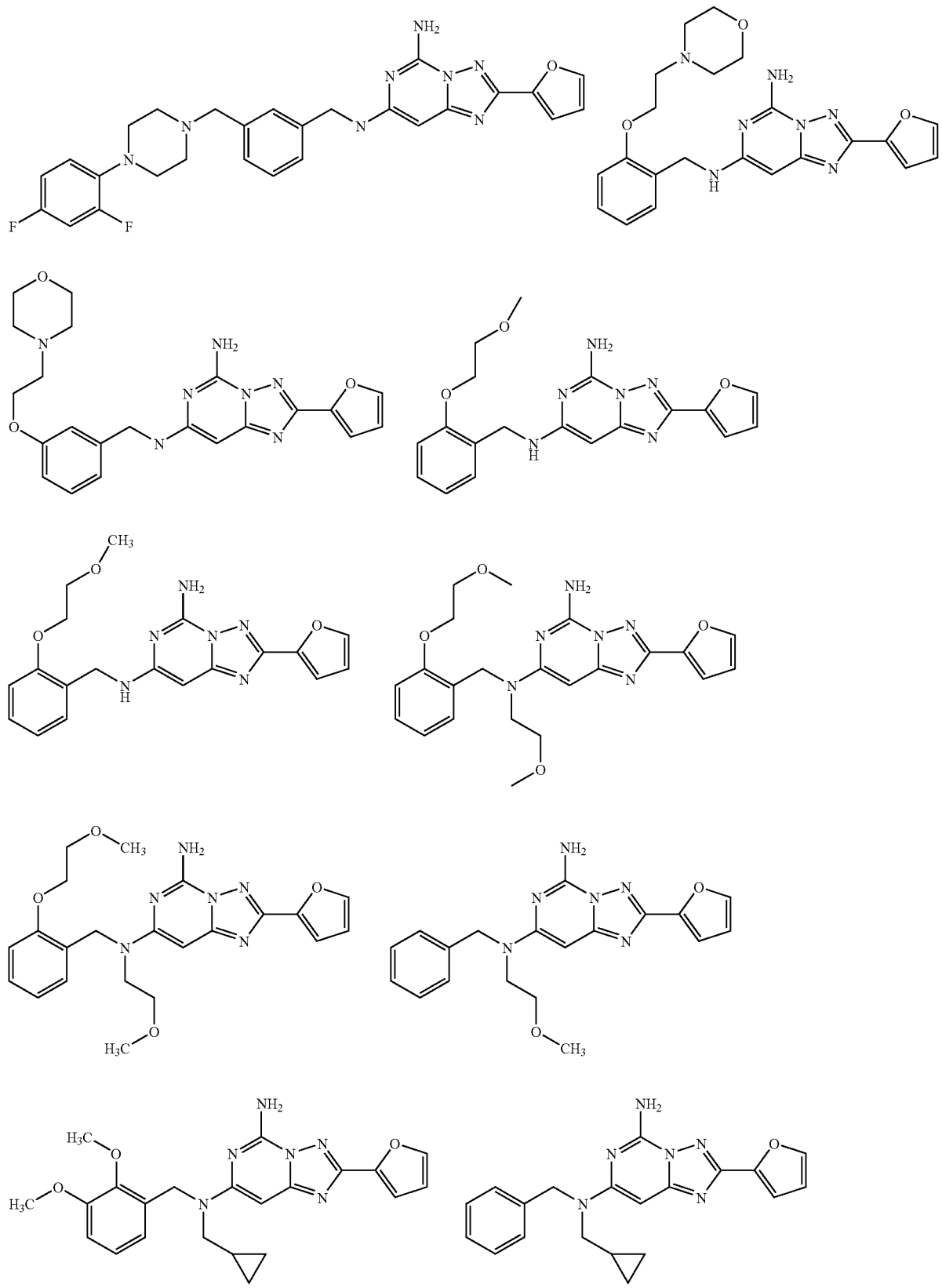

149
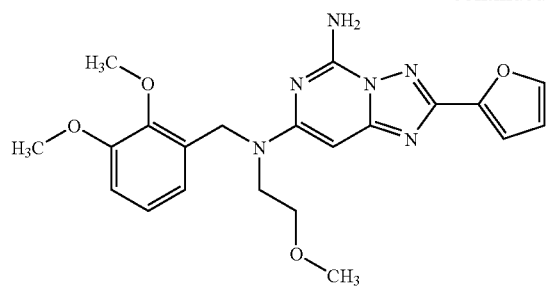
150
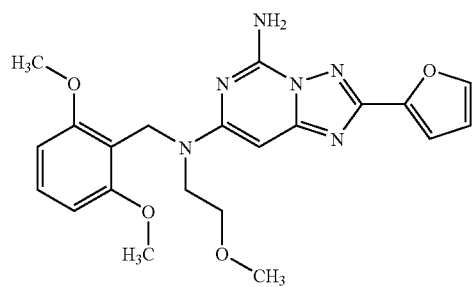
-continued
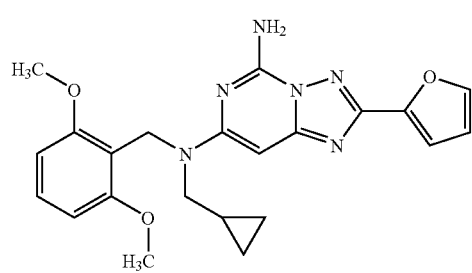
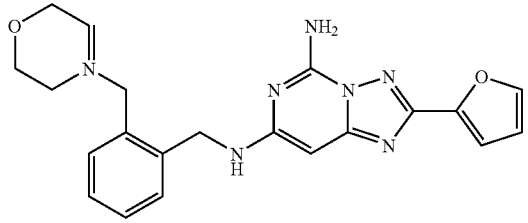
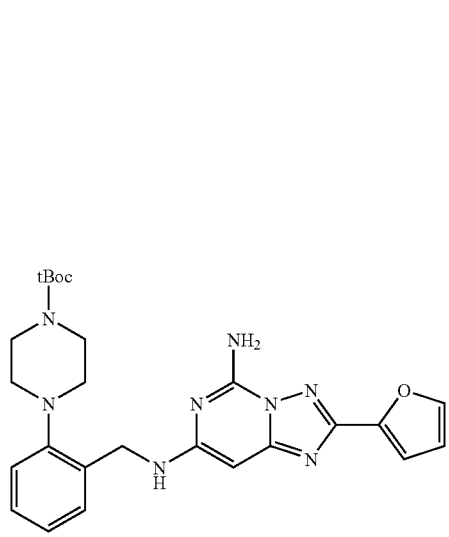
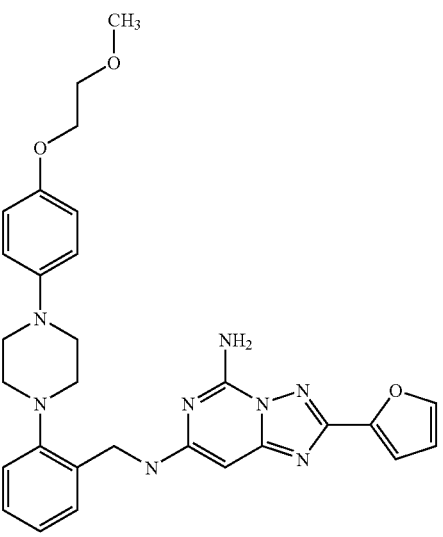
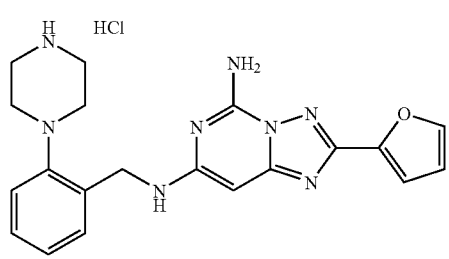
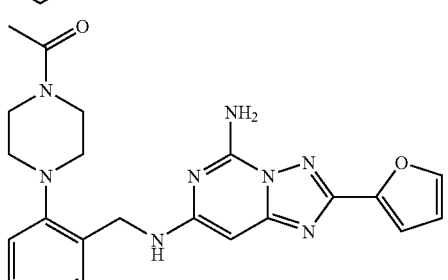
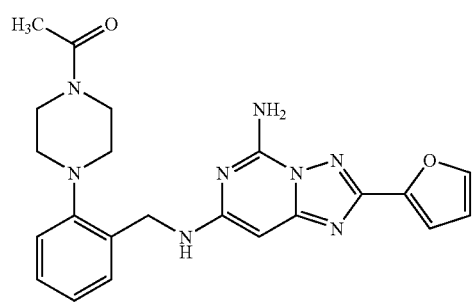
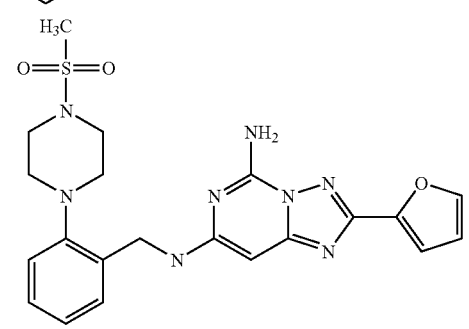 and

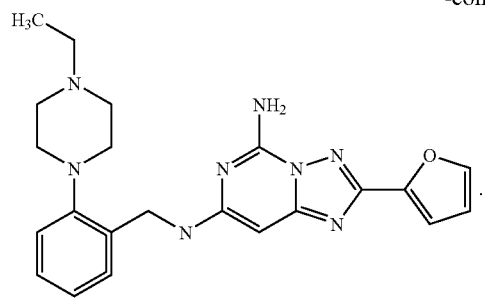
6. The compound according to claim 5 selected from the group consisting of:
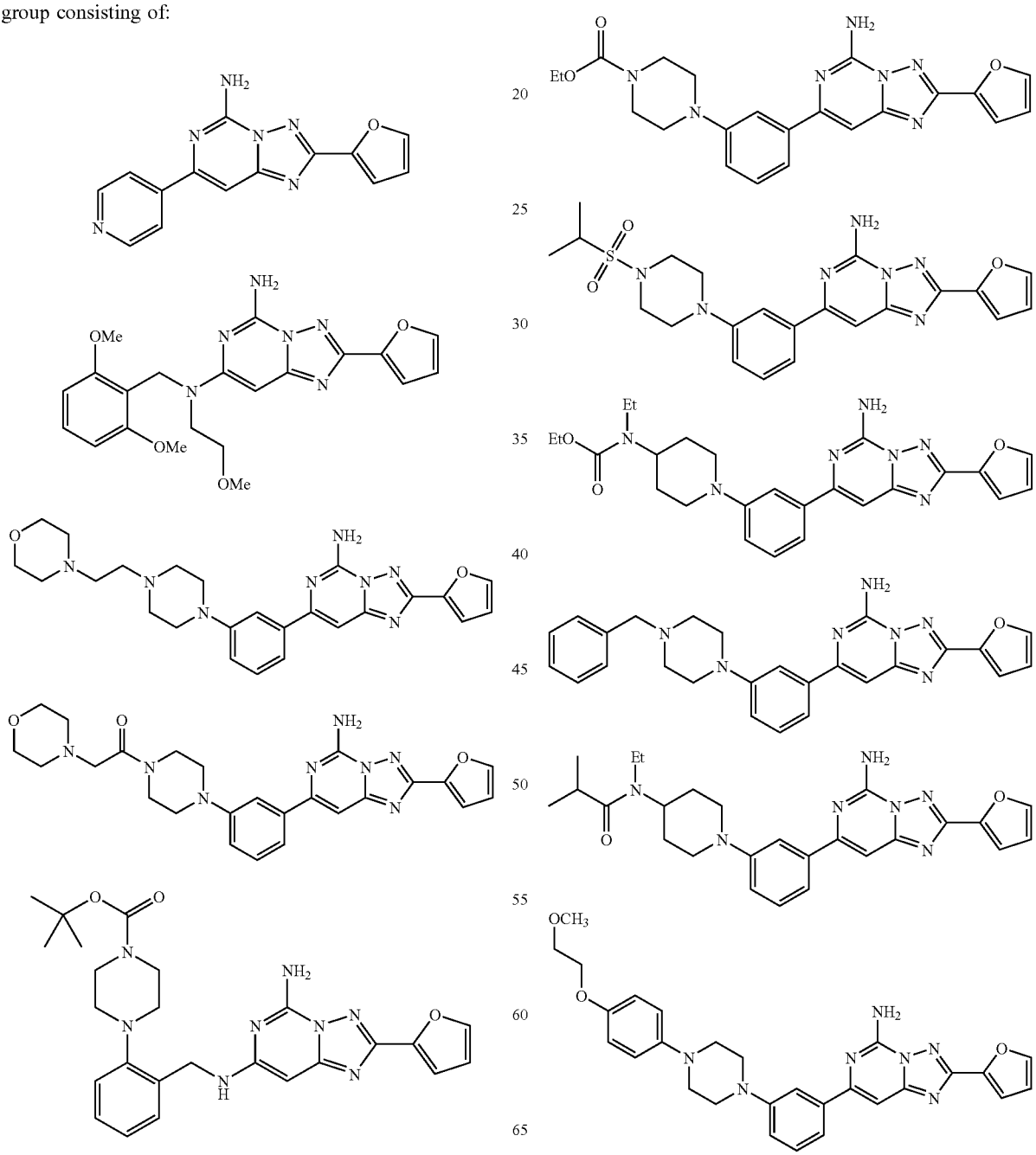

-continued
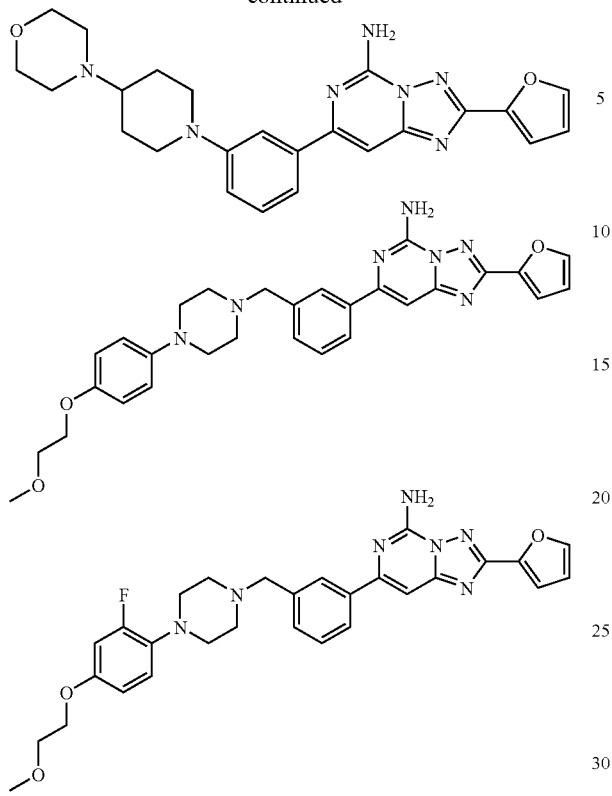
-continued
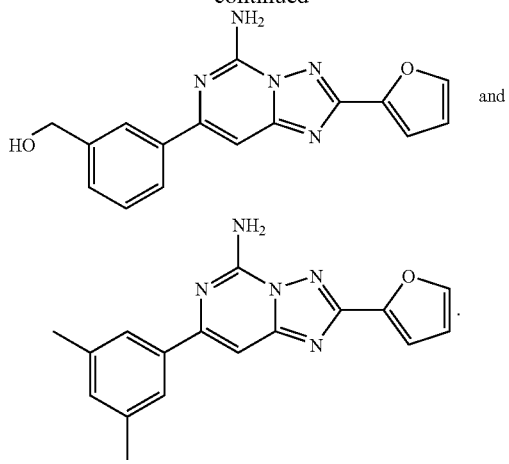
7. A pharmaceutical composition comprising one or more compounds of claim 1 and one or more pharmaceutically acceptable carriers.
8. A method of treating psychoses, comprising administering one or more compounds of claim 1 to a patient in need of such treatment.
* * * * *